US008034553B2

(12) United States Patent
McGrath

(10) Patent No.: US 8,034,553 B2
(45) Date of Patent: Oct. 11, 2011

(54) BIOMARKERS FOR WOUND HEALING

(75) Inventor: Kevin P. McGrath, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 587 days.

(21) Appl. No.: 10/876,787

(22) Filed: Jun. 24, 2004

(65) Prior Publication Data
US 2005/0287535 A1 Dec. 29, 2005

(51) Int. Cl.
*C12Q 1/68* (2006.01)
*C12P 19/34* (2006.01)
*C07H 21/04* (2006.01)
(52) U.S. Cl. ........ 435/6; 435/91.2; 536/24.3; 536/24.31
(58) Field of Classification Search .................. None
See application file for complete search history.

(56) References Cited

U.S. PATENT DOCUMENTS

| | | | |
|---|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,036,945 A | 7/1977 | Haber |
| 4,275,149 A | 6/1981 | Litman et al. |
| 4,277,437 A | 7/1981 | Maggio |
| 4,331,647 A | 5/1982 | Goldenberg |
| 4,366,241 A | 12/1982 | Tom et al. |
| 4,376,110 A | 3/1983 | David et al. |
| 5,143,854 A | 9/1992 | Pirrung et al. |
| 5,723,286 A | 3/1998 | Dower et al. |
| 5,733,731 A | 3/1998 | Schatz et al. |
| 5,834,432 A | 11/1998 | Rodgers et al. |
| 5,846,722 A | 12/1998 | Kauvar et al. |
| 5,925,523 A | 7/1999 | Dove et al. |
| 5,928,868 A | 7/1999 | Liu et al. |
| 5,955,280 A | 9/1999 | Vidal et al. |
| 6,004,746 A | 12/1999 | Brent et al. |
| 6,096,709 A | 8/2000 | Rodgers et al. |
| 6,177,407 B1 | 1/2001 | Rodgers et al. |
| 6,294,655 B1 | 9/2001 | Ford et al. |
| 6,337,072 B1 | 1/2002 | Ford et al. |
| 6,344,316 B1 | 2/2002 | Lockhart et al. |
| 6,372,892 B1 | 4/2002 | Ballinger et al. |
| 6,444,646 B1 | 9/2002 | Rodgers et al. |
| 6,482,800 B1 | 11/2002 | Rodgers et al. |
| 6,524,527 B2 | 2/2003 | Fimreite et al. |
| 6,524,795 B1 | 2/2003 | Francis et al. |
| 6,541,623 B1 | 4/2003 | Ford et al. |
| 6,551,785 B2 | 4/2003 | Saverio di Giovine et al. |
| 2003/0166069 A1 | 9/2003 | Welcher et al. |

FOREIGN PATENT DOCUMENTS

| | | |
|---|---|---|
| WO | WO-90/15070 A1 | 12/1990 |
| WO | WO-92/10092 A1 | 6/1992 |
| WO | WO-93/09668 A1 | 5/1993 |
| WO | WO-02/068579 A2 | 9/2002 |
| WO | WO-2006/007254 A2 | 1/2006 |

OTHER PUBLICATIONS

Ishida, Y. et al. Absence of IL-1 Receptor Antagonist Impaired Wound Healing along with Aberrant NF-KB Activation and a Reciprocal Suppression of TGF-beta Signal Pathway, J. Immunol. 176:5598-5606, 2006.*
Levy, B. How to Explain the Differences Between Renin Angiotensin System Modulators, Am J Hypertens. 18(9 Pt 2):134S-141S, 2005.*
Lucentini, J. Gene Association Studies Typically Wrong, The Scientist 18(24):20, 2004.*
Wu, T.D. Analysing Gene Expression Data from DNA Microarrays to Identify Candidate Genes, Journal of Pathology 195:53-65, 2001.*
Chen, G. et al. Discordant Protein and mRNA Expression in Lung Adenocarcinomas, Molecular and Cellular Proteomics 1(4):304-13, 2002.*
Fivenson, D.P. et al. Chemokine and Inflammatory Cytokine Changes During Chronic Wound Healing, Wound Repair and Regeneration 5(4):310-322, 1997.*
Wang, X. et al. Interleukin-1 Receptor and Receptor Antagonist Gene Expression After Focal Stroke in Rats, Stroke 28(1):155-161, 1997.*
Pusztai and Hess. Clinical trial design for microarray predictive marker discovery and assesment. Annals of Oncology, vol. 15, pp. 1731-1737, 2004.*
Golub et al. Molecular classification of cancer: Class discovery and class prediction by gene expression monitoring. Science, Bol. 286, pp. 531-537, Oct. 1999.*
Takayanagi et al. Molecular cloning, sequence analysis and expression of cDNA encoding human type-1 angiotensin II receptor. Biochemical and Biophysical Research Communications vol. 183, No. 2, pp. 910-916, Mar. 1992.*
Bigler et al. Interleukin-1 receptor antagonist production by human keratinocytes. The Journal of Investigative Dermatology, vol. 98, No. 1, pp. 38-44, Jan. 1992.*
Yamada et al. Human inositol 1,4,5-trisphosphate type-1 receptor, InsP3R1: structure, funciton, regulation of expression and chromosomal location. The Biochemical Journal vol. 302, pp. 781-790, Sep. 1994.*
Cohen et al. Role of the angiotensin II type-2 receptor in radiation nephropathy. Translational Research: The Journal of Laboratory and Clinical Medicine vol. 150, No. 2, pp. 106-115, May 2007.*
Cole et al. Early gene expression profile of human skin to injury using high-denisty cDNA microarrays. Wound Repair and Regeneration, vol. 9, No. 5, pp. 360-370, 2001.* GEO Accession No. GPL538 gene list for Research Genetics GF211 Microarray Filter, printed on Feb. 14, 2009 from http://www.ncbi.nlm.nih.gov/geo/query/acc.cgi?acc=GPL538, p. 1/71-71/71.*
GenBank Accession No. H66070, GI: 1024810, publicly available Oct. 1995.*
GenBank Accession No. T72877, GI: 689552, publicly available Mar. 1995.*
GenBank Accession No. AA701976, GI: 2705089, publicly available Dec. 1997.*
Jiang et al. 2001. Profiling Human Gene Expression with cDNA Microarrays. Current Protocols in Molecular Biology. 53:22.3.1-22.3.26.*
Hammerberg et al. Interleukin-1 receptor antagonist in normal and psoriatic epidermis. Journal of Clinical Investigation, vol. 90, pp. 571-583, Aug. 1990.*
Haskill et al. cDNA cloning of an intracellular form of the human interleukin 1 receptor antagonist associated with epithelium. Proceedings of the National Academy of Science, USA, vol. 88, pp. 3681-3685, May 1991.*

(Continued)

*Primary Examiner* — Jennifer Dunston
(74) *Attorney, Agent, or Firm* — Dority & Manning, P.A.

(57) ABSTRACT

The invention relates to the discovery that in chronic wounds the expression levels of certain genes are altered relative to the expression levels observed in healthy tissues.

17 Claims, No Drawings

OTHER PUBLICATIONS

Cole et al. Human Genomics and Microarrays: Implications for the Plastic Surgeon. Plastic and Reconstructive Surgery, vol. 110, No. 3, pp. 849-858, Sep. 2002.*

Hammerberg et al. Interleukin-1 receptor antagonist in normal and psoriatic epidermis. Journal of Clinical Investigation, vol. 90, pp. 571-583, Aug. 1992.*

Bigler et al. Interleukin-1 receptor antagonist production by human keratinocytes. The Journal of Investigative Dermatology, vol. 98, No. 1, pp. 38-44, Jan. 1992.*

Blackshaw et al. Type 3 inositol 1,4,5-tripphosphate receptor modulates cell death. The FASEB Journal, vol. 14, pp. 1375-1379, Jul. 2000.*

Maranto, AR. Primary structure, ligand binding, and localization of the human type 3 inositol 1,4,5-triphosphate receptor expressed in intestinal epithelium. The Journal of Biological Chemistry, vol. 269, No. 2, pp. 1222-1230, Jan. 1994.*

Rodgers et al. Development of angiotensin (1-7) as an agent to accelerate dermal repair. Wound Repair and Regeneration, vol. 9, No. 3, pp. 238-247, 2001.*

Takayanagi et al. Molecular cloning, sequence analysis and expression of a cDNA encoding human type-1 angiotensin II receptor. Biochemical and Biophysical Research Communications, vol. 183, No. 2, pp. 910-916, Mar. 1992.*

Joseph, S. K., "The Inositol Triphosphate Receptor Family", *Cellular Signalling*, 8(1), (1996), 1-7.

Schroeder, R. A., et al., "Inhibition of the Inositol Triphosphate Receptor Increases Endotoxin-Mediated Nitric Oxide Synthesis in Macrophages", *Transplantation Proceedings*, 29(6), (1997), 2569-2570.

Worley, P. F., et al., "Characterization of Inositol Trisphosphate Receptor Binding in Brain", *The Journal of Biological Chemistry*, 262(25), (1987), 12132-12136.

"Partial International Search Report for corresponding PCT Application No. PCT/US2005/019151", 3 pgs.

Arend, William P., et al., "Effects of Immune Complexes on Production by Human Monocytes of Interleukin 1 or an Interleukin 1 Inhibitor", *The Journal of Immunology*, 134(6), (1985),3868-3875.

Barnett, Anthony H., "The Role of Angiotensin II Receptor Antagonists in the Management of Diabetes", *Blood Pressure*, 10(Suppl 1), (2001),21-26.

Barringer, Kevin J., et al., "Blunt-End and Single-Strand Ligations by *Escherichia coli* Ligase: Influence on an in vitro Amplification Scheme", *Gene*, 89(1), (1990),117-122.

Bresnihan, Barry, "Treatment of Rheumatoid Arthritis With Recombinant Human Interleukin-1 Receptor Antagonist", *Arthritis & Rheumatism*, 41(12), (1998),2196-2204.

Burnier, Michel, et al., "The Comparative Pharmacology of Angiotensin II Receptor Antagonists", *Blood Pressure*, 10(Suppl. 1), (2001),6-11.

Carter, D. B., et al., "Purification, Cloning, Expression and Biological Characterization of an Interleukin-1 Receptor Antagonist Protein", *Nature*, 344(6267), (1990),633-638.

Cohen, Stanley B., et al., "Interleukin 1 Receptor Antagonist Anakinra Improves Functional Status in Patients With Rheumatoid Arthritis", *The Journal of Rheumatology*, 30(2), (2002),225-231.

Dinarello, Charles A., et al., "Multiple Biological Activities of Human Recombinant Interleukin 1", *Journal of Clinical Investigation*, 77, (1986),1734-1739.

Eberwine, James, et al., "Analysis of Gene Expression in Single Live Neurons", *Proc. Natl. Acad. Sci. USA*, 89(7), (1992),3010-3014.

Eisenberg, Stephen P., et al., "Primary Structure and Functional Expression From Complimentary DNA of a Human Interleukin-1 Receptor Antagonist", *Nature*, 343(256), (1990),341-346.

Fodor, Stephen P., et al., "Light-Directed, Spatially Addressable Parallel Chemical Synthesis", *Science*, 251(4995), (1991),767-773.

Guatelli, John C., et al., "Isothermal, in vitro Amplification of Nucleic Acids by a Multienzyme Reaction Modeled After Retroviral Replication", *Proc. Natl. Acad. Sci. USA*, 87(5), (1990),1874-1878.

Hamilton, B. J., et al., "hnRNP A2 and hnRNP L Bind the 3'UTR of Glucose Transporter 1 mRNA and Exist as a Complex in Vivo", *Biochemical and Biophysical Research Communications*, 261(3), (1999),646-651.

Hannum, Charles L., et al., "Interleukin-1 Receptor Antagonist Activity of a Human Interleukin-1 Inhibitor", *Nature*, 343(6256), (1990),336-340.

Harlan, John M., "Neutrophil-Mediated Vascular Injury", *Acta Medica Scandinavica*, (Supplementum 715), (1987),123-129.

Harris, Maureen I., et al., "Prevalence of Diabetes and Impaired Glucose Tolerance and Plasma Glucose Levels in U.S. Population Aged 20-74 Yr", *Diabetes*, 36(4), (1987),523-534.

Hernández-Hernández, R. , et al., "Angiotensin II Receptor Antagonists in Arterial Hypertension", *Journal of Human Hypertension*, 14(Suppl 1), (2000),S69-S72.

Ito, Masaki, et al., "Regulation of Blood Pressure by the Type 1A Angiotensin II Receptor Gene", *Proc. Natl. Acad. Sci. USA*, 92(5), (1995),3521-3525.

Janiak, Philip, et al., "Role of Angiotensin Subtype 2 Receptor in Neointima Formation After Vascular Injury", *Hypertension*, 20(6), (1992),737-745.

Kauffman, Raymond F., et al., "Losartan, a Nonpeptide Angiotensin II (Ang II) Receptor Antagonist, Inhibits Neointima Formation Following Balloon Injury to Rat Carotid Arteries", *Life Sciences*, 49(25), (1991),PL-223-PL-228.

Kimura, Birgitta, et al., "Changes in Skin Angiotensin II Receptor in Rats Dduring Wound Healing", *Biochemical and Biophysical Research Communications*, 187(2), (1992),1083-1090.

Köhler, G. , et al., "Continuous Cultures of Fused Cells Secreting Antibody of Predefined Specificity", *Nature*, 256(5517), (1975),495-497.

Kwoh, D. Y., et al., "Transcription-Based Amplification System and Detection of Amplified Human Immunodeficiency Virus Type 1 With a Bead-Based Sandwich Hybridization Format", *Proc. Natl. Acad. Sci. USA*, 86, (1989),1173-1177.

Landegren, Ulf , et al., "A ILgase-Mediated Gene Detection Technique", *Science*, 241, (1988),1077-1080.

Marcotte, Edward M., et al., "A Combined Algorithm for Genome-Wide Prediction of Protein Function", *Nature*, 402, (1999),83-86.

Palazzolo, Michael J., et al., "Phage Lambda cDNA Cloning Vectors for Subtractive Hybridization, Fusion-Protein Synthesis and Cre-loxP Automatic Plasma Subcloning", *Gene*, 88(1), (1990),25-36.

Phillips, M. I., et al., "Chapter 21—Angiotensin Receptor Stimulation of Transforming Growth Factor-Beta in Rat Skin and Wound Healing", *In: Angiotensin Receptors*, Saavedra, J. M., et al., Editors, Plenum Press, New York, NY,(1994),377-396.

Porter, R. R., "The Hydrolysis of Rabbit γ-Globulin and Antibodies With Crystalline Papain", *The Biochemical Journal*, 73, (1959),119-126.

Prescott, Margaret F., et al., "Angiotensin-Converting Enzyme Inhibitor Versus Angiotensin II, $AT_1$ Receptor Antagonist", *American Journal of Pathology*, 139(6), (1991),1291-1296.

Ramahi, Tarik M., "Expanded Role for ARBs in Cardiovascular and Renal Disease? Recent Observations Have Far-Reaching Implications", *Postgraduate Medicine*, 109(4), (2001),115-122.

Seckinger, Philippe, et al., "A Urine Inhibitor of Interleukin 1 Activity That Blocks Ligand Binding", *The Journal of Immunology*, 139(5), (1987),1546-1549.

Siragy, Helmy, "Angiotensin II Receptor Blockers: Review of the Binding Characteristics", *The Journal of Cardiology*, 84(10A), (1999),3S-8S.

Takahashi, N., et al., "Association of a Polymorphism at the 5'-Region of the Angiotensin II Type 1 Receptor With Hypertension", *Ann. Hum. Genet.*, 64(3), (2000),197-205.

Van Gelder, Russell N., et al., "Amplified RNA Synthesized From Limited Quantities of Heterogeneous cDNA", *Proc. Natl. Acad. Sci. USA*, 87, (1990),1663-1667.

Viswanathan, Mohan, et al., "Expression of Angiotensin II AT2 Receptor in the Rat Skin During Experimental Wound Healing", *Peptides 13 (4 )*, (1992),783-786.

Wang, William Y. S., et al., "Association of Angiotensin II Type 1 Receptor Gene Polymorphism With Essential Hypertension", *Clinical Genetics*, 51(1), (1997),31-34.

Weiss, Stephen J., "Tissue Destruction by Neutrophils", *The New England Journal of Medicine*, 320(6), (1989),365-376.

Wu, Dan Y., et al., "The Ligation Amplification Reaction (LAR)—Amplification of Specific DNA Sequences Using Sequential Rounds of Template-Dependent Ligation", *Genomics*, 4(4), (1989),560-569.

El-Daher, S S., "Distinct localization and function of (1,4,5)IP(3) receptor subtypes and the (1,3,4,5)IP(4) receptor GAP1(IP4BP) in highly purified human platelet membranes", *Blood*, 95(11), (Jun. 1, 2001),3412-22.

Maranto, A R., "Primary structure, ligand binding, and localization of the human type 3 inositol 1,4,5-trisphosphate receptor expressed in intestinal epithelium", *Journal of Biological Chemistry*, 269(2), (Jan. 14, 1994),1222-30.

Yamamoto-Hino, M , et al., "Cloning and characterization of human type 2 and type 3 inositol 1,4,5-trisphosphate receptors", *Receptors Channels*, 2(1), (1994),9-22.

\* cited by examiner

BIOMARKERS FOR WOUND HEALING

FIELD OF THE INVENTION

The present invention relates generally to the field of wound healing, to methods for monitoring the status and rate of healing wounds and to methods for identifying agents that can facilitate the repair and healing of wounds, particularly chronic wounds.

BACKGROUND OF THE INVENTION

Acutely injured tissues generally undergo a well-choreographed set of repair processes, usually characterized in three major phases: the inflammatory phase, initiated almost immediately after trauma occurs (lasting from 1-3 days); the proliferative phase, in which new tissue is formed (lasting from 3 to 14 days); and the remodeling phase, involving wound contraction, accumulation of collagen, and scar formation (this final phase can last for several months).

In contrast, chronic wounds fail to exhibit any well-defined healing processes. Some wounds remain in a state of chronic inflammation, while others simply fail to initiate tissue regrowth. Chronic wounds will often remain refractory to traditional treatments for years. For venous stasis ulcers, this is a particularly vexing problem; standard compression therapy only works on about 50% of the time, and there are few alternative treatments. Currently there are approximately 1.3 million individuals who suffer from these wounds in the U.S., with a treatment cost of over $730 million in 1998.

Factors leading to the failure of chronic wounds to heal are largely unknown. In fact, the entire process by which chronic wounds fail to heal is poorly understood. If factors and mechanisms contributing to the failure of healing in chronic wounds were identified, new treatment regimens could be developed. Therefore, a need exists for biomarkers of chronic wounds and for new procedures and formulations for treating wounds.

SUMMARY OF THE INVENTION

The invention relates to the discovery that the expression of certain genes is different in wound tissues compared to the expression of those same genes in healthy tissues. For example, expression levels of angiotensin II receptor, interleukin I receptor antagonist or inositol triphosphate receptor 3 is significantly reduced in tissue samples from chronic wounds relative to healthy tissue samples. On the other hand, the expression of interleukins, growth factors and collagens tends to be increased in chronic wound tissues. According to the invention, angiotensin II receptor, interleukin I receptor antagonist, inositol triphosphate receptor 3, certain interleukins, growth factors and collagens are markers for wound status. Thus, for example, increased expression of angiotensin II receptor, interleukin I receptor antagonist or inositol triphosphate receptor 3 in a wounded tissue sample indicates that the tissue is healing, whereas decreased expression indicates that the wounded tissue is in danger of becoming a chronic wound.

In one aspect, the invention provides a method for monitoring wound status in a wound tissue sample from a mammalian subject by quantifying angiotensin II receptor, interleukin I receptor antagonist, inositol triphosphate receptor 3, interleukin, growth factor and/or collagen expression levels in the wound tissue sample. The method can further include comparing the expression levels of interleukin I receptor antagonist, inositol triphosphate receptor 3, interleukin, growth factor and/or collagen in the wound tissue sample with expression levels of interleukin I receptor antagonist, inositol triphosphate receptor 3, interleukin, growth factor and/or collagen in a healthy tissue sample taken from the same mammalian subject as the wound tissue sample. In some embodiments, the wound tissue sample and the healthy tissue sample are of the same tissue type (e.g. both, epidermal or skin tissue).

In another aspect, the invention provides a method of identifying an agent useful for treating a chronic wound comprising contacting a wound tissue sample from a mammalian subject with a test agent and observing whether expression levels of angiotensin II receptor, interleukin I receptor antagonist or inositol triphosphate receptor 3 increase compared to a wound tissue sample that was not contacted with the test agent.

The healthy tissue can be from the same mammalian subject as the wound tissue sample. In some embodiments the mammalian subject is a human subject.

In another aspect, the invention provides a method of identifying an agent useful for treating a chronic wound comprising contacting an epithelial cell sample with a test agent and observing whether expression levels of angiotensin II receptor, interleukin I receptor antagonist or inositol triphosphate receptor 3 increase compared to an epithelial cell sample that was not contacted with the test agent.

In another embodiment, the invention provides a method of identifying an agent useful for treating a chronic wound comprising contacting a wound tissue sample or an epithelial cell sample with a test agent and observing whether expression levels of interleukin, growth factor and/or collagen decrease compared to a wound tissue sample or an epithelial cell sample that was not contacted with the test agent.

The expression levels can be quantified by any assay available to one of skill in the art. For example, in some embodiments the expression levels are quantified by hybridization assay of RNA obtained from the wound tissue sample to a probe complementary to angiotensin II receptor, interleukin I receptor antagonist, inositol triphosphate receptor 3, interleukin, growth factor and/or collagen mRNA. For example, the probe used in the hybridization assay can be complementary to SEQ ID NO:1, SEQ ID NO:3 or SEQ ID NO:5. In some embodiments, the hybridization assay can involve hybridization of wound tissue sample RNA to an array of probes complementary to SEQ ID NO:1, SEQ ID NO:3 or SEQ ID NO:5. The hybridization assay can also involve hybridization of a northern blot of wound tissue sample RNA to probes complementary to SEQ ID NO:1, SEQ ID NO:3 or SEQ ID NO:5. In other embodiments, the expression levels can also be quantified by amplification of wound tissue sample RNA.

The expression levels can also be quantified by immunoassay of the wound tissue sample using an antibody directed against angiotensin II receptor, interleukin I receptor antagonist, inositol triphosphate receptor 3, interleukin, growth factor and/or collagen protein. For example, the antibody can be directed against a peptide within SEQ ID NO:2, SEQ ID NO:4 or SEQ ID NO:6.

DETAILED DESCRIPTION OF THE INVENTION

The invention is directed to methods for detecting and monitoring wounds that may become chronic wounds. According to the invention, the expression of certain genes is altered in chronic wound tissues. For example, the expression levels of angiotensin II receptor, interleukin I receptor antagonist or inositol triphosphate receptor 3 tend to be reduced in chronic wounds relative to healthy tissues. In contrast the expression of interleukins, growth factors and collagens tend to be increased in chronic wound tissues.

According to the invention, these observations can be used to detect and monitor chronic wounds. In particular, the expression levels of these genes can be monitored by testing a wound tissue sample. If the expression of interleukins, growth factors or collagens has increased while the expression angiotensin II receptor, interleukin I receptor antagonist or inositol triphosphate receptor 3 is reduced, then the wound from which the tissue sample was taken may be in danger of becoming a chronic wound or the prognosis of a previously diagnosed chronic wound may be worsening. Conversely, if the expression of interleukins, growth factors or collagens is reduced while the expression angiotensin II receptor, interleukin I receptor antagonist or inositol triphosphate receptor 3 has increased, then the wound from which the tissue sample was taken may be healing.

The invention also provides methods for identifying agents useful for treating chronic wounds that involve contacting a cell or tissue sample with a test agent and observing whether the test agent increases the expression of angiotensin II receptor, interleukin I receptor antagonist or inositol triphosphate receptor 3. One of skill in the art can also observe whether the test agent decreases the expression of interleukins, growth factors or collagens in the cell or tissue sample. Test agents that alter the expression of these genes are candidates for treating chronic wounds.

Definitions

"Expression" refers to the transcription and/or translation of an endogenous gene or a nucleic acid segment in cells. Expression also refers to the transcription and stable accumulation of sense (mRNA) or functional RNA. Expression may also refer to the production of protein.

"Altered levels" refers to a level of expression of a gene in a cell, tissue or organism that differs from that of normal or healthy cells, tissues or organisms.

"Overexpression" refers to a level of expression in cells, tissues or organisms that exceeds levels of expression in normal or healthy cells, tissues or organisms.

The term "quantifying" when used in the context of quantifying nucleic acid abundances or concentrations (e.g., transcription levels of a gene) can refer to absolute or to relative quantification. Absolute quantification may be accomplished by inclusion of known concentration(s) of one or more target nucleic acids (e.g. control nucleic acids or with known amounts the target nucleic acids themselves) and referencing the hybridization intensity of unknowns with the known target nucleic acids (e.g. through generation of a standard curve). Alternatively, relative quantification can be accomplished by comparison of hybridization signals between two or more genes or between two or more treatments to quantify the changes in hybridization intensity and, by implication, transcription level.

"Reduced expression" refers to a level of expression in test cells, tissues or organisms that is less than levels of expression in control cells, tissues or organisms. In some embodiments, the control cells, tissues or organisms are normal or healthy cells, tissues or organisms. In other embodiments, the control cells, tissues or organisms are previously-obtained test cells, tissues or organisms from the same mammalian subject from which the current test cells, tissues or organisms. Such previously-obtained test cells, tissues or organisms may also have been previously tested so that the results of current and expression level assays can be compared.

Chronic Wounds

The primary goal in the treatment of wounds is to achieve wound closure. Open cutaneous wounds represent one major category of chronic wounds and include burn wounds, neuropathic ulcers, pressure sores, venous stasis ulcers, and diabetic ulcers. Open cutaneous wounds routinely heal by a process which comprises six major processes: i) inflammation, ii) fibroblast proliferation, iii) blood vessel proliferation, iv) connective tissue synthesis v) epithelialization, and vi) wound contraction. Wound healing is impaired when these processes, either individually or as a whole, do not function properly. Numerous factors can affect wound healing, including malnutrition, infection, pharmacological agents (e.g., actinomycin and steroids), diabetes, and advanced age. See Hunt and Goodson in Current Surgical Diagnosis & Treatment (Way; Appleton & Lange), pp. 86-98 (1988).

With respect to diabetes, it is known that delayed wound healing causes substantial morbidity in patients with diabetes. Diabetes mellitus is a chronic disorder of glucose metabolism and homeostasis that damages many organs. It is the eighth leading cause of death in the United States (Harris et al., Diabetes 36:523 (1987)). In persons with diabetes, vascular disease, neuropathy, infections, and recurrent trauma predispose the extremities, especially the foot, to pathologic changes. These pathological changes can ultimately lead to chronic ulceration, which may necessitate amputation.

It is known that patients suffering from venous stasis ulcers respond differently to compression therapy, but the reasons for these differences in response remain a mystery. It is clear that simply restoring appropriate blood flow to the afflicted area is not a panacea—nearly half of all patients with these types of wounds are unresponsive to this approach.

According to the invention, the key differences in wounds, and their progression and response to treatment, can be identified through an analysis of gene expression in these tissues. Hence, the invention provides methods for evaluating or monitoring wound status in a patient by examining gene expression patterns of wound tissues samples compared to the gene expression patterns of healthy tissues. These methods can be applied before, during, after or any time throughout the healing or treatment period.

In this manner, subtle differences in gene expression between healing and non-healing wounds were identified. In particular, the inventors have discovered that the expression patterns of angiotensin II receptor, interleukin I receptor antagonist and inositol triphosphate receptor 3 in wound tissues are significantly reduced relative to the expression patterns of these genes in normal, healthy tissues. Moreover, the expression levels of interleukins, growth factors and collagens are increased in chronic wound tissues.

Angiotensin II Receptor

According to the invention, the expression of the angiotensin II receptor is dramatically reduced in chronic wound tissues. In particular, in one set of experiments, the expression of angiotensin II receptor in chronic wounds was only about 2% of that observed in healthy tissues from the same patients. Hence, expression of angiotensin II receptor was reduced about 50-fold in chronic wounds relative to healthy tissues.

Therefore, according to the invention, angiotensin II receptor is a marker for chronic wounds that can be used to detect, monitor and evaluate the progress of healing in chronic wounds. Moreover, according to the invention, any agent that can increase the expression or activity of angiotensin II receptor can be used to treat wounds, including chronic wounds.

In one embodiment, the invention contemplates monitoring the expression of angiotensin II receptor as a marker for chronic wound development and healing of wounds, particularly chronic wounds.

Angiotensin II is an important physiological effector of blood pressure and volume regulation that operates by regulating vasoconstriction, aldosterone release, sodium uptake and thirst stimulation. Angiotensin II mediates its action by interacting with angiotensin II type 1 receptors. The signal is transmitted via G-proteins that activate a phosphatidylinositol-calcium second messenger system. Angiotensin II receptors are integral membrane proteins of approximately 359-363 amino acids and are predicted to contain at least 7 transmembrane domains. The N- and C-termini of us are predicted to extracellular and cytoplasmic, respectively.

Three isoforms of angiotensin II receptors have been cloned. Although angiotensin II interacts with two types of cell surface receptors, AT1 and AT2, the major cardiovascular effects appear to be mediated through AT1. Molecular cloning of the AT1 protein has shown it to be a member of the G protein-associated seven membrane transmembrane protein receptor family. AT1 receptors are expressed in the liver, kidney, aorta, lung, uterus, ovary, spleen, heart, adrenal and vascular smooth muscle. Human angiotensin II receptor type 2 has 363 amino acids and is also a G-coupled membrane receptor protein. AT2 is highly expressed in the adult myometrium with lower levels in adrenal and fallopian tube. It is also expressed at high levels in fetal kidney and intestine.

As contemplated by the invention, either the levels of angiotensin II receptor mRNA or protein can be monitored.

The levels of angiotensin II receptor mRNA can be monitored by any available procedure, including by hybridization, nucleic acid amplification, use of gene expression microarrays and the like. Sequences for angiotensin II receptor nucleic acids are available and can be used to obtain probes or primers for detecting angiotensin II receptor by these procedures. Thus, for example, sequences for human angiotensin II receptor are available in the NCBI database. See website at ncbi.nlm.nih.gov.

One example of a nucleotide sequence for human type 1 angiotensin II receptor can be found in the NCBI database at accession number BC068494 (gi: 46250426). See website at ncbi.nlm.nih.gov. This human angiotensin II receptor nucleic acid sequence is provided below as SEQ ID NO:1.

```
   1 GATTCCAGCG CCTGACAGCC AGGACCCCAG GCAGCAGCGA
  41 GTGACAGGAC GTCTGGACCG GCGCGCCGCT AGCAGCTCTG
  81 CCGGGCCGCG GCGGTGATCG ATGGGGAGCG GCTGGAGCGG
 121 ACCCAGCGAG TGAGGGCGCA CAGCCGGGAC GCCGAGGCGG
 161 CGGGCGGGAG ACCCGCACCA GCGCAGCCGG CCCTCGGCGG
 201 GACGTGACGC AGCGCCCGGG GCGCGGGTTT GATATTTGAC
 241 AAATTGATCT AAAATGGCTG GGTTTTTATC TGAATAACTC
 281 ACTGATGCCA TCCCAGAAAG TCGGCACCAG GTGTATTTGA
 321 TATAGTGTTT GCAACAAATT CGACCCAGGT GATCAAAATG
 361 ATTCTCAACT CTTCTACTGA AGATGGTATT AAAAGAATCC
 401 AAGATGATTG TCCCAAAGCT GGAAGGCATA ATTACATATT
 441 TGTCATGATT CCTACTTTAT ACAGTATCAT CTTTGTGGTG
 481 GGAATATTTG GAAACAGCTT GGTGGTGATA GTCATTTACT
 521 TTTATATGAA GCTGAAGACT GTGGCCAGTG TTTTTCTTTT
 561 GAATTTAGCA CTGGCTGACT TATGCTTTTT ACTGACTTTG
 601 CCACTATGGG CTGTCTACAC AGCTATGGAA TACCGCTGGC
 641 CCTTTGGCAA TTACCTATGT AAGATTGCTT CAGCCAGCGT
 681 CAGTTTCAAC CTGTACGCTA GTGTGTTTCT ACTCACGTGT
 721 CTCAGCATTG ATCGATACCT GGCTATTGTT CACCCAATGA
 761 AGTCCCGCCT TCGACGCACA ATGCTTGTAG CCAAAGTCAC
 801 CTGCATCATC ATTTGGCTGC TGGCAGGCTT GGCCAGTTTG
 841 CCAGCTATAA TCCATCGAAA TGTATTTTTC ATTGAGAACA
 881 CCAATATTAC AGTTTGTGCT TTCCATTATG AGTCCCAAAA
 921 TTCAACCCTC CCGATAGGGC TGGGCCTGAC CAAAAATATA
 961 CTGGGTTTCC TGTTTCCTTT TCTGATCATT CTTACAAGTT
1001 ATACTCTTAT TTGGAAGGCC CTAAAGAGGG CTTATGAAAT
1041 TCAGAAGAAC AAACCAAGAA ATGATGATAT TTTTAAGATA
1081 ATTATGGCAA TTGTGCTTTT CTTTTTCTTT TCCTGGATTC
1121 CCCACCAAAT ATTCACTTTT CTGGATGTAT TGATTCAACT
1161 AGGCATCATA CGTGACTGTA GAATTGCAGA TATTGTGGAC
1201 ACGGCCATGC CTATCACCAT TTGTATAGCT TATTTTAACA
1241 ATTGCCTGAA TCCTCTTTTT TATGGCTTTC TGGGGAAAAA
1281 ATTTAAAAGA TATTTTCTCC AGCTTCTAAA ATATATTCCC
1321 CCAAAAGCCA AATCCCACTC AAACCTTTCA ACAAAAATGA
1361 GCACGCTTTC CTACCGCCCC TCAGATAATG TAAGCTCATC
1401 CACCAAGAAG CCTGCACCAT GTTTTGAGGT TGAGTGACAT
1441 GTTCGAAACC TGTCCATAAA GTAATTTTGT GAAAGAAGGA
1481 GCAAGAGAAC ATTCCTCTGC AGCACTTCAC TACGAAATGA
1521 GCCTTAGCTA CTTTTCAGAA TTGAAGGAGA AAATGCATTA
1561 TGTGGACTGA ACCGACTTTT CTAAAGCTCT GAACAAAGC
1601 TTTTCTTTCC TTTTGCAACA AGACAAAGCA AAGCCACATT
1641 TTGCATTAGA CAGATGACGG CTGCTCGAAG AACAATGTCA
1681 GAAACTCGAT GAATGTGTTG ATTTGAGAAA TTTTACTGAC
1721 AGAAATGCAA TCTCCCTAGC CTGCTTTTGT CCTGTTATTT
1761 TTTATTTCCA CATAAAGGTA TTTAGAATAT ATTAAATCGT
1801 TAGAGGAGCA ACAGGAGATG AGAGTTCCAG ATTGTTCTGT
1841 CCAGTTTCCA AAGGGCAGTA AAGTTTTCGT GCCGGTTTTC
1881 AGCTATTAGC AACTGTGCTA CACTTGCACC TGGTACTGCA
1921 CATTTTGTAC AAAGATATGC TAAGCAGTAG TCGTCAAGTT
1961 GCAGATCTTT TTGTGAAATT CAACCTGTGT CTTATAGGTT
2001 TACACTGCCA AAACAATGCC CGTAAGATGG CTTATTTGTA
2041 TAATGGTGTT ACTAAAGTCA CATATAAAAG TTAAACTACT
2081 TGTAAAGGTG CTGCACTGGT CCCAAGTAGT AGTGTCTTCC
2121 TAGTATATTA GTTTGATTTA ATATCTGAGA AGTGTATATA
2161 GTTTGTGGTA AAAAGATTAT ATATCATAAA GTATGCCTTC
2201 CTGTTTAAAA AAGTATATA TTCTACACAT ATATATATAT
2241 GTATATCTAT ATCTCTAAAC TGCTGTTAAT TGATTAAAAT
```

```
2281  CTGGCAAAGT TATATTTACT TTAAAATAAA ATAATTTTAT

2321  TGCAAAAAAA AAAAAAAA
```

Moreover, the expression of angiotensin II receptor can be monitored by observing the levels of angiotensin II receptor protein in wounds. Angiotensin II receptor protein can be monitored using antibodies or other agents that can selectively bind to angiotensin II receptor. One example of an amino acid sequence for human type 1 angiotensin II receptor can be found in the NCBI database at accession number AAH68494 (gi: 46250427). See website at ncbi.nlm.nih.gov. This human angiotensin II receptor amino acid sequence is provided below as SEQ ID NO:2.

```
  1  MILNSSTEDG IKRIQDDCPK AGRHNYIFVM IPTLYSIIFV

41  VGIFGNSLVV IVIYFYMKLK TVASVFLLNL ALADLCFLLT

81  LPLWAVYTAM EYRWPFGNYL CKIASASVSF NLYASVFLLT

121  CLSIDRYLAI VHPMKSRLRR TMLVAKVTCI IIWLLAGLAS

161  LPAIIHRNVF FIENTNITVC AFHYESQNST LPIGLGLTKN

201  ILGFLPFLI ILTSYTLIWK ALKRAYEIQK NKPRNDDIFK

241  IIMAIVLFFF FSWIPHQIFT FLDVLIQLGI IRDCRIADIV

281  DTAMPITICI AYFNNCLNPL FYGFLGKKFK RYFLQLLKYI

321  PPKAKSHSNL STKMSTLSYR PSDNVSSSTK KPAPCFEVE
```

Interleukin I Receptor Antagonist

According to the invention, the expression of the interleukin I receptor antagonist dramatically reduced in chronic wound tissues. In particular, in one set of experiments, the expression of interleukin I receptor antagonist in chronic wounds was only about 6% of that observed in healthy tissues from the same patients. Hence, interleukin I receptor antagonist is a marker for chronic wounds that can be used to detect, monitor and evaluate the progress of healing in chronic wounds.

In one embodiment, the invention contemplates monitoring the expression of interleukin I receptor antagonist as a marker for chronic wound development and healing of wounds, particularly chronic wounds.

Cytokines are small molecular weight proteins that have a myriad of normal biological functions as well as being associated with various diseases. For example, the cytokines interleukin-1 (IL-1) and tumor necrosis factor (TNF) have been demonstrated to have multiple biological activities, with the two prominent activities being fever production and leukocyte activation. Moreover, both cytokines, alone or in combination, cause a shock state in animals that hemodynamically and hematologically is characteristic of septic shock in man caused by bacterial infection. TNF and IL-1 also play a role in various autoimmune diseases, particularly arthritis. Duff, et al., 1987, International Conference on Tumor Necrosis Factor and Related Cytotoxins, 175:10.

Endothelial cell injury, or injury to the vascular system, can occur as a result of a number of diseases in which there appears to be cytokine involvement. For example, ischemia-related injury to cells, tissues or organs is responsible for many significant clinical disorders, including stroke, vascular disease, organ transplantation, and myocardial infarction. Leukocytes, particularly, neutrophils or monocytes, are thought to be the primary causative agent and have been shown to cause extensive vascular tissue damage arising as a result of the release of oxygen-derived free radicals, as well as proteases and phospholipases from the leukocytes at the site of injury. Harlan, J. M., 1987, Acta. Med. Scand. Suppl., 715:123; Weiss, S., 1989, New England J. of Med., 320:365. Cytokines are thought to be chemotactic agents for leukocytes and may be involved in attracting them to the site of tissue injury. Additionally, other studies have shown that cytokines are involved in causing leukocytes to adhere to the vascular endothelial cell layer which sets the stage for the release of noxious chemicals that cause vascular tissue damage.

There are two forms of interleukin-1 (IL-1): interleukin-1α and interleukin-1β. Although these molecules share limited sequence homology they have similar biological activity. Dinarello, C. A., et al., 1986, Journal Clinical Invest., 77:1734. Both molecules have molecular weights of about 17.5 kD, and are produced from a precursor molecule with a molecular weight of about 31 kD.

Because IL-1 has pleiotropic biological activities many of which adversely affect the organism, it would be expected that the molecule must be tightly regulated if it is not to be injurious. Indeed, there are several reports of IL-1 inhibitors that regulate the action of IL-1. IL-1 inhibitory activity has been reported in monocyte conditioned medium, wherein the monocytes are grown on adherent immune complexes. Arend, W. P., et al., 1985, Journal of Immun., 134:3868. Additionally, an inhibitor has been reported to be present in urine. Seckinger, P., et al., 1987, Journal of Immun., 139: 1546. Lastly, two protein inhibitors, purified and cloned, that have interleukin-1 receptor antagonist activity have been reported. Hannum, et al., 1990, Nature, 343:336; Eisenberg, S., et al., 1990, Nature, 343:341; and Haskill, S., et al., U.S. Ser. No. 517,276, filed May 1, 1990 now abandoned, Carter, D. et al., 1990, Nature, 344:633.

The levels of interleukin I receptor antagonist mRNA can be monitored by any available procedure, including by hybridization, nucleic acid amplification, use of gene expression microarrays and the like. Sequences for interleukin I receptor antagonist nucleic acids are available and can be used to obtain probes or primers for detecting interleukin I receptor antagonist by these procedures. Thus, for example, sequences for human interleukin I receptor antagonist are available in the NCBI database. See website at ncbi.nlm.nih.gov.

One example of a nucleotide sequence for human interleukin I receptor antagonist can be found in the NCBI database at accession number X53296 (gi: 32578). See website at ncbi.nlm.nih.gov. This human interleukin I receptor antagonist nucleic acid sequence is provided below as SEQ ID NO:3.

```
  1  CCGACAGAAT GGAAATCTGC AGAGGCCTCC GCAGTCACCT

41  AATCACTCTC CTCCTCTTCC TGTTCCATTC AGAGACGATC

81  TGCCGACCCT CTGGGAGAAA ATCCAGCAAG ATGCAAGCCT

121  TCAGAATCTG GATGTTAAC CAGAAGACCT TCTATCTGAG

161  GAACAACCAA CTAGTTGCTG GATACTTGCA AGGACCAAAT

201  GTCAATTTAG AAGAAAAGAT AGATGTGGTA CCCATTGAGC

241  CTCATGCTCT GTTCTTGGGA ATCCATGGAG GGAAGATGTG

281  CCTGTCCTGT GTCAAGTCTG GTGATGAGAC CAGACTCCAG

321  CTGGAGGCAG TTAACATCAC TGACCTGAGC GAGAACAGAA
```

```
361  AGCAGGACAA GCGCTTCGCC TTCATCCGCT CAGACAGTGG
401  CCCCACCACC AGTTTTGAGT CTGCCGCCTG CCCCGGTTGG
441  TTCCTCTGCA CAGCGATGGA AGCTGACCAG CCCGTCAGCC
481  TCACCAATAT GCCTGACGAA GGCGTCATGG TCACCAAATT
521  CTACTTCCAG GAGGACGAGT AGTACTGCCC AGGCCTGCCT
561  GTTCCCATTC TTGCATGGCA AGGACTGCAG GGACTGCCAG
601  TCCCCCTGCC CCAGGGCTCC CGGCTATGGG GGCACTGAGG
641  ACCAGCCATT GAGGGGTGGA CCCTCAGAAG GCGTCACAAC
681  AACCTGGTCA CAGGACTCTG CCTCCTCTTC AACTGACCAG
721  CCTCCATGCT GCCTCCAGAA TGGTCTTTCT AATGTGTGAA
761  TCAGAGGACA GCAGCCCTG CACAAAGCCC TTCCATGTCG
801  CCTCTGCATT CAGGATCAAA CCCCGACCAC CTGCCCAACC
841  TGTCTCCTCT TGCCACTGCC TCTTCCTCCC TCATTCCACC
881  TTCCCATGCC CTGGATCCAT CAGGCCACTT GATGACCCCC
921  AACCAAGTGG CTCCCACACC CTGTTTTACA AAAAAGAAAA
961  GACCAGTCCA TGAGGGAGGT TTTTAAGGGT TTGTGGAAAA
1001 TGAAAATTAG GATTTCATGA TTTTTTTTTT TCAGTCCCCG
1041 TGAAGGAGAG CCCTTCATTT GGAGATTATG TTCTTTCGGG
1081 GAGAGGCTGA GGACTTAAAA TATTCCTGCA TTTGTGAAAT
1121 GATGGTGAAA GTAAGTGGTA GCTTTTCCCT TCTTTTTCTT
1161 CTTTTTTTGT GATGTCCCAA CTTGTAAAAA TTAAAAGTTA
1201 TGGTACTATG TTAGCCCCCA TAATTTTTTT TTTCCTTTTA
1241 AAACACTTCC ATAATCTGGA CTCCTCTGTC CAGGCACTGC
1281 TGCCCAGCCT CCAAGCTCCA TCTCCACTCC AGATTTTTTA
1321 CAGCTGCCTG CAGTACTTTA CCTCCTATCA GAAGTTTCTC
1361 AGCTCCCAAG GCTCTGAGCA AATGTGGCTC CTGGGGGTTC
1401 TTTCTTCCTC TGCTGAAGGA ATAAATTGCT CCTTGACATT
1441 GTAGAGCTTC TGGCACTTGG AGACTTGTAT GAAAGATGGC
1481 TGTGCCTCTG CCTGTCTCCC CCACCAGGCT GGGAGCTCTG
1521 CAGAGCAGGA AACATGACTC GTATATGTCT CAGGTCCCTG
1561 CAGGGCCAAG CACCTACCCT CGCTCTTGGC AGGTACTCAG
1601 CGAATGAATG CTGTATATGT TGGGTGCAAA GTTCCCTACT
1641 TCCTGTGACT TCAGCTCTGT TTTACAATAA AATCTTAAAA
1681 TGCC
```

Moreover, the expression of interleukin I receptor antagonist can be monitored by observing the levels of interleukin I receptor antagonist protein in wounds. Interleukin I receptor antagonist protein can be monitored using antibodies or other agents that can selectively bind to interleukin I receptor antagonist. One example of an amino acid sequence for human interleukin I receptor antagonist can be found in the NCBI database at accession number CAA37386 (gi: 32579). See website at ncbi.nlm.nih.gov. This human interleukin I receptor antagonist amino acid sequence is provided below as SEQ ID NO:4.

```
  1  MEICRGLRSH LITLLLFLFH SETICRPSGR KSSKMQAFRI
 41  WDVNQKTFYL RNNQLVAGYL QGPNVNLEEK IDVVPIEPHA
 81  LFLGIHGGKM CLSCVKSGDE TRLQLEAVNI TDLSENRKQD
121  KRFAFIRSDS GPTTSFESAA CPGWFLCTAM EADQPVSLTN
161  MPDEGVMVTK FYFQEDE
```

Moreover, according to the invention, any agent that can increase the expression or activity of interleukin I receptor antagonist can be used to treat wounds, including chronic wounds. Thus, the invention contemplates methods of treating wounds by administering to a subject an agent that can increase the expression or activity of interleukin I receptor antagonist. In some embodiments, the agent that can increase the expression or activity of interleukin I receptor antagonist is an agonist that increases the expression or activity of interleukin I receptor antagonist. Such agonists include, for example, specific anti-inflammatory and anabolic cytokines, such as the interleukin agonists interleukin-4, interleukin-10 and interleukin-13. In other embodiments, interleukin I receptor antagonist can be administered. For example, a human recombinant form of interleukin I receptor antagonist called Anakinra, tradename Kineret™, has recently become available from Amgen (Thousand Oaks, Calif.). See Cohen et al. *Interleukin 1 Receptor Antagonist Anakinra Improves Functional Status in Patients with Rheumatoid Arthritis*, J. Rheumatol. 30:225-31 (2003); Bresnihan et al. *Treatment of rheumatoid arthritis with recombinant human interleukin-1 receptor antagonist*, Arthritis Rheum. 41:2196-2204 (1998). In still other embodiments, interleukin 1 receptor type II (IL-1R type II), available from Immunex, can be administered.

Inositol Triphosphate Receptor 3

According to the invention, the expression of the inositol triphosphate receptor 3 is dramatically reduced in chronic venous stasis leg ulcers from human patients.

Inositol 1,4,5-trisphosphate receptors constitute a family of $Ca^{++}$ channels that release $Ca^{++}$ from intracellular reservoirs in response to inositol triphosphate. Inositol 1,4,5-trisphosphate receptors are encoded by several related genes. Complete cDNA sequences are available for mouse, rat, and *Xenopus* type I Inositol 1,4,5-trisphosphate receptors. Sequences for a human and a *Drosophila* type 3 inositol 1,4,5-trisphosphate receptor are also available.

The levels of inositol triphosphate receptor 3 mRNA can be monitored by any available procedure, including by hybridization, nucleic acid amplification, use of gene expression microarrays and the like. Sequences for inositol triphosphate receptor 3 nucleic acids are available and can be used to obtain probes or primers for detecting inositol triphosphate receptor 3 by these procedures. Thus, for example, sequences for human inositol triphosphate receptor 3 are available in the NCBI database. See website at ncbi.nlm.nih.gov.

One example of a nucleotide sequence for human inositol triphosphate receptor 3 can be found in the NCBI database at accession number NM 002224 (gi: 4504794). See website at ncbi.nlm.nih.gov. This human inositol triphosphate receptor 3 nucleic acid sequence is provided below as SEQ ID NO:5.

```
  1  CGCCCCCCAC GCCCTGGGCC CCGGAGGGCC GCAGCCATGA
 41  GTGAAATGTC CAGCTTTCTT CACATCGGGG ACATCGTCTC
 81  CCTGTACGCC GAGGGCTCCG TCAATGGCTT CATCAGCACT
```

-continued

```
 121 TTGGGGCTGG TGGATGACCG CTGTGTGGTG GAGCCCGCGG
 161 CCGGGGACCT GGACAACCCC CCTAAGAAGT TCCGTGACTG
 201 CCTCTTCAAG GTGTGCCCCA TGAACCGCTA CTCGGCCCAG
 241 AAGCAGTACT GGAAGGCCAA GCAGACTAAG CAGGACAAGG
 281 AGAAGATCGC TGATGTGGTG TTGCTGCAGA AGCTGCAGCA
 321 TGCGGCGCAG ATGGAGCAGA AGCAAAATGA CACGGAGAAC
 361 AAGAAGGTGC ATGGGGATGT CGTGAAGTAT GGCAGTGTGA
 401 TCCAGCTCCT GCACATGAAG AGCAACAAGT ACCTGACAGT
 441 GAACAAGCGG CTTCCGGCCT TGCTGGAGAA GAACGCCATG
 481 CGGGTGACTC TGGATGCCAC AGGCAACGAG GGTTCCTGGC
 521 TCTTCATCCA GCCCTTCTGG AAGCTGCGGA GCAACGGGGA
 561 CAACGTGGTC GTGGGGGACA AGGTGATCCT GAATCCTGTC
 601 AATGCCGGGC AGCCTCTGCA TGCCAGCAAT TACGAGCTCA
 641 GCGACAACGC CGGCTGCAAG GAGGTCAATT CTGTGAACTG
 681 CAACACCAGC TGGAAGATCA ACCTGTTTAT GCAGTTTCGG
 721 GACCACCTGG AGGAGGTGTT GAAAGGGGGA GACGTCGTGC
 761 GGCTGTTCCA TGCGGAGCAG GAGAAGTTCC TGACGTGTGA
 801 CGAGTACAAG GGCAAGCTGC AGGTGTTCCT GCGAACTACA
 841 CTGCGCCAGT CTGCCACCTC GGCCACCAGC TCCAATGCTC
 881 TCTGGGAGGT GGAGGTGGTC CACCACGACC CCTGCCGTGG
 921 AGGAGCTGGG CACTGGAATG GCTTGTACCG CTTCAAGCAC
 961 CTGGCTACAG GCAACTACCT GGCTGCTGAG GAGAACCCCA
1001 GTTACAAAGG TGATGCCTCA GATCCCAAGG CAGCAGGAAT
1041 GGGGGCACAG GGCCGCACAG GCCGCAGGAA TGCTGGGGAG
1081 AAGATCAAGT ACTGCCTGGT GGCTGTGCCT CATGGCAATG
1121 ACATCGCCTC TCTCTTTGAG CTGGACCCCA CCACCTTGCA
1161 GAAAACCGAC TCTTTCGTGC CCCGGAACTC GTACGTCCGG
1201 CTGCGGCACC TCTGCACCAA CACGTGGATT CAGAGCACCA
1241 ATGTGCCCAT TGACATCGAG GAGGAGCGGC CCATCCGGCT
1281 CATGCTGGGC ACCTGCCCCA CCAAGGAGGA CAAGGAGGCC
1321 TTTGCCATCG TGTCAGTGCC CGTGTCTGAG ATCCGAGACC
1361 TGGACTTTGC CAATGACGCC AGCTCCATGC TGGCCAGTGC
1401 CGTGGAGAAA CTCAACGAGG GCTTCATCAG CCAGAATGAC
1441 CGCAGGTTTG TCATCCAGCT GCTGGAAGAC CTGGTGTTCT
1481 TTGTCAGCGA TGTCCCCAAC AATGGGCAGA ATGTCCTGGA
1521 CATCATGGTC ACTAAGCCCA ACCGGGAACG GCAGAAGCTG
1561 ATGAGGGAGC AGAACATCCT CAAACAGGTC TTTGGCATTC
1601 TGAAGGTCCC GTTCCGTGAG AAGGGGGGTG AAGGTCCCCT
1641 GGTGCGGCTG GAGGAGCTGT CAGACCAGAA GAACGCCCCC
1681 TACCAGCACA TGTTCCGCCT GTGCTACCGT GTGTTGCGGT
```

```
1721 ATTCCCAGGA GGACTACCGC AAGAACCAGG AGCACATTGC
1761 CAAGCAGTTT GGGATGATGC AGTCCCAGAT TGGCTACGAC
1801 ATCCTGGCCG AGGACACCAT CACTGCCCTG CTGCACAACA
1841 ACCGCAAGCT CCTGGAAAAG CACATCACCA AGACCGAGGT
1881 GGAGACCTTC GTCAGCCTTG TGCGCAAGAA CCGGGAGCCC
1921 AGGTTCCTGG ACTACCTCTC TGACCTGTGT GTGTCCAACC
1961 ACATCGCCAT CCCCGTCACC AAGAGCTCA TCTGCAAGTG
2001 TGTGCTGGAC CCCAAGAACA GTGACATTCT CATCCGGACC
2041 GAGCTTCGGC CCGTGAAGGA GATGGCCCAA TCCCACGAGT
2081 ACCTGAGCAT CGAGTACTCA AAGAGGAAG TGTGGCTCAC
2121 GTGGACTGAC AAGAATAACG AGCATCATGA AAGAGTGTG
2161 AGGCAGCTGG CCCAGGAGGC GCGGGCCGGC AACGCCCACG
2201 ACGAGAATGT GCTCAGCTAC TACAGGTACC AGCTGAAGCT
2241 CTTTGCCCGC ATGTGCTTGG ACCGCCAGTA CTTGGCCATC
2281 GACGAGATCT CCCAGCAGCT GGGCGTGGAC CTGATTTTCC
2321 TGTGCATGGC AGACGAGATG CTGCCCTTTG ACCTGCGCGC
2361 CTCCTTCTGC CACCTGATGC TCCACGTGCA CGTGGACCGT
2401 GACCCCAGG AGCTGGTCAC GCCGGTCAAG TTTGCCCGTC
2441 TCTGGACTGA GATCCCCACA GCCATCACCA TCAAGGACTA
2481 TGATTCCAAC CTCAACGCGT CCCGAGATGA CAAGAAGAAC
2521 AAGTTTGCCA ACACCATGGA GTTCGTGGAG GACTACCTCA
2561 ACAATGTAGT CAGCGAGGCC GTGCCCTTTG CCAACGAGGA
2601 GAAGAACAAG CTCACTTTTG AGGTGGTCAG CCTGGCGCAC
2641 AATCTCATCT ACTTCGGCTT CTACAGCTTC AGCGAGCTGC
2681 TGCGGCTCAC TCGCACACTG CTGGGCATCA TCGACTGTGT
2721 GCAGGGGCCC CCGGCCATGC TGCAGGCCTA TGAGGACCCC
2761 GGTGGCAAGA ATGTGCGGCG GTCCATCCAG GCGTGGGGC
2801 ACATGATGTC CACCATGGTG CTGAGCCGCA AGCAGTCCGT
2841 CTTCAGTGCC CCCAGCCTGT CTGCTGGGC AGTGCTGCT
2881 GAGCCGCTGG ACAGAAGCAA GTTTGAGGAG AATGAGGACA
2921 TTGTGGTGAT GGAGACCAAG CTGAAGATCC TGGAAATCCT
2961 TCAGTTCATC CTCAACGTCC GCCTGGATTA CCGCATATCC
3001 TACCTGCTGT CTGTCTTCAA GAAGGAGTTT GTGGAGGTGT
3041 TTCCCATGCA GGACAGTGGG GCTGATGCA CAGCCCCTGC
3081 CTTCGACTCT ACCACTGCCA ACATGAACCT GGATCGCATC
3121 GGGGAGCAGG CGGAGGCCAT GTTTGGAGTG GGGAAGACAA
3161 GCAGCATGCT GGAGGTGGAT GACGAGGGCG GCCGCATGTT
3201 CCTGCGCGTG CTCATCCACC TCACCATGCA CGACTATGCG
3241 CCACTCGTCT CGGGTGCCCT GCAGCTGCTC TTCAAGCACT
3281 TCAGCCAGCC CCAGGAGGCC ATGCACACCT TCAAGCAGGT
3321 TCAGCTGCTG ATCTCAGCGC AGGACGTGGA GAACTACAAG
```

-continued

```
3361 GTGATCAAGT CGGAGCTGGA CCGGCTGCGG ACCATGGTGG
3401 AGAAGTCAGA GCTGTGGGTG GACAAGAAGG GCAGTGGCAA
3441 GGGTGAGGAG GTGGAGGCAG GCACCGCCAA GGACAAGAAA
3481 GAGCGTCCCA CGGACGAGGA GGGCTTTCTG CACCCACCAG
3521 GGGAGAAAAG CAGTGAGAAC TACCAGATCG TCAAGGGCAT
3561 CCTGGAAAGG CTGAACAAGA TGTGCGGGGT TGGGGAGCAA
3601 ATGAGGAAGA AGCAGCAACG GCTGCTGAAG AACATGGATG
3641 CCCACAAGGT CATGCTGGAC CTGCTGCAGA TCCCCTATGA
3681 CAAGGGTGAT GCCAAGATGA TGGAGATCCT GCGCTACACG
3721 CACCAGTTCC TGCAGAAGTT CTGTGCAGGG AACCCCGGCA
3761 ACCAGGCCCT GCTGCACAAA CACCTGCACC TCTTCCTCAC
3801 GCCAGGGCTC CTGGAGGCAG AGACCATGCA GCACATCTTC
3841 CTGAACAACT ATCAGCTCTG CTCCGAGATC AGCGAGCCTG
3881 TGTTGCAGCA CTTCGTGCAC CTGCTGGCCA CGCACGGGCG
3921 CCATGTGCAG TACCTGGACT TCCTGCACAC CGTCATTAAG
3961 GCCGAGGGCA AGTACGTCAA GAAGTGCCAG GACATGATCA
4001 TGACTGAGCT GACCAATGCA GGTGACGATG TGGTCGTGTT
4041 CTACAATGAT AAGGCATCGC TGGCCCACCT GCTGGACATG
4081 ATGAAGGCCG CCCGCGACGG CGTGGAGGAC CACAGCCCCC
4121 TCATGTACCA CATTTCCCTG GTGGACCTGC TGGCCGCCTG
4161 TGCCGAGGGC AAAAACGTCT ACACTGAGAT CAAGTGCACC
4201 TCCCTCGTGC CGCTGGAGGA CGTGGTGTCT GTGGTGACGC
4241 ATGAGGACTG CATCACTGAG GTGAAAATGG CCTATGTGAA
4281 CTTCGTGAAC CACTGGTACG TGGACACGGA GGTGGAGATG
4321 AAGGAGATCT ACACCAGCAA CCACATCTGG ACGCTCTTTG
4361 AGAACTTCAC CCTGGACATG GCTCGGGTCT GCAGCAAGCG
4401 TGAGAAGCGC GTGGCTGACC CCACCTTGGA GAAGTACGTG
4441 CTGAGCGTTG TGCTGGACAC CATCAACGCC TTCTTCAGCT
4481 CCCCATTCTC TGAGAACAGC ACTTCCCTGC AGACACACCA
4521 GCCGGTTGTG GTGCAGCTGC TGCAGTCTAC CACACGCCTC
4561 CTCGAGTGTC CGTGGCTACA GCAGCAGCAC AAGGGCTCCG
4601 TGGACGCCTG CATCCGGACC CTCGCCATGG TGGCCAAGGG
4641 CCGGGCCATC TTGCTGCCCA TGGACCTGGA TGCCCACATC
4681 AGCTCGATGC TCAGCAGTGC AGCCAGCTGT GCAGCTGCCG
4721 CCCACCGGAA CGCCTCCAGC TACAAGGCAA CCACGCGGGC
4761 CTTCCCCCGC GTCACCCCCA CCGCCAACCA GTGGGACTAC
4801 AAGAACATCA TTGAGAAGCT GCAGGACATC ATCACAGCCC
4841 TGGAGGAGCG GCTGAAGCCC CTGGTACAGG CTGAGCTGTC
4881 CGTGCTGGTG GATGTCCTGC ACTGGCCTGA GCTGCTCTTC
4921 CTGGAGGGCA GTGAGGCCTA CCAGCGCTGC GAGAGTGGGG
4961 GCTTCCTGTC CAAGCTGATC CAGCACACCA AGGACCTCAT
5001 GGAGTCGGAG GAGAAGCTGT GCATCAAGGT GCTGCGGACC
5041 CTGCAGCAGA TGCTCGTCAA GAAGACCAAG TACGGGGACC
5081 GGGGCAACCA GCTGCGCAAG ATGCTGCTGC AAAACTACCT
5121 CCAGAACCGG AAGTCCACCT CGCGGGGGGA CCTTCCCGAC
5161 CCCATAGGCA CTGGCCTGGA CCCAGACTGG TCGGCAATCG
5201 CAGCCACCCA GTGCCGGCTG ACAAGGAGG GGGCCACCAA
5241 GTTGGTATGC GACCTCATCA CCAGCACCAA GAACGAGAAG
5281 ATCTTCCAGG AGAGCATCGG CCTGGCCATC CACCTGCTGG
5321 ATGGTGGCAA CACAGAGATC CAGAAATCCT TCCACAACCT
5361 GATGATGAGT GACAAGAAGT CAGAGCGCTT CTTCAAGGTG
5401 CTGCACGACC GCATGAAGCG GGCCCAGCAG AGACCAAGT
5441 CCACGGTGGC AGTCAACATG AATGACCTGG GCAGCCAGCC
5481 ACATGAGGAC CGCGAGCCAG TCGACCCCAC CACCAAAGGC
5521 CGCGTGGCCT CCTTCTCGAT ACCTGGCTCC TCATCCCGCT
5561 ACTCGCTGGG CCCCAGCCTG CGCCGGGGGC ACGAGGTGAG
5601 CGAACGTGTG CAGAGCAGTG AGATGGGCAC ATCCGTGCTC
5641 ATCATGCAGC CCATCCTGCG CTTTCTGCAG CTGCTGTGTG
5681 AGAACCACAA CCGGGACCTG CAGAACTTCC TGCGCTGTCA
5721 GAACAACAAA ACCAACTACA ACTTGGTATG CGAGACGCTG
5761 CAGTTCCTGG ACATCATGTG CGGCAGCACC ACGGGCGGCC
5801 TGGGGCTGCT GGGGCTCTAC ATCAATGAGG ACAACGTGGG
5841 CCTCGTCATC CAGACCTTGG AGACCCTCAC TGAGTACTGC
5881 CAGGGCCCCT GCCATGAGAA CCAGACTTGC ATTGTGACTC
6021 ACGAGTCCAA TGGCATAGAC ATCATCACCG CACTGATCCT
6061 CAATGACATC AGCCCCCTGT GCAAGTACCG CATGGATCTG
6001 GTGCTGCAGC TCAAGGACAA TGCCTCCAAG CTGCTCCTGG
6041 CTCTGATCGA GAGCCGGCAT GACAGTGAAA ATGCTGAGCG
6081 AATCCTCATC AGCCTGCGGC CCCAGGAGCT GGTGGACGTC
6121 ATCAAGAAGG CCTACCTGCA GGAGGAAGAG CGTGAGAACT
6161 CGGAGGTGAG CCCCACGTGAA GTGGGCCATA ACATCTATAT
6201 CCTCGCGCTG CAGCTCTCCA GGCACAATAA ACAGCTGCAG
6241 CACCTGCTGA AGCGGTGAA GCGCATTCAA GAGGAGGAGG
6281 CCGAGGGTAT CTCTTCCATG CTCAGCCTCA CAACAAGCA
6321 GCTGTCACAG ATGCTCAAGT CCTCAGCGCC AGCACAGGAG
6361 GAGGAGGAAG ACCCCCTGGC CTACTATGAG AACCACACGT
6401 CCCAGATCGA GATTGTGCGG CAGGACCGCA GCATGGAGCA
6441 GATCGTGTTC CCAGTGCCCG GCATCTGCCA GTTCCTGACG
6481 GAGGAAACCA AGCACCGGCT CTTCACCACT ACTGAGCAGG
6521 ACGAGCAGGG CAGCAAAGTG AGCGACTTCT TCGACCAGTC
6561 CTCCTTCCTG CACAACGAGA TGGAGTGGCA GCGCAACGTC
```

-continued

```
6601 CGCAGCATGC CGCTGATCTA CTGGTTCTCC CGCCGCATGA
6641 CCCTGTGGGG CAGCATCTCC TTCAACCTGG CCGTGTTTAT
6681 CAACATCATC ATTGCCTTCT TCTACCCTTA CATGGAGGGC
6721 GCGTCCACAG GCGTGCTGGA CTCCCCTCTC ATCTCATTGC
6761 TCTTCTGGAT CCTCATCTGC TTCTCCATCG CGGCCCTGTT
6801 CACCAAGCGC TACAGCATCC GCCCCCTCAT CGTGGCGCTC
6841 ATCCTGCGCT CCATCTACTA TCTGGGCATC GGGCCCACAC
6881 TCAACATCCT GGGTGCCCTC AATCTGACCA ACAAGATCGT
6921 GTTTGTGGTG AGCTTCGTGG GCAACCGTGG CACCTTCATC
6961 CGGGGCTATA AGGCCATGGT CATGGACATG GAATTCCTCT
7001 ACCACGTGGG CTACATCCTG ACCAGTGTCC TGGGCCTCTT
7041 TGCTCATGAG CTGTTCTACA GCATCCTGCT CTTTGACCTC
7081 ATCTACCGCG AGGAGACGCT GTTCAACGTC ATCAAGAGTG
7121 TGACCCGCAA TGGCCGCTCC ATCCTGCTGA CAGCCCTGCT
7161 GGCCCTCATC CTGGTCTACC TCTTCTCCAT CGTCGGCTTC
7201 CTCTTCCTCA AGGATGACTT CATTCTCGAG GTCGACCGGC
7241 TGCCCAACAA CCACTCCACA GCCAGCCCCC TGGGGATGCC
7281 ACATGGAGCT GCTGCATTTG TGGACACCTG CAGTGGGGAC
7321 AAGATGGACT GTGTCTCAGG GCTCTCGGTG CCTGAGGTCC
7361 TGGAAGAGGA CAGGGAGCTG GACAGCACAG AGCGGGCCTG
7401 TGACACTCTG TTGATGTGCA TCGTCACTGT CATGAACCAT
7441 GGGCTACGCA ACGGTGGTGG CGTGGGCGAC ATTCTCCGCA
7481 AGCCCTCCAA AGATGAGTCT CTCTTCCCAG CCCGAGTGGT
7521 CTATGACCTC TGTTCTTCT TCATCGTCAT CATCATTGTG
7561 CTGAACCTCA TCTTTGGGGT AATCATCGAC ACCTTCGCTG
7601 ACCTGCGTAG TGAGAAGCAG AAGAAGGAGG AGATTCTTAA
7641 GACGACATGC TTCATCTGTG GTCTGGAGAG GGACAAGTTT
7681 GATAACAAGA CAGTGTCATT TGAGGAACAC ATCAAGCTGG
7721 AGCACAACAT GTGGAACTAC TTGTACTTCA TTGTGCTGGT
7761 CCGCGTGAAG AACAAGACCG ACTACACGGG CCCTGAGAGC
7801 TACGTGGCCC AGATGATCAA GAACAAGAAC CTGGACTGGT
7841 TCCCCCGGAT GCGGGCCATG TCCCTTGTCA GCAATGAGGG
7881 CGAGGGGGAG CAGAATGAGA TTCGGATTCT CCAGGACAAG
7921 CTCAACTCCA CCATGAAGCT GGTGTCCCAC CTCACTGCCC
7961 AGCTCAACGA GCTCAAGGAG CAGATGACGG AGCAGCGGAA
8001 ACGCAGGCAA CGCCTAGGCT TTGTGGATGT CCAGAACTGC
8041 ATTAGCCGCT GAGGAGAGCC ACCGAAGGCC CAACAGGGG
8081 ATGCTCATCA CTGGAGACTG CGACTGGGAA GAACACTGCC
8121 CCCTCCCTCG GGTTGGGTGG CCCAGCCAGC TGGCCAGCCT
8161 CCACTCCCAC TCTGCCAGAC ACCCTGACAC CCACCCAGGC
8201 TTTGAAGAGC ATGGAGGGGG AGCCTCAGAG CTGACAGTCC
8241 TGCTTAGAGC CCTTAAAAAG ACTTGAAAGT TCACTGGGAC
8281 TCAGTTTACC TTAATGCCTT AGCAGAAGAT AAATCCTACC
8321 TAGAGACCTT TGTTCCTTAA AGCAATAACT GACAACTCTT
8361 TGTAGTCCTC CTTGTGGGTA GTTAAGAGTG GGGTCACCCC
8401 TTTAACTCCA AGCACTACAT TTTGGCGGCT GCGGCCTCTG
8441 CGGGAGGTGG CAGTTATGCT GTTACTAGTG ATTTTAGGGC
8481 TTTGTTATTT AACTTATTTC AAGGGTGCTG TGCTCAGCCC
8521 TGCCCATGGC TGTGCAGCTC CCTCCGTGCC TCAGATCTGC
8561 TGTAGCCAGT GCAGACCTCA CTGTCGTGTC CATGCCACCC
8601 CCGGCATGGC TCCAGGTGGC CTGGTGACTC CATGATGGAC
8641 GATCTTGCTC CCAGGACCTG CCTCTTCCCA GGCTTCCTGG
8681 GGAAGAGTTG TACGCCCAGG CAACAAGGGC TGAGCTGCGC
8721 TTGCGTGGCT GTTTCATGAC CGCTTGTTTT TCTCCTTTTG
8761 GTGTAATGTT TTACAAATCC TTTGGCCTGA GAACTAATAT
8801 GTTAATTGCC TTAATAAAT TAATAGAAAT CTA
```

Moreover, the expression of inositol triphosphate receptor 3 can be monitored by observing the levels of inositol triphosphate receptor 3 protein in wounds. For example, inositol triphosphate receptor 3 protein can be monitored using antibodies or other agents that can selectively bind to inositol triphosphate receptor 3. One example of an amino acid sequence for human inositol triphosphate receptor 3 can be found in the NCBI database at accession number NP 002215 (gi: 4504795). See website at ncbi.nlm.nih.gov. This human inositol triphosphate receptor 3 amino acid sequence is provided below as SEQ ID NO:6.

```
  1 MSEMSSFLHI GDIVSLYAEG SVNGFISTLG LVDDRCVVEP
 41 AAGDLDNPPK KFRDCLFKVC PMNRYSAQKQ YWKAKQTKQD
 81 KEKIADVVLL QKLQHAAQME QKQNDTENKK VHGDVVKYGS
121 VIQLLHMKSN KYLTVNKRLP ALLEKNAMRV TLDATGNEGS
161 WLFIQPFWKL RSNGDNVVVG DKVILNPVNA GQPLHASNYE
201 LSDNAGCKEV NSVNCNTSWK INLFMQFRDH LEEVLKGGDV
241 VRLFHAEQEK FLTCDEYKGK LQVFLRTTLR QSATSATSSN
281 ALWEVEVVHH DPCRGGAGHW NGLYRFKHLA TGNYLAAEEN
321 PSYKGDASDP KAAGMGAQGR TGRRNAGEKI KYCLVAVPHG
361 NDIASLFELD PTTLQKTDSF VPRNSYVRLR HLCTNTWIQS
401 TNVPIDIEEE RPIRLMLGTC PTKEDKEAFA IVSVPVSEIR
441 DLDFANDASS MLASAVEKLN EGFISQNDRR FVIQLLEDLV
481 FFVSDVPNNG QNVLDIMVTK PNRERQKLMR EQNILKQVFG
521 ILKVPFREKG GEGPLVRLEE LSDQKNAPYQ HMFRLCYRVL
561 RYSQEDYRKN QEHIAKQFGM MQSQIGYDIL AEDTITALLH
601 NNRKLLEKHI TKTEVETFVS LVRKNREPRF LDYLSDLCVS
641 NHIAIPVTQE LICKCVLDPK NSDILIRTEL RPVKEMAQSH
```

```
 681 EYLSIEYSEE EVWLTWTDKN NEHHEKSVRQ LAQEARAGNA

721 HDENVLSYYR YQLKLFARMC LDRQYLAIDE ISQQLGVDLI

761 FLCMADEMLP FDLRASFCHL MLHVHVDRDP QELVTPVKFA

801 RLWTEIPTAI TIKDYDSNLN ASRDDKKNKF ANTMEFVEDY

841 LNNVVSEAVP FANEEKNKLT FEVVSLAHNL IYFGFYSFSE

881 LLRLTRTLLG IIDCVQGPPA MLQAYEDPGG KNVRRSIQGV

921 GHMMSTMVLS RKQSVFSAPS LSAGASAAEP LDRSKFEENE

961 DIVVMETKLK ILEILQFILN VRLDYRISYL LSVFKKEFVE

1001 VFPMQDSGAD GTAPAFDSTT ANMNLDRIGE QAEAMFGVGK

1041 TSSMLEVDDE GGRMFLRVLI HLTMHDYAPL VSGALQLLFK

1081 HFSQRQEAMH TFKQVQLLIS AQDVENYKVI KSELDRLRTM

1121 VEKSELWVDK KGSGKGEEVE AGTAKDKKER PTDEEGFLHP

1161 PGEKSSENYQ IVKGILERLN KMCGVGEQMR KKQQRLLKNM

1201 DAHKVMLDLL QIPYDKGDAK MMEILRYTHQ FLQKFCAGNP

1241 GNQALLHKHL HLFLTPGLLE AETMQHIFLN NYQLCSEISE

1281 PVLQHFVHLL ATHGRHVQYL DFLHTVIKAE GKYVKKCQDM

1321 IMTELTNAGD DVVVFYNDKA SLAHLLDMMK AARDGVEDHS

1361 PLMYHISLVD LLAACAEGKN VYTEIKCTSL VPLEDVVSVV

1401 THEDCITEVK MAYVNFVNHC YVDTEVEMKE IYTSNHIWTL

1441 FENFTLDMAR VCSKREKRVA DPTLEKYVLS VVLDTINAFF

1481 SSPFSENSTS LQTHQPVVVQ LLQSTTRLLE CPWLQQQHKG

1521 SVEACIRTLA MVAKGRAILL PMDLDAHISS MLSSGASCAA

1561 AAQRNASSYK ATTRAFPRVT PTANQWDYKN IIEKLQDIIT

1601 ALEERLKPLV QAELSVLVDV LHWPELLFLE GSEAYQRCES

1641 GGFLSKLIQH TKDLMESEEK LCIKVLRTLQ QMLVKKTKYG

1681 DRGNQLRKML LQNYLQNRKS TSRGDLPDPI GTGLDPDWSA

1721 IAATQCRLDK EGATKLVCDL ITSTKNEKIF QESIGLAIHL

1761 LDGGNTEIQK SFHNLMMSDK KSERFFKVLH DRMKRAQQET

1801 KSTVAVNMND LGSQPHEDRE PVDPTTKGRV ASFSIPGSSS

1841 RYSLGPSLRR GHEVSERVQS SEMGTSVLIM QPILRFLQLL

1881 CENHNRDLQN FLRCQNNKTN YNLVCETLQF LDIMCGSTTG

1921 GLGLLGLYIN EDNVGLVIQT LETLTEYCQG PCHENQTCIV

1961 THESNGIDII TALILNDISP LCKYRMDLVL QLKDNASKLL

2001 LALMESRHDS ENAERILISL RPQELVDVIK KAYLQEEERE

2041 NSEVSPREVG HNIYILALQL SRHNKQLQHL LKPVKRIQEE

2081 EAEGISSMLS LNNKQLSQML KSSAPAQEEE EDPLAYYENH

2121 TSQIEIVRQD RSMEQIVFPV PGICQFLTEE TKHRLFTTTE

2161 QDEQGSKVSD FFDQSSFLHN EMEWQRNVRS MPLIYWFSRR

2201 MTLWGSISFN LAVFINIIIA FFYPYMEGAS TGVLDSPLIS

2241 LLFWILICFS IAALFTKRYS IRPLIVALIL RSIYYLGIGP

2281 TLNILGALNL TNKIVFVVSF VGNRGTFIRG YKAMVMDMEF

2321 LYHVGYILTS VLGLFAHELF YSILLFDLIY REETLFNVIK

2361 SVTRNGRSIL LTALLALILV YLFSIVGFLF LKDDFILEVD

2401 RLPNNHSTAS PLGMPHGAAA FVDTCSGDKM DCVSGLSVPE

2441 VLEEDRELDS TERACDTLLM CIVTVMNHGL RNGGGVGDIL

2481 RKPSKDESLF PARVVYDLLF FFIVIIIVLN LIFGVIIDTF

2521 ADLRSEKQKK EEILKTTCFI CGLERDKFDN KTVSFEEHIK

2561 LEHNMWNYLY FIVLVRVKNK TDYTGPESYV AQMIKNKNLD

2601 WFPRMRAMSL VSNEGEGEQN EIRILQDKLN STMKLVSHLT

2641 AQLNELKEQM TEQRKRRQRL GFVDVQNCIS R
```

Interleukins

According to the invention, the expression of certain interleukins is increased in chronic venous stasis leg ulcers from human patients. For example, the expression of interleukin 1 beta and interleukin 8 is increased in chronic wounds.

The levels of interleukin mRNA can be monitored by any available procedure, including by hybridization, nucleic acid amplification, use of gene expression microarrays and the like. Sequences for numerous interleukin nucleic acids are available and can be used to obtain probes or primers for detecting interleukin expression by these procedures. Thus, for example, sequences for numerous human interleukin genes are available in the NCBI database. See website at ncbi.nlm.nih.gov. Moreover, the expression of interleukins can be monitored by observing the levels of interleukin proteins in wounds. For example, interleukin protein expression can be monitored using antibodies or other agents that can selectively bind to interleukin. Examples of numerous interleukin amino acid sequences can be found in the NCBI database. See website at ncbi.nlm.nih.gov. These sequences can be used for developing antibody preparations that can bind human interleukins.

For example, an amino acid sequence for human interleukin1 beta can be found in the NCBI database at accession number CAG28607 (gi: 47115295). A nucleotide sequence for this human interleukin 1 beta protein can be found in the NCBI database at accession number CR407679 (gi: 47115294). See website at ncbi.nlm.nih.gov.

An amino acid sequence for human interleukin 8 precursor can be found in the NCBI database at accession number AAH 13615.1 (gi: 15488984). A nucleotide sequence for this human interleukin 8 protein can be found in the NCBI database at accession number BC013615 (gi: 15488983). See website at ncbi.nlm.nih.gov.

Growth Factors

According to the invention, the expression of certain growth factors is increased in chronic venous stasis leg ulcers from human patients. For example, the expression of transforming growth factor, beta-induced (TGFBI) is increased in chronic wounds.

The levels of growth factor mRNA can be monitored by any available procedure, including by hybridization, nucleic acid amplification, use of gene expression microarrays and the like. Sequences for numerous growth factor nucleic acids are available and can be used to obtain probes or primers for detecting growth factor expression by these procedures. Thus, for example, sequences for numerous human growth factor genes are available in the NCBI database. See website at ncbi.nlm.nih.gov. Moreover, the expression of growth factors can be monitored by observing the levels of growth factor proteins in wounds. For example, growth factor protein expression can be monitored using antibodies or other agents that can selectively bind to a specific growth factor. Examples of numerous growth factor amino acid sequences can be found in the NCBI database. See website at ncbi.nlm.nih.gov. These sequences can be used for developing antibody preparations that can bind human interleukins.

For example, an amino acid sequence for human TGFBI can be found in the NCBI database at accession number AAH69207 (gi: 46623331). A nucleotide sequence for this human interleukin 1, beta protein can be found in the NCBI database at accession number BC069207 (gi: 46623330). See website at ncbi.nlm.nih.gov.

Collagen

According to the invention, the expression of various collagens is increased in chronic venous stasis leg ulcers from human patients. For example, the expression of collagen, type I, alpha 1, collagen, type I, alpha 2, collagen, type III, alpha 1, collagen, type IV, alpha 1, collagen, type VI, alpha 1, collagen, type VI, alpha 2 and collagen, type XV, alpha 1 is increased in chronic wounds.

The levels of collagen mRNA can be monitored by any available procedure, including by hybridization, nucleic acid amplification, use of gene expression microarrays and the like. Sequences for numerous collagen nucleic acids are available and can be used to obtain probes or primers for detecting collagen expression by these procedures. Thus, for example, sequences for numerous human collagen genes are available in the NCBI database. See website at ncbi.nlm.nih.gov. Moreover, the expression of collagen can be monitored by observing the levels of collagen protein in wounds. For example, collagen protein expression can be monitored using antibodies or other agents that can selectively bind to collagen. Examples of numerous collagen amino acid sequences can be found in the NCBI database. See website at ncbi.nlm.nih.gov. These sequences can be used for developing antibody preparations that can bind human collagen.

For example, an amino acid sequence for human collagen, type I, alpha I preproprotein can be found in the NCBI database at accession number AAH36531 (gi: 22328092). A nucleotide sequence for this human collagen, type I, alpha 1 preproprotein can be found in the NCBI database at accession number BC036531 (gi: 34193787). See website at ncbi.nlm.nih.gov.

An amino acid sequence for human collagen, type I, alpha 2 can be found in the NCBI database at accession number AAH42586.1 (gi: 45708783). A nucleotide sequence for this human collagen, type I, alpha 2 protein can be found in the NCBI database at accession number BC042586 (gi: 45708782). See website at ncbi.nlm.nih.gov.

An amino acid sequence for human collagen, type III, alpha 1 can be found in the NCBI database at accession number AAA52003 (gi: 180416). A nucleotide sequence for this human collagen, type III, alpha I protein can be found in the NCBI database at accession number M13146 (gi: 180415). See website at ncbi.nlm.nih.gov.

An amino acid sequence for human collagen, type IV, alpha I can be found in the NCBI database at accession number AAA53098 (gi: 180803). A nucleotide sequence for this human collagen, type IV, alpha 1 protein can be found in the NCBI database at accession number AH002741 (gi: 180801). See website at ncbi.nlm.nih.gov.

An amino acid sequence for human collagen, type VI, alpha 1 precursor can be found in the NCBI database at accession number AAH52575 (gi: 30851190). A nucleotide sequence for this human collagen, type VI, alpha 1 protein can be found in the NCBI database at accession number BC052575 (gi: 30851189). See website at ncbi.nlm.nih.gov.

An amino acid sequence for human collagen, type VI, alpha 2 precursor can be found in the NCBI database at accession number AAB20836 (gi: 242005). A nucleotide sequence for this human collagen, type VI, alpha 2 protein can be found in the NCBI database at accession number AH003819 (gi: 1680103). See website at ncbi.nlm.nih.gov.

An amino acid sequence for human collagen, type XV, alpha 1 can be found in the NCBI database at accession number AAA58429 (gi: 461397). A nucleotide sequence for this human collagen, type XV, alpha 1 protein can be found in the NCBI database at accession number L25286 (gi: 461396). See website at ncbi.nlm.nih.gov.

Amplification and/or Hybridization Assays

According to the invention, the expression of angiotensin II receptor, interleukin I receptor antagonist, and/or inositol triphosphate receptor 3 are reduced in chronic wounds. Moreover, the expression levels of interleukins, growth factors and collagens are increased in chronic wound tissues. Accordingly, the invention provides a method for monitoring a chronic wound by observing angiotensin II receptor, interleukin I receptor antagonist, inositol triphosphate receptor 3, interleukin, growth factor and/or collagen gene expression levels in a wound tissue sample.

The expression levels of angiotensin II receptor, interleukin I receptor antagonist, inositol triphosphate receptor 3, interleukins, growth factors and/or collagens can be monitored by detecting either the RNA or protein levels produced by these genes. Assays for angiotensin II receptor, interleukin I receptor antagonist, inositol triphosphate receptor 3, interleukin, growth factor and/or collagen expression can be performed separately or simultaneously. A number of methods for detecting and/or quantifying the expression level of an RNA or protein in a tissue sample are available in the art and can be employed in the practice of this aspect of the invention. Any available assay procedure for RNA or protein can be utilized.

For example, hybridization assays including Northern blotting techniques, hybridization to oligonucleotide probe arrays, oligonucleotide probe microarrays, in situ hybridization, nucleic acid amplification (e.g., reverse transcriptase-polymerase chain reaction, RT-PCR) and other analytical procedures can be employed.

In order to measure the expression levels of various genes in a sample, it is desirable to provide a nucleic acid sample obtained from a suitable source (e.g. a wound) for such analysis. Where it is desired that the nucleic acid concentration, or differences in nucleic acid concentration between different samples, reflect transcription levels or differences in transcription levels of a gene or genes, it is desirable to provide a nucleic acid sample comprising mRNA transcript(s) of the gene or genes, or nucleic acids derived from the mRNA transcript(s). As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, suitable samples include, but are not limited to, mRNA transcripts of the gene or genes of interest, cDNA reverse transcribed from the mRNA, cRNA transcribed from the cDNA, DNA amplified from the genes, RNA transcribed from amplified DNA, and the like.

When quantifying the transcription level (and thereby expression) of a one or more genes in a sample, the nucleic acid sample is one in which the concentration of the mRNA transcript(s) of the gene or genes, or the concentration of the nucleic acids derived from the mRNA transcript(s), is proportional to the transcription level (and therefore expression level) of that gene. Thus, the hybridization signal intensity obtained by a selected assay technique should be proportional to the amount of hybridized nucleic acid. While it is preferred that the proportionality be relatively strict (e.g., a doubling in transcription rate results in a doubling in mRNA transcript in the sample nucleic acid pool and a doubling in hybridization signal), one of skill will appreciate that the proportionality can be more relaxed and even non-linear. Thus, for example, an assay where a 5 fold difference in concentration of the target mRNA results in a 3 to 6 fold difference in hybridization intensity is sufficient for most purposes. Where more precise quantification is required appropriate controls can be run to correct for variations introduced in sample preparation and hybridization as described herein. In addition, serial dilutions of "standard" target mRNAs can be used to prepare calibration curves according to methods well known to those of skill in the art.

In some embodiments, the nucleic acid sample is the total mRNA or a total cDNA isolated and/or otherwise derived from a biological sample. The term "biological sample", as used herein, refers to a sample obtained from an organism. The sample may be of any biological tissue or fluid, for example, a wound tissue sample or a wound exudate sample. Frequently the sample will be a "clinical sample" which is a sample derived from a patient. Such samples include, but are not limited to, tissue or fine needle biopsy samples, skin scrapings or cells therefrom. Biological samples may also include sections of tissues such as frozen sections taken for histological purposes.

The nucleic acid (for example, mRNA) may be isolated from the sample according to any of a number of methods well known to those of skill in the art. Methods of isolating total mRNA are well known to those of skill in the art. For example, methods of isolation and purification of nucleic acids are described in detail in Chapter 3 of Laboratory Techniques in Biochemistry and Molecular Biology: Hybridization With Nucleic Acid Probes, Part I. Theory and Nucleic Acid Preparation, P. Tijssen, ed. Elsevier, N.Y. (1993) and Chapter 3 of Laboratory Techniques in Biochemistry and Molecular Biology: Hybridization With Nucleic Acid Probes, Part I. Theory and Nucleic Acid Preparation, P. Tijssen, ed. Elsevier, N.Y. (1993)).

In some embodiments, the total nucleic acid is isolated from a given sample using, for example, an acid guanidinium-phenol-chloroform extraction method and polyA$^+$ mRNA is isolated by oligo dT column chromatography or by using (dT)$_n$ magnetic beads (see, e.g., Sambrook et al., Molecular Cloning: A Laboratory Manual (2nd ed.), Vols. 1-3, Cold Spring Harbor Laboratory, (1989), or Current Protocols in Molecular Biology, F. Ausubel et al., ed. Greene Publishing and Wiley-Interscience, New York (1987)).

Frequently, it is desirable to amplify the nucleic acid sample prior to hybridization. One of skill in the art will appreciate that whatever amplification method is used, if a quantitative result is desired, care must be taken to use a method that maintains or controls for the relative frequencies of the amplified nucleic acids.

Methods of "quantitative" amplification are well known to those of skill in the art. For example, quantitative PCR involves simultaneously co-amplifying a known quantity of a control RNA or DNA using the same primers. This provides an internal standard that may be used to calibrate the PCR reaction. A hybridization assay or other type of assay is subsequently employed to detect the control RNA or DNA as an internal standard, thereby permitting quantification of the extent of amplification.

For example, one internal standard that can be used is a synthetic AW106 cRNA. The AW106 cRNA is combined with RNA isolated from the sample according to standard techniques known to those of skill in the art. The RNA is then reverse transcribed using a reverse transcriptase to provide copy DNA. The cDNA sequences are then amplified (e.g., by PCR) using labeled primers. The amplification products are separated, typically by electrophoresis, and the amount of radioactivity (proportional to the amount of amplified product) is determined. The amount of mRNA in the sample is then calculated by comparison with the signal produced by the known AW106 RNA standard. Detailed protocols for quantitative PCR are provided in PCR Protocols, A Guide to Methods and Applications, Innis et al., Academic Press, Inc. N.Y., (1990).

Other suitable amplification methods include, but are not limited to polymerase chain reaction (PCR) (Innis, et al., PCR Protocols. A guide to Methods and Application. Academic Press, Inc. San Diego, (1990)), ligase chain reaction (LCR) (see Wu and Wallace, Genomics, 4: 560 (1989), Landegren, et al., Science, 241: 1077 (1988) and Barringer, et al., Gene, 89: 117 (1990), transcription amplification (Kwoh, et al., Proc. Natl. Acad. Sci. USA, 86: 1173 (1989)), and self-sustained sequence replication (Guatelli, et al., Proc. Nat. Acad. Sci. USA, 87: 1874 (1990)).

In some embodiments, the sample mRNA is reverse transcribed with a reverse transcriptase and an oligo dT primer to provide single stranded cDNA.

Sometimes the primer also has a sequence encoding a phage T7 or T3 promoter to permit RNA transcription from the cDNA. The second DNA strand is polymerized using a DNA polymerase. After synthesis of double-stranded cDNA, T7 or T3 RNA polymerase can be added to transcribe RNA from the cDNA template. Successive rounds of transcription from each single cDNA template result in amplified RNA. Methods of in vitro polymerization are available to those of skill in the art (see, e.g., Sambrook, supra.) and this particular method is described in detail by Van Gelder, et al., Proc. Natl. Acad. Sci. USA, 87: 1663-1667 (1990) who demonstrate that in vitro amplification according to this method preserves the relative frequencies of the various RNA transcripts. Moreover, Eberwine et al. Proc. Natl. Acad. Sci. USA, 89: 3010-3014 provide a protocol that uses two rounds of amplification via in vitro transcription to achieve greater than $10^6$ fold amplification of the original starting material thereby permitting expression monitoring even where biological samples are limited.

It will be appreciated by one of skill in the art that the direct transcription method described above provides an antisense (aRNA) pool. Where antisense RNA is used as the nucleic acid to be detected (the target nucleic acid), a hybridization probe or probes are chosen to be complementary to subsequences of the antisense nucleic acids. Conversely, where the target nucleic acid pool is a pool of sense nucleic acids, the probe(s) is/are selected to be complementary to subsequences of the sense nucleic acids. Finally, where the nucleic acid pool is double stranded, the probes may be of either sense as the target nucleic acids include both sense and antisense strands.

The protocols cited above include methods of generating pools of either sense or antisense nucleic acids. Indeed, one approach can be used to generate either sense or antisense nucleic acids as desired. For example, the cDNA can be directionally cloned into a vector (e.g., Stratagene's p Bluscript II KS (+) phagemid) such that it is flanked by the T3 and T7 promoters. In vitro transcription with the T3 polymerase will produce RNA of one sense (the sense depending on the orientation of the insert), while in vitro transcription with the T7 polymerase will produce RNA having the opposite sense. Other suitable cloning systems include phage lambda vectors designed for Cre-loxP plasmid subcloning (see e.g., Palazzolo et al., Gene, 88: 25-36 (1990)). In some embodiments, a high activity RNA polymerase (e.g. about 2500 units/μL for T7, available from Epicentre Technologies) is used.

The invention therefore provides a method of quantifying an RNA expression level of an angiotensin II receptor, interleukin I receptor antagonist, inositol triphosphate receptor 3, interleukin, growth factor or collagen gene in a tissue sample by quantitatively generating a cDNA from RNA obtained from the tissue sample, amplifying the cDNA and detecting how much angiotensin II receptor, interleukin I receptor antagonist, inositol triphosphate receptor 3, interleukin, growth factor or collagen cDNA is amplified relative to an internal standard.

This method for detecting mRNA levels in a biological sample therefore comprises producing cDNA from an RNA sample by reverse transcription using at least one primer; amplifying the cDNA so produced using sense and antisense primers to amplify the cDNAs therein; and detecting the presence of the amplified cDNA.

Any number of appropriate sense and antisense primers can be designed from a nucleotide sequence and used for this purpose. For example, such primers can be selected from nucleic acid sequences for angiotensin II receptor, interleukin I receptor antagonist, inositol triphosphate receptor 3, interleukin, growth factor or collagen genes. In some embodiments, primers for angiotensin II receptor, interleukin I receptor antagonist, or inositol triphosphate receptor 3 are selected from SEQ ID NO:1, SEQ ID NO:3, or SEQ ID NO:5, respectively.

In many embodiments, primers for amplification of angiotensin II receptor, interleukin I receptor antagonist, inositol triphosphate receptor 3, interleukin, growth factor or collagen nucleic acids are selected so that those primers will hybridize selectively to an RNA transcribed from an angiotensin II receptor, interleukin I receptor antagonist, inositol triphosphate receptor 3, interleukin, growth factor or collagen gene. Similarly, probes used for detection of angiotensin II receptor, interleukin I receptor antagonist, inositol triphosphate receptor 3, interleukin, growth factor or collagen RNA (or a copy thereof) are typically selected so that those probes will hybridize selectively to an RNA transcribed from an angiotensin II receptor, interleukin I receptor antagonist, inositol triphosphate receptor 3, interleukin, growth factor or collagen gene.

Primers and probe sequences can be analyzed to ascertain whether they will likely hybridize selectively to an RNA transcribed from an angiotensin II receptor, interleukin I receptor antagonist, inositol triphosphate receptor 3, interleukin, growth factor or collagen gene. One of skill in the art can readily select probes and primers that will hybridize selectively to a given sequence, for example, to angiotensin II receptor, interleukin I receptor antagonist, inositol triphosphate receptor 3, interleukin, growth factor or collagen RNA.

Factors to consider in selecting primers and probe sequences that will hybridize selectively include whether the primer or probe sequence is unique or conserved and whether the hybridization conditions are sufficiently selective. One of skill in the art can ascertain whether the primer or probe sequence is unique or conserved by determining whether the selected primer or probe sequence shares sequence identity with known genes. Such determinations can readily be performed by one of skill in the art using available computer search programs and databases of nucleic acid (and protein sequences).

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are available in the art. Thus, the determination of percent identity between any two sequences can be accomplished using a mathematical algorithm. Preferred, non-limiting examples of such mathematical algorithms are the algorithm of Myers and Miller (1988); the local homology algorithm of Smith et al. (1981); the homology alignment algorithm of Needleman and Wunsch (1970); the search-for-similarity-method of Pearson and Lipman (1988); the algorithm of Karlin and Altschul (1990), modified as in Karlin and Altschul (1993).

Computer programs that employ such mathematical algorithms can be utilized for comparison of sequences to determine sequence identity. Such programs include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988); Higgins et al. (1989); Corpet et al. (1988); Huang et al. (1992); and Pearson et al. (1994). The ALIGN program is based on the algorithm of Myers and Miller, supra. The BLAST programs of Altschul et al. (1990), are based on the algorithm of Karlin and Altschul supra.

Software for performing BLAST analyses is publicly available through the National Center for Biotechnology Information (ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, or less than about 0.01, or less than about 0.001.

To obtain gapped alignments for comparison purposes, Gapped BLAST (in BLAST 2.0) can be utilized as described in Altschul et al. (1997). Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See http://www.ncbi.nlm.nih.gov. Alignment may also be performed manually by inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e) The term "substantial identity" of polynucleotide sequences means that a polynucleotide comprises a sequence that has at least 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, more preferably at least 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl (1984); $T_m=81.5°$ C.$+16.6$ (log M)$+0.41$ (% GC)$-0.61$ (% form)$-500$/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. An extensive guide to the hybridization of nucleic acids is found in Tijssen (1993). Generally, highly stringent hybridization and wash conditions are selected to be about 5° C. lower than the thermal melting point ($T_m$) for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook and Russell, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

In another embodiment, the invention involves a method of quantifying mRNA expression levels of angiotensin II receptor, interleukin I receptor antagonist, inositol triphosphate receptor 3, interleukin, growth factor and/or collagen in a tissue sample by hybridizing RNA obtained from the tissue sample to an array of nucleic acid probes and quantifying the amount of RNA hybridized to the different probes. In some embodiments, a cDNA pool is quantitatively generated from the RNA prior to hybridization to the array. The cDNA pool can also be amplified as described herein using an internal standard. The array of nucleic acid probes employed can include probes capable of selectively hybridizing to an angiotensin II receptor, interleukin I receptor antagonist, inositol triphosphate receptor 3, interleukin, growth factor and/or collagen nucleic acid.

Thus, in some embodiments, RNA samples, cDNA samples or amplicons thereof are hybridized to the arrays. The resulting hybridization signal provides an indication of the level of expression of each gene of interest. The arrays employed can have a high degree of probe redundancy (multiple probes per gene) so that the expression monitoring methods provide an essentially accurate absolute measurement and do not require comparison to a reference nucleic acid.

Thus, the invention provides methods for monitoring gene expression (expression monitoring) using an array or microarray of oligonucleotide probes. Generally the methods of monitoring gene expression of this invention involve (1) providing a sample containing a pool of target nucleic acids comprising RNA transcript(s) of one or more target gene(s) or nucleic acids derived from the RNA transcript(s); (2) hybridizing the nucleic acid sample to an array of probes (possibly including control probes); and (3) detecting the hybridized nucleic acids and calculating a relative expression (transcription) level. These methods involve the use of oligonucleotide arrays containing probes to specifically preselected genes, for example, angiotensin II receptor, interleukin I receptor antagonist, inositol triphosphate receptor 3, interleukin, growth factor and/or collagen genes.

Methods of preparing and using probe arrays for quantifying gene expression levels are available in the art. See, e.g., U.S. Pat. No. 6,344,316. The oligonucleotide arrays can have oligonucleotides as short as 10 nucleotides, or 15 nucleotides or 20 nucleotides or 25 nucleotides to specifically detect and quantify nucleic acid expression levels. Where ligation discrimination methods are used, for example, as described in U.S. Pat. No. 6,344,316, the oligonucleotide arrays can contain shorter oligonucleotides. In this instance, oligonucleotide arrays can have oligonucleotide probes ranging in length from 6 to 15 nucleotides, or about 8 to about 12 nucleotides. Of course arrays containing longer oligonucleotides are also suitable.

The location and sequence of each different oligonucleotide probe in the array is known. Moreover, the large number of different probes can occupy a relatively small area. In some embodiments, the arrays can have a probe density of greater than about 10, greater than about 20, greater than about 30, greater than about 50 or more different oligonucleotide probes per cm$^2$. Moreover, the arrays can have a small surface area. For examples, arrays can have a surface area of less than about 10 cm², less than about 5 cm², less than about 2 cm², or less than about 1 cm². Such small array surface areas permit small sample volumes and extremely uniform hybridization conditions (temperature regulation, salt content, etc.) to be used while the extremely large number of probes allows parallel processing of numerous hybridizations.

Moreover, when only a small area is occupied by the high density arrays, hybridization may be carried out in extremely small fluid volumes (e.g., 250 µl or less, or 100 µl or less, or even 10 µl or less). In addition, hybridization conditions are extremely uniform throughout the sample, and the hybridization format is amenable to automated processing.

Arrays and microarrays of oligonucleotide probes can be made using procedures and materials available to one of skill in the art. An oligonucleotide array can be synthesized on a solid substrate by a variety of methods, including, but not limited to, light-directed chemical coupling, and mechanically directed coupling. See Pirrung et al., U.S. Pat. No. 5,143,854 (see also PCT Application No. WO 90/15070) and Fodor et al., PCT Publication Nos. WO 92/10092 and WO 93/09668 that disclose methods of forming vast arrays of peptides, oligonucleotides and other molecules using, for example, light-directed synthesis techniques. See also, Fodor et al., Science, 251, 767-77 (1991). These procedures for synthesis of polymer arrays are sometimes referred to as VLSIPS™ procedures. The development of VLSIPS™ technology is described in U.S. Pat. No. 5,143,854 and PCT patent publication Nos. WO 90/15070 and 92/10092. See also, U.S. Pat. No. 6,344,316.

In brief, the light-directed combinatorial synthesis of oligonucleotide arrays on a glass surface proceeds using automated phosphoramidite chemistry and chip masking techniques. In one specific implementation, a glass surface is derivatized with a silane reagent containing a functional group, e.g., a hydroxyl or amine group blocked by a photolabile protecting group. Photolysis through a photolithographic mask is used selectively to expose functional groups which are then ready to react with incoming 5'-photoprotected nucleoside phosphoramidites. The phosphoramidites react only with those sites which are illuminated (and thus exposed by removal of the photolabile blocking group). Thus, the phosphoramidites only add to those areas selectively exposed from the preceding step. These steps are repeated until the desired array of sequences has been synthesized on the solid surface. Combinatorial synthesis of different oligonucleotide analogues at different locations on the array is determined by the pattern of illumination during synthesis and the order of addition of coupling reagents.

In the event that an oligonucleotide analogue with a polyamide backbone is used in the VLSIPS™ procedure, it is generally inappropriate to use phosphoramidite chemistry to perform the synthetic steps, because the monomers do not attach to one another via a phosphate linkage. Instead, peptide synthetic methods are substituted. See, e.g., Pirrung et al. U.S. Pat. No. 5,143,854.

Peptide nucleic acids are commercially available from, for example, Biosearch, Inc. (Bedford, Mass.). These peptide nucleic acids comprise a polyamide backbone and the bases found in naturally occurring nucleosides. Peptide nucleic acids are capable of binding to nucleic acids with high specificity, and are considered "oligonucleotide analogues" useful for the arrays of the invention.

In addition to the foregoing, additional methods which can be used to generate an array of oligonucleotides on a single substrate are described in co-pending applications in PCT Publication No. WO 93/09668. For example, methods for generating arrays of oligonucleotides include delivery of reagents to the substrate by either (1) flowing within a channel defined on predefined regions or (2) "spotting" on predefined regions. However, other approaches, as well as combinations of spotting and flowing, may be employed. In each instance, certain activated regions of the substrate are mechanically separated from other regions when the monomer solutions are delivered to the various reaction sites.

A typical "flow channel" method applied to the arrays of the present invention can generally be described as follows. Diverse polymer sequences are synthesized at selected regions of a substrate or solid support by forming flow channels on a surface of the substrate through which appropriate reagents flow or in which appropriate reagents are placed. For example, assume a monomer "A" is to be bound to the substrate in a first group of selected regions. If necessary, all or part of the surface of the substrate in all or a part of the selected regions is activated for binding, for example, by flowing appropriate reagents through all or some of the channels, or by washing the entire substrate with appropriate reagents. After placement of a channel block on the surface of the substrate, a reagent having the monomer A flows through or is placed in all or some of the channel(s). The channels provide fluid contact to the first selected regions, thereby binding the monomer A on the substrate directly or indirectly (via a spacer) in the first selected regions.

Thereafter, a monomer B is coupled to second selected regions, some of which may be included among the first selected regions. The second selected regions will be in fluid contact with a second flow channel(s) through translation, rotation, or replacement of the channel block on the surface of the substrate; through opening or closing a selected valve; or through deposition of a layer of chemical or photoresist. If necessary, a step is performed for activating at least the second regions. Thereafter, the monomer B is flowed through or placed in the second flow channel(s), binding monomer B at the second selected locations. In this particular example, the resulting sequences bound to the substrate at this stage of processing will be, for example, A, B, and AB. The process is repeated to form a vast array of sequences of desired length at known locations on the substrate.

After the substrate is activated, monomer A can be flowed through some of the channels, monomer B can be flowed through other channels, a monomer C can be flowed through still other channels, etc. In this manner, many or all of the reaction regions are reacted with a monomer before the channel block must be moved or the substrate must be washed and/or reactivated. By making use of many or all of the available reaction regions simultaneously, the number of washing and activation steps can be minimized.

One of skill in the art will recognize that there are alternative methods of forming channels or otherwise protecting a portion of the surface of the substrate. For example, according to some embodiments, a protective coating such as a hydrophilic or hydrophobic coating (depending upon the nature of the solvent) is utilized over portions of the substrate to be protected, sometimes in combination with materials that facilitate wetting by the reactant solution in other regions. In this manner, the flowing solutions are further prevented from passing outside of their designated flow paths.

In some embodiments the channels will be formed by depositing an electron or photoresist such as those used in the semiconductor industry. Such materials include polymethyl methacrylate (PMMA) and its derivatives, and electron beam resists such as poly(olefin sulfones) and the like (more fully described in Chapter 10 of Ghandi, VLSI Fabrication Principles, Wiley (1983)). According to these embodiments, a resist is deposited, selectively exposed, and etched, leaving a portion of the substrate exposed for coupling. These steps of depositing resist, selectively removing resist and monomer coupling are repeated to form polymers of desired sequence at desired locations.

The "spotting" methods of preparing arrays of the present invention can be implemented in much the same manner as the flow channel methods. For example, a monomer A, or a coupled, or dimer, or trimer, or tetramer, etc, or a fully synthesized material, can be delivered to and coupled with a first group of reaction regions that have been appropriately activated. Thereafter, a monomer B can be delivered to and reacted with a second group of activated reaction regions. Unlike the flow channel embodiments described above, reactants are delivered by directly depositing (rather than flowing) relatively small quantities of them in selected regions. In some steps, of course, the entire substrate surface can be sprayed or otherwise coated with a solution. In preferred embodiments, a dispenser moves from region to region, depositing only as much monomer as necessary at each stop. Typical dispensers include a micropipette to deliver the monomer solution to the substrate and a robotic system to control the position of the micropipette with respect to the substrate. In other embodiments, the dispenser includes a series of tubes, a manifold, an array of pipettes, or the like so that various reagents can be delivered to the reaction regions simultaneously.

The amplified or hybridized nucleic acids are detected by detecting one or more labels attached to the RNA, hybridized probe or an amplified product of the RNA sample. The labels may be incorporated by any of a number of means well known to those of skill in the art. For example, the label can be simultaneously incorporated into an amplified product during amplification of a cDNA copy of the original RNA sample. In some embodiments polymerase chain reaction (PCR) with labeled primers or labeled nucleotides can be used to provide a labeled amplification product. The nucleic acid (e.g., cDNA) is be amplified in the presence of labeled deoxynucleotide triphosphates (dNTPs). The amplified nucleic acid can be fragmented, exposed to an oligonucleotide array, and the extent of hybridization determined by the amount of label now associated with the array. In a preferred embodiment, transcription amplification, as described above, using a labeled nucleotide (e.g. fluorescein-labeled UTP and/or CTP) incorporates a label into the transcribed nucleic acids.

A label may be added directly to the original nucleic acid sample (e.g., mRNA, polyA mRNA, cDNA, etc.), to a probe or to an amplification product of the nucleic acid sample. Means of attaching labels to nucleic acids include, for example nick translation or end-labeling (e.g. with a labeled RNA) by kinasing of the nucleic acid and subsequent attachment (ligation) of a nucleic acid linker joining the sample nucleic acid to a label (e.g., a fluorophore).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like, see, e.g., Molecular Probes, Eugene, Ore., USA), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

A fluorescent label is frequently used because it provides a very strong signal with low background. It is also optically detectable at high resolution and sensitivity through a quick scanning procedure. The nucleic acid samples can all be labeled with a single label, e.g., a single fluorescent label. Alternatively, in another embodiment, different nucleic acid samples can be simultaneously hybridized where each nucleic acid sample has a different label. For instance, one target could have a green fluorescent label and a second target could have a red fluorescent label. The scanning step will distinguish cites of binding of the red label from those binding the green fluorescent label. Each nucleic acid sample (target nucleic acid) can be analyzed independently from one another.

Suitable chromogens which can be employed include those molecules and compounds which absorb light in a distinctive range of wavelengths so that a color can be observed or, alternatively, which emit light when irradiated with radiation of a particular wave length or wave length range, e.g., fluorescers.

A wide variety of suitable dyes are available. A dye is primarily chosen to provide an intense color with minimal absorption by its surroundings. Illustrative dye types include quinoline dyes, triarylmethane dyes, acridine dyes, alizarine dyes, phthaleins, insect dyes, azo dyes, anthraquinoid dyes, cyanine dyes, phenazathionium dyes, and phenazoxonium dyes.

A wide variety of fluorescers can be employed either by alone or, alternatively, in conjunction with quencher molecules. Fluorescers of interest fall into a variety of categories having certain primary functionalities. These primary functionalities include 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, marocyanine, 3-aminoequilenin, perylene, bisbenzoxazole, bis-p-oxazolyl benzene, 1,2-benzophenazin, retinol, bis-3-aminopyridinium salts, hellebrigenin, tetracycline, sterophenol, benzimidzaolylphenylamine, 2-oxo-3-chromen, indole, xanthen, 7-hydroxycoumarin, phenoxazine, salicylate, strophanthidin, porphyrins, triarylmethanes and flavin. Individual fluorescent compounds which have functionalities for linking or which can be modified to incorporate such functionalities include, e.g., dansyl chloride; fluoresceins such as 3,6-dihydroxy-9-phenylxanthhydrol; rhodamine isothiocyanate; N-phenyl 1-amino-8-sulfonatonaphthalene; N-phenyl 2-amino-6-sulfonatonaphthalene: 4-acetamido-4-isothiocyanato-stilbene-2,2'-disulfonic acid; pyrene-3-sulfonic acid; 2-toluidinonaphthalene-6-sulfonate; N-phenyl, N-methyl 2-aminoaphthalene-6-sulfonate; ethidium bromide; stebrine; auromine-0,2-(9'-anthroyl)palmitate; dansyl phosphatidylethanolamine; N,N'-dioctadecyl oxacarbocyanine; N,N'-dihexyl oxacarbocyanine; merocyanine, 4(3'pyrenyl)butyrate; d-3-aminodesoxy-equilenin; 12-(9'anthroyl)stearate; 2-methylanthracene; 9-vinylanthracene; 2,2'(vinylene-p-phenylene)bisbenzoxazole; p-bis[2-(4-methyl-5-phenyl-oxazolyl)]benzene; 6-dimethylamino-1,2-benzophenazin; retinol; bis(3'-aminopyridinium) 1,10-decandiyl diiodide; sulfonaphthylhydrazone of hellibrienin; chlorotetracycline; N(7-dimethylamino-4-methyl-2-oxo-3-chromenyl)maleimide; N-[p-(2-benzimidazolyl)-phenyl]maleimide; N-(4-fluoranthyl)maleimide; bis(homovanillic acid); resazarin; 4-chloro-7-nitro-2,1,3benzooxadiazole; merocyanine 540; resorufin; rose bengal; and 2,4-diphenyl-3 (2H)-furanone.

Desirably, fluorescers should absorb light above about 300 nm, preferably about 350 nm, and more preferably above about 400 nm, usually emitting at wavelengths greater than about 10 nm higher than the wavelength of the light absorbed. It should be noted that the absorption and emission characteristics of the bound dye can differ from the unbound dye. Therefore, when referring to the various wavelength ranges and characteristics of the dyes, it is intended to indicate the dyes as employed and not the dye which is unconjugated and characterized in an arbitrary solvent.

Fluorescers are generally preferred because by irradiating a fluorescer with light, one can obtain a plurality of emissions. Thus, a single label can provide for a plurality of measurable events.

Immunoassays

Another aspect of the present invention relates to methods for detecting expression levels of angiotensin II receptor, interleukin I receptor antagonist, inositol triphosphate receptor 3, interleukin, growth factor and/or collagen proteins. As discussed in more detail below, the status of these gene products in wound tissue samples can be analyzed by a variety of protocols that are available in the art including immunohistochemical analysis, Western blot analysis, immunoprecipitation, molecular binding assays, ELISA, ELIFA and similar immunoassay procedures.

The invention therefore provides antibodies against the wound markers of the invention. For example, the antibodies of the invention able to bind angiotensin II receptor, interleukin I receptor antagonist, inositol triphosphate receptor 3, interleukin, growth factor or collagen proteins.

Antibodies of the invention include polyclonal antibodies, monoclonal antibodies, humanized antibodies, chimeric antibodies and fragments of antibodies. These antibodies may be coupled to a detectable marker. Examples of detectable markers include, but are not limited to, radioactivity, a fluorescent tag and an enzyme. The antibodies of the invention may also be conjugated to any of the detectable labels contemplated for use in the hybridization assays described herein. Methods for labeling antibodies are well known in the art and are described in Harlow et al., Antibodies: A Laboratory Manual, page 319 (Cold Spring Harbor Pub. 1988) The preparation of polyclonal antibodies is well-known to those skilled in the art. Green et al., Production of Polyclonal Antisera, in Immunochemical Protocols (Manson, ed.), pages 1-5 (Humana Press 1992); Coligan et al., Production of Polyclonal Antisera in Rabbits, Rats, Mice and Hamsters, in Current Protocols in Immunology, section 2.4.1 (1992).

The preparation of monoclonal antibodies is also well known in the art. Kohler & Milstein, Nature, 256:495 (1975); Coligan et al., sections 2.5.1-2.6.7; and Harlow et al., Antibodies: A Laboratory Manual, page 726 (Cold Spring Harbor Pub. 1988). Briefly, monoclonal antibodies can be obtained by injecting mice with a composition comprising a bacteriophage, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the chronic wound markers disclosed herein, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. Coligan et al., sections 2.7.1-2.7.12 and sections 2.9.1-2.9.3; Barnes et al., Purification of Immunoglobulin G (IgG), in Methods in Molecular Biology, Vol. 10, pages 79-104 (Humana Press 1992).

Monoclonal antibodies may be produced in vitro through use of well known techniques. Production in vitro provides relatively pure antibody preparations and allows scale-up to yield large amounts of the desired antibodies. Large scale hybridoma cultivation can be carried out by homogenous suspension culture in an air reactor, in a continuous stirrer reactor, or immobilized or entrapped cell culture. Multiplication in vivo may be carried out by injecting cell clones into mammals histocompatible with the parent cells, e.g., syngeneic mice, to cause growth of antibody-producing tumors. Optionally, the animals are primed with a hydrocarbon, especially oils such as pristine tetramethylpentadecane prior to injection. After one to three weeks, the desired monoclonal antibody is recovered from the body fluid of the animal.

Antibody fragments of the invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods have been described. Goldenberg, U.S. Pat. No. 4,036,945 and 4,331,647; Porter, *Biochem. J.,* 73:119 (1959); Edelman et al., Methods in Enzymology, Vol. 1, page 422 (Academic Press 1967); and Coligan et al. at sections 2.8.1-2.8.10 and 2.10.1-2.10.4. Other methods of cleaving antibodies, such as separation of heavy chains to form monovalent light-heavy chain fragments, further cleavage of fragments, or other enzymatic, chemical, or genetic techniques may also be used, so long as the fragments bind to the same chronic wound marker that is recognized by the intact antibody.

Antibodies that can bind angiotensin II receptor, interleukin I receptor antagonist, inositol triphosphate receptor 3, interleukin, growth factor and/or collagen proteins can be used in any convenient immunoassay for detecting or monitoring the status of chronic wounds. Examples of immunoassays include radioimmunoassays, competitive binding assays, sandwich assays, and immunoprecipitation assays.

Competitive binding assays rely on the ability of a labeled standard to compete with the test sample analyte for binding with a limited amount of antibody. The labeled standard may be an angiotensin II receptor, interleukin I receptor antagonist, inositol triphosphate receptor 3, interleukin, growth factor or collagen protein. The amount of test sample is inversely proportional to the amount of standard that becomes bound to the antibodies. To facilitate determining the amount of standard that becomes bound, the antibodies employed are generally made insoluble either before or after the competition. This is done so that the standard and analyte that are bound to the antibodies may be conveniently separated from the standard and analyte that remain unbound.

Sandwich assays involve the use of two antibodies, each capable of binding to a different immunogenic portion, or epitope, of the product to be detected. In a sandwich assay, the test sample analyte is bound by a first antibody which is immobilized on a solid support, and thereafter a second antibody binds to the analyte, thus forming an insoluble three part complex (David & Greene, U.S. Pat. No. 4,376,110). The second antibody may itself by labeled with a detectable moiety (direct sandwich assays) or may be measured using a third antibody that binds the second antibody and is labeled with a detectable moiety (indirect sandwich assay). For example, one type of sandwich assay is an ELISA assay, in which case the detectable moiety is an enzyme.

Typically, sandwich assays include "forward" assays in which the antibody bound to the solid phase is first contacted with the sample being tested to extract the target protein (a chronic wound marker of the invention) from the sample by formation of a binary solid phase complex between the immobilized antibody and the target protein. After a suitable incubation period, the solid support is washed to remove unbound fluid sample, including unreacted target protein, if any. The solid support is then contacted with the solution containing an unknown quantity of labeled antibody (which functions as a label or reporter molecule). After a second incubation period to permit the labeled antibody to react with the complex between the immobilized antibody and the target protein, the solid support is washed a second time to remove the unreacted labeled antibody.

Other types of sandwich assays that may be used include the so-called "simultaneous" and "reverse" assays. A simultaneous assay involves a single incubation step wherein the labeled and unlabeled antibodies are, at the same time, both exposed to the sample being tested. The unlabeled antibody is immobilized onto a solid support, while the labeled antibody is free in solution with the test sample. After the incubation is completed, the solid support is washed to remove unreacted sample and uncomplexed labeled antibody. The presence of labeled antibody associated with the solid support is then determined as it would be in a conventional "forward" sandwich assay.

In a "reverse" assay, stepwise addition is utilized, first of a solution of labeled antibody to a test sample, followed by incubation, and then later by addition of an unlabeled antibody bound to a solid support. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays.

In addition to their diagnostic utility, the antibodies of the present invention are useful for monitoring the progression of a wound present on a mammalian subject by examining the levels of chronic wound markers in tissue or cells samples over time. Changes in the levels of chronic wound markers over time may indicate the wound is healing or progressing further towards being a chronic wound. Interventional therapies can then be devised to better treat the wound.

Identification of Molecules that can Modulate Wound Status

The discovery that expression levels of certain genes (chronic wound markers) are altered in chronic wounds allows a skilled artisan to identify proteins, small molecules and other agents that interact with the gene products of those chronic wound markers or that modulate the transcription of the chronic wound marker genes. As described herein the chronic wound markers contemplated include angiotensin II receptor, interleukin I receptor antagonist, inositol triphosphate receptor 3, interleukin, growth factor and/or collagen genes and their gene products.

A variety of art accepted protocols can be adapted for identifying agents that can modulate the expression or activity of angiotensin II receptor, interleukin I receptor antagonist, inositol triphosphate receptor 3, interleukin, growth factor and/or collagen. For example, one can utilize one of the so-called interaction trap systems (also referred to as the "two-hybrid assay"). In such systems, molecules interact and reconstitute a transcription factor which directs expression of a reporter gene, whereupon the expression of the reporter gene is assayed. Other systems identify protein-protein interactions in vivo through reconstitution of a eukaryotic transcriptional activator, see, e.g., U.S. Pat. No. 5,955,280 issued Sep. 21, 1999, U.S. Pat. No. 5,925,523 issued Jul. 20, 1999, U.S. Pat. No. 5,846,722 issued Dec. 8, 1998 and U.S. Pat. No. 6,004,746 issued Dec. 21, 1999. Algorithms are also available in the art for genome-based predictions of protein function (see, e.g., Marcotte, et al., Nature 402: Nov. 4, 1999, 83-86).

Alternatively one can screen peptide libraries to identify molecules that interact with angiotensin II receptor, interleukin I receptor antagonist, inositol triphosphate receptor 3, interleukin, growth factor and/or collagen protein sequences. In such methods, peptides that bind to these proteins are identified by screening libraries that encode a random or controlled collection of amino acids. Peptides encoded by the libraries are expressed as fusion proteins of bacteriophage coat proteins, the bacteriophage particles are then screened against the angiotensin II receptor, interleukin I receptor antagonist, inositol triphosphate receptor 3, interleukin, growth factor and/or collagen protein(s). Peptides having a wide variety of uses, such as therapeutic, prognostic or diagnostic reagents, are thus identified.

Typical peptide libraries and screening methods that can be used to identify molecules that interact with angiotensin II receptor, interleukin I receptor antagonist, inositol triphosphate receptor 3, interleukin, growth factor and/or collagen protein sequences are disclosed for example in U.S. Pat. No. 5,723,286 issued Mar. 3, 1998 and U.S. Pat. No. 5,733,731 issued Mar. 31, 1998.

Alternatively, cell lines that express angiotensin II receptor, interleukin I receptor antagonist, inositol triphosphate receptor 3, interleukin, growth factor and/or collagen proteins are used to identify protein-protein interactions mediated by these proteins. Such interactions can be examined using immunoprecipitation techniques (see, e.g., Hamilton B. J., et al. Biochem. Biophys. Res. Commun. 1999, 261:646-51). The angiotensin II receptor, interleukin I receptor antagonist, inositol triphosphate receptor 3, interleukin, growth factor and/or collagen proteins can be immunoprecipitated from the cell lines using the antibodies described herein. Alternatively, antibodies against His-tag can be used in a cell line engineered to express fusions of these proteins with His-tag. The immunoprecipitated complex can be examined for protein association, for example, by procedures such as Western blotting, $^{35}$S-methionine labeling of proteins, protein microsequencing, silver staining and two-dimensional gel electrophoresis.

Small molecules and ligands that interact with angiotensin II receptor, interleukin I receptor antagonist, inositol triphosphate receptor 3, interleukin, growth factor and/or collagen can be identified through screening assays. For example, small molecules can be identified that interfere with protein function, including molecules that interfere with the ability of these chronic wound markers to modulate wound progression in an appropriate animal model. Moreover, ligands that regulate the function of these chronic wound markers can be identified based on their ability to bind the chronic wound marker protein(s) and activate a reporter construct. Typical methods are discussed for example in U.S. Pat. No. 5,928,868 issued Jul. 27, 1999, and include methods for forming hybrid ligands in which at least one ligand is a small molecule.

Another embodiment of this invention comprises a method of screening for a molecule that interacts with an angiotensin II receptor, interleukin I receptor antagonist, inositol triphosphate receptor 3, interleukin, growth factor and/or collagen amino acid sequence. The method can include contacting a population of molecules with an angiotensin II receptor, interleukin I receptor antagonist, inositol triphosphate receptor 3, interleukin, growth factor and/or collagen marker protein, allowing the population of molecules and the marker protein to interact under conditions that facilitate an interaction, determining the presence of a molecule that interacts with the marker protein, and then separating molecules that do not interact with the marker protein from molecules that do. In a specific embodiment, the method further comprises purifying, characterizing and identifying a molecule that interacts with the marker protein. The identified molecule can be used to modulate a function performed by angiotensin II receptor, interleukin I receptor antagonist, inositol triphosphate receptor 3, interleukin, growth factor and/or collagen. In some embodiments, the marker protein is contacted with a library of peptides.

In further embodiments, the invention provides a method of identifying an agent that can modulate the expression of an angiotensin II receptor, interleukin I receptor antagonist, inositol triphosphate receptor 3, interleukin, growth factor and/or collagen gene. This method involves generating a nucleic acid construct or vector by linking a nucleic acid encoding a detectable marker to a nucleic acid encoding a promoter sequence for an angiotensin II receptor, interleukin I receptor antagonist, inositol triphosphate receptor 3, interleukin, growth factor and/or collagen gene. The nucleic acid construct or vector is then introduced into a host cell that normally can express angiotensin II receptor, interleukin I receptor antagonist, inositol triphosphate receptor 3, interleukin, growth factor and/or collagen. The host cell is then exposed to different test agents and the expression level of the detectable marker is observed to ascertain whether the test agents can modulate the expression from the angiotensin II receptor, interleukin I receptor antagonist, inositol triphosphate receptor 3, interleukin, growth factor and/or collagen promoter. In this manner, agents that can increase or decrease angiotensin II receptor, interleukin I receptor antagonist, inositol triphosphate receptor 3, interleukin, growth factor and/or collagen expression can be identified.

The invention is further illustrated by the following non-limiting Examples.

EXAMPLE 1

Expression of Angiotensin II Receptor is Dramatically Reduced in Chronic Venous Stasis Leg Ulcers This Example provides an analysis of angiotensin II receptor gene expression in chronic venous stasis leg ulcers from seven patients showing that such expression is less than about 62% of its level in healthy tissues from the same patients.

Materials and Methods

Standard procedures were used for obtaining tissue biopsies that had an outer diameter of about 2 mm and a depth of about 5 mm. The biopsy sites received a local anesthetic and alcohol swab before the biopsies are performed. After biopsy, the site received antibiotic treatment (0.3% gentamycin) to minimize any risk of subsequent infection. Biopsies of both healthy and chronic wound tissues were treated similarly. While there was some concern that biopsies of chronic wounds would impair wound healing, previous studies demonstrated that biopsies of this type did not impact rates of wound closure or healing rates.

Tissue biopsies were homogenized and mRNA extracted by standard procedures. RNA levels was quantified for a number of genes, including cytokines, mediators of inflammation, key enzymes involved in tissue repair and regrowth, etc. RNA expression levels were compared to those in the healthy tissue controls, and were monitored at several time points.

Array of probes were used to screen RNA samples. Examples of the types of probes on the arrays include probes from the genes listed in Table 1.

TABLE 1

| Gene Name | Symbol |
|---|---|
| A disintegrin and metalloproteinase domain 11 | ADAM11 |
| A disintegrin and metalloproteinase domain 23 | ADAM23 |
| Adrenergic, alpha-1C-, receptor | ADRA1C |
| alanyl-tRNA synthetase | AARS |
| angiotensin II receptor | AGTR2 |
| aldehyde dehydrogenase 5 family, member A1 (succinate-semialdehydedehydrogenase) | ALDH5A1 |
| aldo-keto reductase family 1, member C4 (chlordecone reductase; 3-alpha hydroxysteroid dehydrogenase, type | AKR1C4 |
| annexin A5 | ANXA5 |
| aquaporin 3 | AQP3 |
| arginine vasopressin receptor 2 (nephrogenic diabetes insipidus) | AVPR2 |
| aryl hydrocarbon receptor nuclear translocator | ARNT |
| ATP synthase, H+ transporting, mitochondrial F1F0, subunit d | ATP5JD |
| ATP-binding cassette, sub-family A (ABC1), member 2 | ABCA2 |
| ATP-binding cassette, sub-family D (ALD), member 1 | ABCD1 |
| ATP-binding cassette, sub-familyG (WHITE), member 2 | ABCG2 |
| benzodiazapine receptor (peripheral) | BZRP |
| calcium and integring binding protein (DNA-dependent protein kinase interacting protein) | SIP2-28 |
| calcium channel, voltage-dependent, alpha 1H subunit | CACNA1H |
| calcium channel, voltage-dependent, P/Q type, alpha 1A subunit | CACNA1A |
| calcium-sensing receptor(hypocalciuric hypercalcemia 1, severe neonatal hyperparathyroidism) | CASR |
| caspase 7, apoptosis-related cysteine protease | CASP7 |
| cathepsin C | CTSC |
| CD36 antigen (collagen type I receptor, thrombospondin receptor) | CD36 |
| chemokine-like receptor 1 | CMKLR1 |
| chloride channel 7 | CLCN7 |

TABLE 1-continued

| Gene Name | Symbol |
|---|---|
| Cholinergic receptor, nicotinic, delta polypeptide | CHRND |
| clusterin (complement lysis inhibitor, SP-40, 40, sulfated glycoprotein 2, testosterone-repressed prostate message 2, apolipoprotein J) | CLU |
| coagulation factor VII (serum prothrombin conversion prothrombin conversion | F7 |
| collagen, type I, alpha 1 | COL1A1 |
| collagen, type I, alpha 2 | COL1A2 |
| collagen, type III, alpha 1 (Ehlers-Danlos syndrome type IV, autosomal dominant | COL3A1 |
| collagen, type III, alpha 1 (Ehlers-Danlos syndrome type IV, autosomal dominant) | COL3A1 |
| collagen, type IV, alpha 1 | COL4A1 |
| collagen, type VI, alpha 1 | COL6A1 |
| collagen, type VI, alpha 2 | COL6A2 |
| collagen, type VII, alpha 1 (epidermolysis bullosa, dystrophic, dominant and recessive) | COL7A1 |
| collagen, type XV, alpha 1 | COL15A1 |
| complement component 1 inhibitor (angioedema, hereditary) | C1NH |
| c-src tyrosine kinase | CSK |
| cyclin A2 | CCNA2 |
| cyclin B2 | ccnb2 |
| cyclin D3 | CCND3 |
| cyclin-dependent kinase inhibitor 1B (p27, Kip1) | CDKN1B |
| cystatin A (stefin A) | CSTA |
| cystatin E/M | CST6 |
| cytochrome P450, subfamily I (aromatic compound-inducible) polypeptide 2 | CYP1A2 |
| cytochrome P450, subfamily IID (debrisoquine, sparteine, etc., -metabolizing), polypeptide 6 | CYP2D6 |
| DEAD/H (Asp-Glu-Ala-Asp/His) box polypeptide 5 (RNA helicase, 68 kD) | DDX5 |
| death-associated protein kinase 1 | DAPK1 |
| diazepam binding inhibitor (GABA receptor modulator, acyl-Coenzyme A binding protein) | DBI |
| dipeptidylpeptidase IV (CD26, adenosine deaminase complexing protein 2) | DPP4 |
| dishevelled 3 (homologous to *Drosophila* dsh) | DVL3 |
| dual specificity phosphatase 3 (vaccinia virus phosphatase VH1-related) | DUSP3 |
| dual specificity phosphatase 5 | DUSP5 |
| dysferlin, limb girdle muscular dystrophy 2B (autosomal recessive) | DYSF |
| Endothelin 3 | EDN3 |
| epidermal growth factor | EGF |
| Epididymis-specific, whey-acidic protein type, four-disulfide core | HE4 |
| Fc fragment of IgA, receptor for | FCAR |
| Fc fragment of IgG, high affinity Ia, receptor for (CD64) | FCGR1A |
| Fc fragment of IgG, low affinity IIIa, receptor for (CD16) | FCGR3A |
| Fc fragment of IgG, receptor, transporter, alpha | FCGRT |
| fibroblast growth factor 1 (acidic) | FGF1 |
| G antigen 1 | GAGE1 |
| G protein-coupled receptor 3 | GPR3 |
| GATA-binding protein 3 | GATA3 |
| general transcription factor IIIA | GTF3A |
| glucagon-like peptide 1 receptor | GLP1R |
| glucosidase, alpha; acid (Pompe disease, glycogen storage disease type II) | GAA |
| glutathione S-transferase M2 (muscle) | GSTM2 |
| glycerol kinase pseudogene 2 | GKP2 |
| glycine receptor, alpha 2 | GLRA2 |
| gonadotropin-releasing hormone receptor | GNRHR |
| GRO1 oncogene (melanoma growth stimulating activity, alpha) | GRO1 |
| growth factor independent 1 | GFI1 |
| heat shock 70 kD protein 6 (HSP70B') | HSPA6 |
| herpesvirus entry mediator C (poliovirus receptor-related 1; nectin) | HVEC |
| heterogeneous nuclear ribonucleoproteins A1 | HNRPA1 |
| heterogeneous nuclear ribonucleoproteins D | HNRPD |
| HLA-B associated transcript-1 | D6S81E |
| HLA-G histocompatibility antigen, class I, G | HLA-G |
| HLA-G histocompatibility antigen, class I, G | HLA-G |
| homeo box B13 | HOXB13 |
| hydroxyacyl-Coenzyme A dehydrogenase/3-ketoacyl-Coenzyme A thiolase/enoyl-Coenzyme A hydratase (trifunctional protein), alpha subunit | HADHA |

TABLE 1-continued

| Gene Name | Symbol |
|---|---|
| hypoxia-inducible factor 1, alpha subunit (basic helix-loop-helix transcription factor) | HIF1A |
| immunoglobulin gamma 3 (Gm marker) | IGHG3 |
| inhibitor of kappa light polypeptide gene enhancer in B-cells, kinase gamma | IKBKG |
| inositol 1,4,5-triphosphate receptor, type 3 | ITPR3 |
| integrin, alpha 2 (CD49B, alpha 2 subunit of VLA-2 receptor) | ITGA2 |
| integrin, alpha 2 (CD49B, alpha 2 subunit of VLA-2 receptor) | ITGA2 |
| integrin, alpha 3 (antigen CD49C, alpha 3 subunit of VLA-3 receptor) | ITGA3 |
| integrin, alpha 5 (fibronectin receptor, alpha polypeptide) | ITGA5 |
| integrin, alpha 7 | ITGA7 |
| integrin, beta 1 (fibronectin receptor, beta polypeptide, antigen CD29 includes MDF2, MSK12) | ITGB1 |
| integrin, beta 1 (fibronectin receptor, beta polypeptide, antigen CD29 includes MDF2, MSK12) | ITGB1 |
| integrin, beta 4 | ITGB4 |
| interferon (alpha, beta and omega) receptor 2 | IFNAR2 |
| interferon (alpha, beta and omega) receptor 2 | IFNAR2 |
| Interleukin 1 receptor antagonist | IL1RN |
| Interleukin 1, beta | IL1B |
| Interleukin 1, beta | IL1B |
| Interleukin 17 receptor | IL17R |
| Interleukin 17 receptor | IL17R |
| Interleukin 3 (colony-stimulating factor, multiple) | IL3 |
| Interleukin 8 | IL8 |
| Interleukin 8 | IL8 |
| killer cell lectin-like receptor subfamily C, member 2 | KLRC2 |
| lactate dehydrogenase A | LDHA |
| lamin A/C | LMNA |
| LIM domain kinase 1 | LIMK1 |
| macrophage lectin 2 (calcium dependent) | HML2 |
| macrophage receptor with collagenous structure | MARCO |
| major histocompatibility complex, class I, C | HLA-C |
| mannose receptor, C type 1 | MRC1 |
| mannose-6-phosphate receptor (cation dependent) | M6PR |
| matrix metalloproteinase 11 (stromelysin 3) | MMP11 |
| matrix metalloproteinase 19 | MMP19 |
| matrix metalloproteinase 2 (gelatinase A, 72 kD gelatinase, 72 kD type IV collagenase) | MMP2 |
| meiotic recombination (*S. cerevisiae*) 11 homolog B | MRE11B |
| melanocortin 1 receptor (alpha melanocyte stimulating hormone receptor) | MC1R |
| methyl-CpG binding domain protein 2 | MBD2 |
| mitogen-activated protein kinase kinase kinase 10 | MAP3K10 |
| myosin VA (heavy polypeptide 12, myoxin) | MYO5A |
| myosin-binding protein C, cardiac | MYBPC3 |
| N-acetylglucosaminidase, alpha-(Sanfilippo disease IIIB) | NAGLU |
| NADH dehydrogenase (ubiquinone) Fe-S protein 6 (13 kD) (NADH-coenzyme Q reductase) | NDUFS6 |
| neural cell adhesion molecule 1 | NCAM1 |
| neuronal apoptosis inhibitory protein | NAIP |
| neuronal PAS domain protein 1 | NPAS1 |
| N-myc (and STAT) interactor | NMI |
| non-metastatic cells 3, protein expressed in | NME3 |
| Notch (*Drosophila*) homolog 3 | NOTCH3 |
| nuclear factor (erythroid-derived 2), 45 kD | NFE2 |
| nuclear transcription factor, X-box binding 1 | NFX1 |
| p21/Cdc42/Rac1-activated kinase 1 (yeast Ste20-related) | PAK1 |
| paired box gene 3 (Waardenburg syndrome 1) | PAX3 |
| paraoxonase 1 | PON1 |
| patched (*Drosophila*) homolog | PTCH |
| phenylalanine-tRNA synthetase-like | FARSL |
| phosphoglycerate kinase 1 | PGK1 |
| plasminogen activator, urokinase receptor | PLAUR |
| pM5 protein | PM5 |
| Potassium channel, subfamily K, member 3 (TASK) | KCNK3 |
| Potassium inwardly-rectifying channel, subfamily J, member 8 | KCNJ8 |
| Potassium inwardly-rectifying channel, subfamily J, member 4 | KCNJ4 |
| POU domain, class 2, transcription factor 1 | POU2F1 |
| prostaglandin I2 (prostacyclin) receptor (IP) | PTGIR |
| proteasome (prosome, macropain) subunit, beta type, 10 | PSMB10 |
| protein inhibitor of activated STAT protein PIASy mRNA, complete cds | PIASY |
| protein phosphatase 2A, regulatory subunit B' (PR 53) | PPP2R4 |
| protein tyrosine phosphatase type IVA, member 3 | PTP4A3 |
| protein tyrosine phosphatase, receptor type, N | PTPRN |
| Proteolipid protein 2 (colonic epithelium-enriched) | PLP2 |

TABLE 1-continued

| Gene Name | Symbol |
|---|---|
| purinergic receptor P2Y, G-protein coupled, 2 | P2RY2 |
| quiescin Q6 | QSCN6 |
| receptor (TNFRSF)-interacting serine-threonine kinase 1 | RIPK1 |
| ribosomal protein L10 | RPL10 |
| ribosomal protein S15 | RPS15 |
| ryanodine receptor 1 (skeletal) | RYR1 |
| secreted protein, acidic, cysteine-rich (osteonectin) | SPARC |
| serologically defined colon cancer antigen 10 | SDCCAG10 |
| SH3-domain GRB2-like 1 | SH3GL1 |
| small inducible cytokine A3 (homologous to mouse Mip-1a) | SCYA3 |
| small inducible cytokine subfamily A (Cys—Cys), member 11 (eotaxin) | SCYA11 |
| small inducible cytokine subfamily A (Cys—Cys), member 18, pulmonary and activation-regulated | SCYA18 |
| small nuclear ribonucleoprotein polypeptide A | SNRPA1 |
| solute carrier family 15 (oligopeptide transporter), member 1 | SLC15A1 |
| special AT-rich sequence binding protein 1 (binds to nuclear matrix/scaffold-associating DNA's) | SATB1 |
| Synaptophysin | SYP |
| T-cell acute lymphocytic leukemia 1 | TAL1 |
| thyroid autoantigen 70 kD (Ku antigen) | G22P1 |
| tissue inhibitor of metalloproteinase 1 (erythroid potentiating activity, collagenase inhibitor) | TIMP1 |
| tissue inhibitor of metalloproteinase 2 | TIMP2 |
| tissue inhibitor of metalloproteinase 3 (Sorsby fundus dystrophy, pseudoinflammatory) | TIMP3 |
| transforming growth factor, beta receptor III (betaglycan, 300 kD) | TGFBR3 |
| transforming growth factor, beta-induced, 68 kD | TGFBI |
| tumor necrosis factor receptor superfamily, member 1A | TNFRSF1A |
| tumor necrosis factor receptor superfamily, member 1B | TNFRSF1B |
| upstream binding transcription factor, RNA polymerase I | UBTF |
| voltage-gated sodium channel alpha subunit (SCN8A), exons 18N and 18A | scn8a |
| X-ray repair complementing defective repair in Chinese hamster cells 2 | XRCC2 |

Results

The average expression levels of the genes listed in Table I on the first through twenty-eighth day (days 0, 7, 14 and 28) of weekly monitoring wound samples from seven patients are provided in Table 2 below. The expression levels of potentially interesting genes are highlighted in bold.

TABLE 2

| Symbol | Day 0 Consensus | Day 7 Consensus | Day 14 Consensus | Day 28 Consensus |
|---|---|---|---|---|
| ADAM11 | −0.549 | −1.091 | −0.556 | −0.408 |
| ADAM23 | −3.079 | −0.307 | −2.131 | −2.892 |
| ADRA1C | −0.862 | 0.022 | −0.134 | −0.211 |
| AARS | −1.419 | −1.527 | −2.809 | −2.731 |
| AGTR2 | −4.122 | −4.098 | −3.781 | −3.904 |
| ALDH5A1 | −1.241 | −1.149 | 0.264 | −2.419 |
| AKR1C4 | −1.430 | −0.835 | | |
| ANXA5 | | | 1.907 | 1.249 |
| AQP3 | −1.474 | −1.130 | | −1.772 |
| AVPR2 | −2.731 | −0.483 | −1.370 | −2.783 |
| ARNT | −3.215 | −1.299 | −3.460 | −4.008 |
| ATP5JD | −0.601 | −0.534 | −0.901 | 0.348 |
| ABCA2 | −0.336 | −0.565 | 0.258 | −0.264 |
| ABCD1 | −0.114 | −1.796 | −2.187 | −2.112 |
| ABCG2 | −2.283 | −1.218 | −3.445 | −2.636 |
| BZRP | −0.769 | −1.336 | −0.158 | −1.004 |
| SIP2-28 | −3.099 | −3.339 | −2.964 | −3.343 |
| CACNA1H | −1.428 | −2.615 | −3.863 | −3.346 |
| CACNA1A | 1.060 | 0.015 | 0.539 | −0.277 |
| CASR | −0.485 | −0.949 | −0.978 | −0.475 |
| CASP7 | −0.863 | −1.029 | −1.355 | −0.604 |
| CTSC | −1.310 | −0.925 | −0.510 | −1.310 |
| CD36 | −0.269 | −0.067 | −0.390 | −0.754 |
| CMKLR1 | 1.484 | | 3.344 | 1.749 |
| CLCN7 | −1.794 | −1.620 | −1.579 | −1.775 |
| CHRND | | 2.363 | | 3.738 |
| CLU | −1.107 | −1.865 | −1.659 | −1.223 |
| F7 | −0.207 | 0.620 | −0.386 | −0.057 |

TABLE 2-continued

| Symbol | Day 0 Consensus | Day 7 Consensus | Day 14 Consensus | Day 28 Consensus |
|---|---|---|---|---|
| COL1A1 | 2.420 | 0.802 | 3.094 | 3.165 |
| COL1A2 | 2.001 | 0.343 | 2.463 | 1.940 |
| COL3A1 | 2.384 | 0.610 | 3.454 | 2.540 |
| COL3A1 | 2.208 | 0.447 | 2.563 | 2.138 |
| COL4A1 | 1.580 | 0.622 | 2.068 | 1.562 |
| COL6A1 | 1.372 | 1.323 | | 2.856 |
| COL6A2 | 0.663 | 0.492 | | 1.907 |
| COL7A1 | −0.628 | −1.174 | −1.503 | −0.257 |
| COL15A1 | | | 2.793 | 2.597 |
| C1NH | 1.190 | | 1.523 | 1.298 |
| CSK | −0.227 | 0.381 | 1.010 | 0.842 |
| CCNA2 | 0.655 | 0.468 | | 0.222 |
| ccnb2 | −0.748 | −0.935 | −2.090 | −0.938 |
| CCND3 | −3.675 | | | −3.205 |
| CDKN1B | 0.111 | −0.417 | −1.055 | −0.696 |
| CSTA | −3.184 | −4.342 | −2.899 | −2.722 |
| CST6 | −2.730 | −2.744 | −2.344 | −1.650 |
| CYP1A2 | −0.024 | −0.500 | −2.384 | −1.405 |
| CYP2D6 | −1.822 | −2.306 | −1.001 | −1.505 |
| DDX5 | 1.707 | | | 0.664 |
| DAPK1 | −0.846 | −1.455 | −2.604 | −1.794 |
| DBI | −1.367 | | −1.453 | −0.537 |
| DPP4 | −3.631 | −3.095 | −3.217 | −3.113 |
| DVL3 | 0.154 | 0.016 | −0.881 | −0.982 |
| DUSP3 | 0.862 | | | |
| DUSP5 | 0.098 | 0.042 | −0.404 | −0.822 |
| DYSF | −0.604 | −0.913 | −0.966 | −1.353 |
| EDN3 | −0.162 | 0.117 | −0.054 | −1.015 |
| EGF | −0.998 | −1.642 | −1.557 | −0.527 |
| HE4 | −0.618 | −1.396 | −2.102 | −1.888 |
| FCAR | −1.589 | −1.547 | −1.910 | −2.128 |
| FCGR1A | −4.445 | −4.266 | −4.519 | −5.396 |
| FCGR3A | 2.311 | | | 2.908 |
| FCGRT | 0.731 | 0.289 | 1.183 | 1.328 |
| FGF1 | −1.159 | −1.875 | −1.122 | −0.578 |
| GAGE1 | −1.056 | 0.843 | 0.878 | 0.549 |

TABLE 2-continued

| Symbol | Day 0 Consensus | Day 7 Consensus | Day 14 Consensus | Day 28 Consensus |
|---|---|---|---|---|
| GPR3 | −0.045 | 0.099 | −0.628 | −0.792 |
| GATA3 | −0.468 | −1.513 | −0.933 | −0.597 |
| GTF3A | −0.058 | 0.099 | −0.744 | −1.074 |
| GLP1R | −1.191 | | | |
| GAA | 0.105 | 0.520 | 1.197 | −0.083 |
| GSTM2 | −0.341 | −0.417 | −1.649 | −1.264 |
| GKP2 | −4.143 | −4.125 | −4.152 | −3.849 |
| GLRA2 | −0.153 | −0.714 | −1.904 | −0.609 |
| GNRHR | −0.088 | −0.280 | −1.028 | −1.144 |
| GRO1 | 2.499 | 2.400 | 3.235 | 3.222 |
| GFI1 | −0.200 | 0.056 | −0.514 | −0.785 |
| HSPA6 | −0.094 | −0.557 | −1.567 | −1.053 |
| HVEC | −0.303 | −0.190 | −0.503 | −0.259 |
| HNRPA1 | −0.138 | −0.425 | −1.783 | −0.280 |
| HNRPD | −3.028 | −2.919 | −2.932 | −2.166 |
| D6S81E | −0.458 | −1.223 | −0.802 | −1.158 |
| HLA-G | 0.598 | 0.407 | 1.217 | 1.647 |
| HLA-G | 0.654 | 0.257 | 0.982 | 1.437 |
| HOXB13 | −2.082 | | | |
| HADHA | 0.390 | 1.044 | | 3.061 |
| HIF1A | 2.485 | | | 0.785 |
| IGHG3 | −1.472 | 1.079 | −1.221 | 1.526 |
| IKBKG | −3.570 | −1.414 | −2.503 | −3.336 |
| ITPR3 | −4.786 | −4.247 | −5.457 | −4.813 |
| ITGA2 | −1.672 | −0.728 | −1.181 | −2.017 |
| ITGA2 | −1.372 | −0.431 | −1.638 | −1.390 |
| ITGA3 | −0.356 | −0.740 | −0.153 | −0.944 |
| ITGA5 | 0.171 | −0.219 | | −0.477 |
| ITGA7 | 1.530 | | | |
| ITGB1 | 1.402 | | | 0.741 |
| ITGB1 | 1.793 | 0.310 | | 0.469 |
| ITGB4 | 0.481 | 0.811 | 0.956 | 1.478 |
| IFNAR2 | −2.058 | −0.902 | −2.014 | −2.061 |
| IFNAR2 | −1.980 | −0.744 | −0.691 | −1.271 |
| IL1RN | −3.721 | −4.304 | −3.915 | −4.216 |
| IL1B | 2.845 | 4.473 | | 3.356 |
| IL1B | 3.565 | 4.437 | 3.485 | 3.858 |
| IL17R | −0.958 | −1.343 | −0.557 | −1.379 |
| IL17R | 0.061 | −0.948 | −0.904 | −0.904 |
| IL3 | −1.050 | −1.006 | −0.388 | −1.587 |
| IL8 | 2.781 | 2.758 | | 1.782 |
| IL8 | 3.225 | 3.154 | | 2.729 |
| KLRC2 | −1.754 | −0.483 | −1.065 | −2.768 |
| LDHA | 0.419 | 0.050 | −0.914 | −0.146 |
| LMNA | −0.725 | −0.422 | −0.360 | −0.387 |
| LIMK1 | −2.876 | −1.452 | −1.931 | −1.867 |
| HML2 | −0.340 | −0.100 | −0.522 | −1.162 |
| MARCO | 0.335 | 1.018 | 1.533 | 1.910 |
| HLA-C | 0.896 | −0.029 | 0.944 | 0.358 |
| MRC1 | 0.705 | 0.335 | | 0.750 |
| M6PR | −1.029 | −1.353 | −1.312 | −0.834 |
| MMP11 | 0.935 | | | −0.059 |
| MMP19 | −2.714 | −3.606 | −3.705 | −3.617 |
| MMP2 | 1.660 | | | 3.534 |
| MRE11B | −0.705 | −1.137 | −0.356 | −0.258 |
| MC1R | −0.209 | 0.088 | −0.779 | −0.458 |
| MBD2 | −0.745 | −1.145 | −0.891 | −1.293 |
| MAP3K10 | −1.203 | −0.798 | −1.227 | 0.060 |
| MYO5A | 0.041 | −0.706 | −2.167 | −1.663 |
| MYBPC3 | −0.695 | −0.624 | 0.234 | 0.817 |
| NAGLU | −1.355 | 0.009 | −2.173 | −1.793 |
| NDUFS6 | −3.276 | −3.228 | −3.295 | −2.853 |
| NCAM1 | −0.804 | −0.764 | 0.268 | −0.978 |
| NAIP | −3.300 | −3.244 | −3.529 | −3.505 |
| NPAS1 | 0.091 | 0.707 | −0.049 | 1.131 |
| NMI | −1.010 | −0.232 | −1.233 | −0.937 |
| NME3 | 1.763 | 1.318 | 1.042 | 3.640 |
| NOTCH3 | −0.479 | −0.677 | −0.909 | −1.373 |
| NFE2 | −1.256 | −1.658 | −2.471 | −1.314 |
| NFX1 | −0.717 | 0.070 | −1.267 | −0.846 |
| PAK1 | −0.913 | −0.889 | −0.969 | −0.827 |
| PAX3 | −1.417 | 1.436 | 0.924 | 0.375 |
| PON1 | −2.045 | −0.886 | −0.520 | −2.501 |
| PTCH | −0.836 | 0.378 | −0.515 | −0.625 |
| FARSL | 0.012 | 0.391 | −1.135 | −0.923 |
| PGK1 | 0.075 | −0.405 | 0.062 | −0.178 |
| PLAUR | 0.319 | 0.501 | −0.464 | −0.226 |
| PM5 | 0.366 | 0.048 | −0.546 | −0.380 |
| KCNK3 | −2.742 | −0.941 | −3.909 | −3.123 |
| KCNJ8 | 0.041 | −0.408 | −0.455 | −0.230 |
| KCNJ4 | 1.403 | 0.809 | 1.744 | 1.557 |
| POU2F1 | −3.198 | −2.780 | −3.130 | −4.266 |
| PTGIR | −3.805 | −3.999 | −3.119 | −2.540 |
| PSMB10 | −0.968 | −0.556 | −0.688 | −1.662 |
| PIASY | −0.307 | −0.690 | −1.477 | −1.186 |
| PPP2R4 | 0.307 | 0.184 | 0.239 | 1.623 |
| PTP4A3 | −0.629 | −2.417 | −1.787 | −1.300 |
| PTPRN | −0.559 | −0.061 | −1.230 | −0.665 |
| PLP2 | | 1.436 | | 3.611 |
| P2RY2 | −1.210 | −1.726 | −2.091 | −2.297 |
| QSCN6 | −1.797 | | | −1.673 |
| RIPK1 | −0.385 | 0.104 | 0.324 | −0.327 |
| RPL10 | −1.250 | −1.274 | −1.301 | −0.182 |
| RPS15 | −0.188 | −0.899 | −1.412 | −0.396 |
| RYR1 | −0.663 | −0.463 | −1.862 | −1.103 |
| SPARC | 2.027 | 1.351 | 1.894 | 3.147 |
| SDCCAG10 | −0.319 | −0.617 | −3.338 | −0.147 |
| SH3GL1 | −1.497 | −0.544 | −1.765 | −1.649 |
| SCYA3 | 0.060 | 0.465 | −1.162 | −1.039 |
| SCYA11 | 1.380 | 2.552 | | 4.208 |
| SCYA18 | | | 3.293 | |
| SNRPA1 | −1.533 | −1.784 | −2.249 | −2.681 |
| SLC15A1 | −0.135 | 1.009 | 0.089 | 2.950 |
| SATB1 | −1.005 | −0.185 | −1.922 | −1.551 |
| SYP | −2.620 | −1.482 | −3.638 | −3.073 |
| TAL1 | −2.437 | 1.430 | 2.300 | 1.477 |
| G22P1 | −1.145 | −2.975 | −3.654 | −3.143 |
| TIMP1 | 2.482 | 1.721 | 2.496 | 1.771 |
| TIMP2 | −1.282 | −0.681 | −0.312 | −0.530 |
| TIMP3 | 0.817 | −0.133 | | −0.115 |
| TGFBR3 | −2.315 | −1.924 | −2.838 | −2.883 |
| TGFBI | 0.378 | 1.679 | | 2.947 |
| TNFRSF1A | 0.724 | 0.292 | 0.777 | 0.051 |
| TNFRSF1B | −0.614 | −1.166 | −1.401 | −1.444 |
| UBTF | −0.315 | −0.965 | −1.061 | 0.179 |
| scn8a | −0.694 | −0.277 | −1.247 | −1.451 |
| XRCC2 | −1.109 | −1.481 | −1.685 | −2.431 |

In general, the expression levels of the following genes were increased in wound tissues relative to healthy tissues: interleukins (about 11-fold to 15-fold increase), growth factors (about 6-fold to 7-fold increase) and collagens (about 3-fold to about 7-fold increase). In contrast, the expression levels of following genes were reduced in wound tissues relative to healthy tissues: angiotensin II receptor (about 52-fold decrease), inositol triphosphate receptor 3 (about 26-fold decrease) and interleukin I receptor antagonist (about 17-fold decrease).

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed:

1. A method comprising
quantifying expression levels of one or more genes in a wound tissue sample from a wound of a mammalian subject, the wound being at least 7 days old, the one or more genes consisting of one or more of angiotensin II receptor, interleukin I receptor antagonist or inositol triphosphate receptor 3, the expression level being quantified by highly stringent hybridization of RNA obtained from the wound tissue sample to a probe that is complementary to SEQ ID NO:1, SEQ ID NO:3 or SEQ ID NO:5, wherein the only gene expression levels quantified in the method are one or more of angiotensin II receptor, interleukin I receptor antagonist and inositol triphosphate receptor 3, and wherein the expression level of inositol triphosphate receptor 3 is quantified; and
comparing the expression level of the angiotensin II receptor, interleukin I receptor antagonist or inositol triphosphate receptor 3 of the wound tissue sample with another expression level of angiotensin II receptor, interleukin I receptor antagonist or inositol triphosphate receptor 3 in tissue of the same type from the mammalian subject.

2. The method of claim 1, wherein the mammalian subject is a human subject.

3. The method of claim 1, wherein the hybridization comprises hybridization of the wound tissue sample RNA to an array of probes complementary to SEQ ID NO:5.

4. The method of claim 3, wherein the hybridization further comprises hybridization of the wound tissue sample RNA to an array of probes complementary to SEQ ID NO:1 or SEQ ID NO:3.

5. The method of claim 1, wherein the hybridization comprises hybridization of a northern blot of the wound tissue sample RNA to probes complementary to SEQ ID NO:5.

6. The method of claim 5, wherein the hybridization further comprises hybridization of a northern blot of the wound tissue sample RNA to probes complementary to SEQ ID NO:1 or SEQ ID NO:3.

7. A method comprising
quantifying expression levels of genes in a wound tissue sample from a wound of a mammalian subject, the wound being at least 7 days old, the genes consisting of angiotensin II receptor, interleukin I receptor antagonist, and inositol triphosphate receptor 3, the expression level being quantified by highly stringent hybridization of RNA obtained from the wound tissue sample to probes that are complementary to SEQ ID NO:1, SEQ ID NO:3 and SEQ ID NO:5, wherein the only gene expression levels quantified in the method are angiotensin II receptor, interleukin I receptor antagonist and inositol triphosphate receptor 3, and
comparing the expression level of the angiotensin II receptor, interleukin I receptor antagonist and inositol triphosphate receptor 3 of the wound tissue sample with another expression level of angiotensin II receptor, interleukin I receptor antagonist and inositol triphosphate receptor 3 in tissue of the same type from the mammalian subject.

8. A method comprising
quantifying expression levels of one or more genes in a wound tissue sample from a wound of a mammalian subject, the wound being at least 7 days old, the one or more genes consisting of angiotensin II receptor, interleukin I receptor antagonist or inositol triphosphate receptor 3, the expression level being quantified by amplification of RNA obtained from the wound tissue sample using primers complementary to, and that selectively hybridize to, SEQ ID NO:1, SEQ ID NO:3 or SEQ ID NO:5, wherein the only gene expression levels quantified in the method are one or more of angiotensin II receptor, interleukin I receptor antagonist and inositol triphosphate receptor 3, and wherein the expression level of inositol triphosphate receptor 3 is quantified, and
comparing the expression level of the angiotensin II receptor, interleukin I receptor antagonist or inositol triphosphate receptor 3 of the wound tissue sample with another expression level of angiotensin II receptor, interleukin I receptor antagonist or inositol triphosphate receptor 3 in tissue of the same type from the mammalian subject.

9. A method comprising
obtaining a tissue biopsy from a wound tissue, the wound tissue being from a wound that is at least 7 days old;
homogenizing the tissue biopsy;
extracting mRNA from the homogenized tissue biopsy;
hybridizing the mRNA to a probe that is complementary to SEQ ID NO:1, SEQ ID NO:3, or SEQ ID NO: 5, wherein the mRNA is hybridized to the probe under highly stringent hybridization conditions; and
quantifying the expression levels of one or more genes in the wound tissue, the one or more genes consisting of angiotensin II receptor, interleukin I receptor antagonist or inositol triphosphate receptor 3, wherein the only expression levels quantified in the method are one or more of angiotensin II receptor, interleukin I receptor antagonist or inositol triphosphate receptor 3, and wherein the expression level of inositol triphosphate receptor 3 is quantified.

10. The method of claim 9, wherein the wound tissue is from a mammalian subject.

11. The method of claim 10, wherein the mammalian subject is a human subject.

12. The method of claim 9, wherein the hybridization comprises hybridization of the wound tissue sample RNA to an array of probes complementary to SEQ ID NO:5.

13. The method of claim 12, wherein the hybridization further comprises hybridization of the wound tissue sample RNA to an array of probes complementary to SEQ ID NO:1 or SEQ ID NO:3.

14. The method of claim 9, wherein the hybridization comprises hybridization of a northern blot of the wound tissue sample RNA to probes complementary to SEQ ID NO:5.

15. The method of claim 14, wherein the hybridization further comprises hybridization of a northern blot of the wound tissue sample RNA to probes complementary to SEQ ID NO:1 or SEQ ID NO:3.

16. A method comprising
obtaining a tissue biopsy from a wound tissue, the wound tissue being from a wound that is at least 7 days old;
homogenizing the tissue biopsy;
extracting mRNA from the homogenized tissue biopsy;
hybridizing the mRNA to probes that are complementary to SEQ ID NO:1, SEQ ID NO:3, and SEQ ID NO: 5, wherein the mRNA is hybridized to the probes under highly stringent hybridization conditions; and
quantifying expression levels of genes in the wound tissue, the genes consisting of angiotensin II receptor, interleukin I receptor antagonist, and inositol triphosphate receptor 3, wherein the only expression levels quantified in the method are angiotensin II receptor, interleukin I receptor antagonist and inositol triphosphate receptor 3.

17. A method comprising obtaining a tissue biopsy from a wound tissue, the wound tissue being from a wound that is at least 7 days old;

homogenizing the tissue biopsy;

extracting mRNA from the homogenized tissue biopsy;

amplifying the mRNA obtained from the wound using primers that are complementary to SEQ ID NO:1, SEQ ID NO:3, or SEQ ID NO: 5, wherein the primers selectively hybridize to SEQ ID NO:1, SEQ ID NO:3, or SEQ ID NO:5; and quantifying expression levels of one or more genes in the wound tissue, the one or more genes consisting of angiotensin II receptor, interleukin I receptor antagonist or inositol triphosphate receptor 3, wherein the only expression revels quantified in the method are one or more of angiotensin II receptor, interleukin I receptor antagonist and inositol triphosphate receptor 3, and wherein the expression level of inositol triphosphate receptor 3 is quantified.

* * * * *

SEQUENCE LISTING

```
<160> NUMBER OF SEQ ID NOS: 6

<210> SEQ ID NO 1
<211> LENGTH: 2338
<212> TYPE: DNA
<213> ORGANISM: Homo sapiens

<400> SEQUENCE: 1
gattccagcg cctgacagcc aggaccccag gcagcagcga gtgacaggac gtctggaccg      60
gcgcgccgct agcagctctg ccgggccgcg gcggtgatcg atggggagcg gctggagcgg     120
acccagcgag tgagggcgca cagccgggac gccgaggcgg cgggcgggag acccgcacca     180
gcgcagccgg ccctcggcgg gacgtgacgc agcgcccggg gcgcgggttt gatatttgac     240
aaattgatct aaaatggctg ggttttatc tgaataactc actgatgcca tcccagaaag      300
tcggcaccag gtgtatttga tatagtgttt gcaacaaatt cgacccaggt gatcaaaatg     360
attctcaact cttctactga agatggtatt aaaagaatcc aagatgattg tcccaaagct     420
ggaaggcata attacatatt tgtcatgatt cctactttat acagtatcat ctttgtggtg     480
ggaatatttg gaaacagctt ggtggtgata gtcatttact tttatatgaa gctgaagact     540
gtggccagtg tttttctttt gaatttagca ctggctgact tatgcttttt actgactttg     600
ccactatggg ctgtctacac agctatggaa taccgctggc cctttggcaa ttacctatgt     660
aagattgctt cagccagcgt cagtttcaac ctgtacgcta gtgtgtttct actcacgtgt     720
ctcagcattg atcgatacct ggctattgtt cacccaatga agtcccgcct tcgacgcaca     780
atgcttgtag ccaaagtcac ctgcatcatc atttggctgc tggcaggctt ggccagtttg     840
ccagctataa tccatcgaaa tgtatttttc attgagaaca ccaatattac agtttgtgct     900
ttccattatg agtcccaaaa ttcaaccctc ccgatagggc tgggcctgac caaaaatata     960
ctgggtttcc tgtttccttt tctgatcatt cttacaagtt atactcttat ttggaaggcc    1020
ctaaagaggg cttatgaaat tcagaagaac aaaccaagaa atgatgatat ttttaagata    1080
attatggcaa ttgtgctttt ctttttcttt tcctggattc cccaccaaat attcactttt    1140
```

```
ctggatgtat tgattcaact aggcatcata cgtgactgta gaattgcaga tattgtggac    1200
acggccatgc ctatcaccat ttgtatagct tattttaaca attgcctgaa tcctcttttt    1260
tatggctttc tggggaaaaa atttaaaaga tattttctcc agcttctaaa atatattccc    1320
ccaaaagcca aatcccactc aaacctttca acaaaaatga gcacgctttc ctaccgcccc    1380
tcagataatg taagctcatc caccaagaag cctgcaccat gttttgaggt tgagtgacat    1440
gttcgaaacc tgtccataaa gtaattttgt gaagaagga gcaagagaac attcctctgc     1500
agcacttcac taccaaatga gccttagcta cttttcagaa ttgaaggaga aaatgcatta    1560
tgtggactga accgactttt ctaaagctct gaacaaaagc ttttctttcc ttttgcaaca    1620
agacaaagca aagccacatt tgcattaga cagatgacgg ctgctcgaag aacaatgtca     1680
gaaactcgat gaatgtgttg atttgagaaa ttttactgac agaaatgcaa tctccctagc    1740
ctgcttttgt cctgttattt tttatttcca cataaaggta tttagaatat attaaatcgt    1800
tagaggagca acaggagatg agagttccag attgttctgt ccagtttcca aagggcagta    1860
aagttttcgt gccggttttc agctattagc aactgtgcta cacttgcacc tggtactgca    1920
cattttgtac aaagatatgc taagcagtag tcgtcaagtt gcagatcttt ttgtgaaatt    1980
caacctgtgt cttataggtt tacactgcca aaacaatgcc cgtaagatgg cttatttgta    2040
taatggtgtt actaaagtca catataaaag ttaaactact tgtaaaggtg ctgcactggt    2100
cccaagtagt agtgtcttcc tagtatatta gtttgattta atatctgaga agtgtatata    2160
gtttgtggta aaaagattat atatcataaa gtatgccttc ctgtttaaaa aaagtatata    2220
ttctacacat atatatat gtatatctat atctctaaac tgctgttaat tgattaaaat      2280
ctggcaaagt tatatttact ttaaaataaa ataattttat tgcaaaaaaa aaaaaaaa     2338
```

<210> SEQ ID NO 2
<211> LENGTH: 359
<212> TYPE: PRT
<213> ORGANISM: Homo sapiens

<400> SEQUENCE: 2

```
Met Ile Leu Asn Ser Ser Thr Glu Asp Gly Ile Lys Arg Ile Gln Asp
 1               5                  10                  15

Asp Cys Pro Lys Ala Gly Arg His Asn Tyr Ile Phe Val Met Ile Pro
             20                  25                  30

Thr Leu Tyr Ser Ile Ile Phe Val Val Gly Ile Phe Gly Asn Ser Leu
         35                  40                  45

Val Val Ile Val Ile Tyr Phe Tyr Met Lys Leu Lys Thr Val Ala Ser
     50                  55                  60

Val Phe Leu Leu Asn Leu Ala Leu Ala Asp Leu Cys Phe Leu Leu Thr
 65                  70                  75                  80

Leu Pro Leu Trp Ala Val Tyr Thr Ala Met Glu Tyr Arg Trp Pro Phe
                 85                  90                  95

Gly Asn Tyr Leu Cys Lys Ile Ala Ser Ala Ser Val Ser Phe Asn Leu
            100                 105                 110

Tyr Ala Ser Val Phe Leu Leu Thr Cys Leu Ser Ile Asp Arg Tyr Leu
        115                 120                 125

Ala Ile Val His Pro Met Lys Ser Arg Leu Arg Arg Thr Met Leu Val
    130                 135                 140

Ala Lys Val Thr Cys Ile Ile Ile Trp Leu Leu Ala Gly Leu Ala Ser
145                 150                 155                 160

Leu Pro Ala Ile Ile His Arg Asn Val Phe Phe Ile Glu Asn Thr Asn
                165                 170                 175
```

```
Ile Thr Val Cys Ala Phe His Tyr Glu Ser Gln Asn Ser Thr Leu Pro
            180                 185                 190

Ile Gly Leu Gly Leu Thr Lys Asn Ile Leu Gly Phe Leu Phe Pro Phe
        195                 200                 205

Leu Ile Ile Leu Thr Ser Tyr Thr Leu Ile Trp Lys Ala Leu Lys Arg
210                 215                 220

Ala Tyr Glu Ile Gln Lys Asn Lys Pro Arg Asn Asp Ile Phe Lys
225                 230                 235                 240

Ile Ile Met Ala Ile Val Leu Phe Phe Phe Ser Trp Ile Pro His
                245                 250                 255

Gln Ile Phe Thr Phe Leu Asp Val Leu Ile Gln Leu Gly Ile Ile Arg
                260                 265                 270

Asp Cys Arg Ile Ala Asp Ile Val Asp Thr Ala Met Pro Ile Thr Ile
                275                 280                 285

Cys Ile Ala Tyr Phe Asn Asn Cys Leu Asn Pro Leu Phe Tyr Gly Phe
            290                 295                 300

Leu Gly Lys Lys Phe Lys Arg Tyr Phe Leu Gln Leu Leu Lys Tyr Ile
305                 310                 315                 320

Pro Pro Lys Ala Lys Ser His Ser Asn Leu Ser Thr Lys Met Ser Thr
                    325                 330                 335

Leu Ser Tyr Arg Pro Ser Asp Asn Val Ser Ser Thr Lys Lys Pro
                340                 345                 350

Ala Pro Cys Phe Glu Val Glu
        355

<210> SEQ ID NO 3
<211> LENGTH: 1684
<212> TYPE: DNA
<213> ORGANISM: Homo sapiens

<400> SEQUENCE: 3
ccgacagaat ggaaatctgc agaggcctcc gcagtcacct aatcactctc ctcctcttcc      60
tgttccattc agagacgatc tgccgaccct ctgggagaaa atccagcaag atgcaagcct     120
tcagaatctg ggatgttaac cagaagacct tctatctgag gaacaaccaa ctagttgctg     180
gatacttgca aggaccaaat gtcaatttag aagaaaagat agatgtggta cccattgagc     240
ctcatgctct gttcttggga atccatggag ggagatgtgt cctgtcctgt gtcaagtctg     300
gtgatgagac cagactccag ctggaggcag ttaacatcac tgacctgagc gagaacagaa     360
agcaggacaa gcgcttcgcc ttcatccgct cagacagtgg ccccaccacc agttttgagt     420
ctgccgcctg ccccggttgg ttcctctgca cagcgatgga agctgaccag cccgtcagcc     480
tcaccaatat gcctgacgaa ggcgtcatgg tcaccaaatt ctacttccag gaggacgagt     540
agtactgccc aggcctgcct gttcccattc ttgcatggca aggactgcag ggactgccag     600
tccccctgcc ccagggctcc cggctatggg ggcactgagg accagccatt gaggggtgga     660
ccctcagaag gcgtcacaac aacctggtca caggactctg cctcctcttc aactgaccag     720
cctccatgct gcctccagaa tggtcttttct aatgtgtgaa tcagagcaca gcagccctg     780
cacaaagccc ttccatgtcg cctctgcatt caggatcaaa ccccgaccac ctgcccaacc     840
tgtctcctct tgccactgcc tcttcctccc tcattccacc ttcccatgcc ctggatccat     900
caggccactt gatgaccccc aaccaagtgg ctcccacacc ctgttttaca aaaaagaaaa     960
gaccagtcca tgagggaggt ttttaagggt ttgtggaaaa tgaaaattag gatttcatga    1020
tttttttttt tcagtccccg tgaaggagag cccttcattt ggagattatg ttctttcggg    1080
```

```
gagaggctga ggacttaaaa tattcctgca tttgtgaaat gatggtgaaa gtaagtggta    1140
gcttttccct tcttttttctt ctttttttgt gatgtcccaa cttgtaaaaa ttaaaagtta   1200
tggtactatg ttagcccccca taatttttt tttccttta aaacacttcc ataatctgga    1260
ctcctctgtc caggcactgc tgcccagcct ccaagctcca tctccactcc agattttta    1320 cagctgcctg cagtacttta cctcctatca gaagtttctc agctcccaag gctctgagca   1380
aatgtggctc ctgggggttc tttcttcctc tgctgaagga ataaattgct ccttgacatt   1440
gtagagcttc tggcacttgg agacttgtat gaaagatggc tgtgcctctg cctgtctccc   1500
ccaccaggct gggagctctg cagagcagga acatgactc gtatatgtct caggtccctg    1560
cagggccaag cacctaccct cgctcttggc aggtactcag cgaatgaatg ctgtatatgt   1620
tgggtgcaaa gttccctact tcctgtgact tcagctctgt tttacaataa aatcttaaaa   1680
tgcc                                                                1684
```

<210> SEQ ID NO 4
<211> LENGTH: 177
<212> TYPE: PRT
<213> ORGANISM: Homo sapiens

<400> SEQUENCE: 4

```
Met Glu Ile Cys Arg Gly Leu Arg Ser His Leu Ile Thr Leu Leu Leu
 1               5                  10                  15

Phe Leu Phe His Ser Glu Thr Ile Cys Arg Pro Ser Gly Arg Lys Ser
                20                  25                  30

Ser Lys Met Gln Ala Phe Arg Ile Trp Asp Val Asn Gln Lys Thr Phe
            35                  40                  45

Tyr Leu Arg Asn Asn Gln Leu Val Ala Gly Tyr Leu Gln Gly Pro Asn
        50                  55                  60

Val Asn Leu Glu Glu Lys Ile Asp Val Val Pro Ile Glu Pro His Ala
 65                  70                  75                  80

Leu Phe Leu Gly Ile His Gly Gly Lys Met Cys Leu Ser Cys Val Lys
                85                  90                  95

Ser Gly Asp Glu Thr Arg Leu Gln Leu Glu Ala Val Asn Ile Thr Asp
            100                 105                 110

Leu Ser Glu Asn Arg Lys Gln Asp Lys Arg Phe Ala Phe Ile Arg Ser
        115                 120                 125

Asp Ser Gly Pro Thr Thr Ser Phe Glu Ser Ala Ala Cys Pro Gly Trp
    130                 135                 140

Phe Leu Cys Thr Ala Met Glu Ala Asp Gln Pro Val Ser Leu Thr Asn
145                 150                 155                 160

Met Pro Asp Glu Gly Val Met Val Thr Lys Phe Tyr Phe Gln Glu Asp
                165                 170                 175

Glu
```

<210> SEQ ID NO 5
<211> LENGTH: 8833
<212> TYPE: DNA
<213> ORGANISM: Homo sapiens

<400> SEQUENCE: 5

```
cgccccccac gccctgggcc ccggagggcc gcagccatga gtgaaatgtc cagctttctt      60
cacatcgggg acatcgtctc cctgtacgcc gagggctccg tcaatggctt catcagcact    120
ttggggctgg tggatgaccg ctgtgtggtg gagcccgcgg ccggggacct ggacaacccc    180
```

-continued

```
cctaagaagt tccgtgactg cctcttcaag gtgtgcccca tgaaccgcta ctcggcccag     240
aagcagtact ggaaggccaa gcagactaag caggacaagg agaagatcgc tgatgtggtg     300
ttgctgcaga agctgcagca tgcggcgcag atggagcaga agcaaaatga cacggagaac     360
aagaaggtgc atggggatgt cgtgaagtat ggcagtgtga tccagctcct gcacatgaag     420
agcaacaagt acctgacagt gaacaagcgg cttccggcct tgctggagaa gaacgccatg     480
cgggtgactc tggatgccac aggcaacgag ggttcctggc tcttcatcca gcccttctgg     540
aagctgcgga gcaacgggga caacgtggtc gtggggacaa aggtgatcct gaatcctgtc     600
aatgccgggc agcctctgca tgccagcaat tacgagctca gcgacaacgc cggctgcaag     660
gaggtcaatt ctgtgaactg caacaccagc tggaagatca acctgtttat gcagtttcgg     720
gaccacctgg aggaggtgtt gaaggggga gacgtggtgc ggctgttcca tgcggagcag     780
gagaagttcc tgacgtgtga cgagtacaag ggcaagctgc aggtgttcct gcgaactaca     840
ctgcgccagt ctgccacctc ggccaccagc tccaatgctc tctgggaggt ggaggtggtc     900
caccacgacc cctgccgtgg aggagctggg cactggaatg gcttgtaccg cttcaagcac     960
ctggctacag gcaactacct ggctgctgag gagaacccca gttacaaagg tgatgcctca    1020
gatcccaagg cagcaggaat gggggcacag ggccgcacag gccgcaggaa tgctggggag    1080
aagatcaagt actgcctggt ggctgtgcct catggcaatg acatcgcctc tctcttttgag    1140 ctggacccca ccaccttgca gaaaaccgac tctttcgtgc cccggaactc gtacgtccgg    1200
ctgcggcacc tctgcaccaa cacgtggatt cagagcacca atgtgcccat tgacatcgag    1260
gaggagcggc ccatccggct catgctgggc acctgcccca caaggagga caaggaggcc    1320 tttgccatcg tgtcagtgcc cgtgtctgag atccgagacc tggactttgc caatgacgcc    1380
agctccatgc tggccagtgc cgtggagaaa ctcaacgagg gcttcatcag ccagaatgac    1440
cgcaggtttg tcatccagct gctggaagac ctggtgttct ttgtcagcga tgtccccaac    1500
aatgggcaga atgtcctgga catcatggtc actaagccca accgggaacg gcagaagctg    1560
atgagggagc agaacatcct caaacaggtc tttggcattc tgaaggtccc gttccgtgag    1620 aagggggggtg aaggtcccct ggtgcggctg gaggagctgt cagaccagaa gaacgccccc    1680
taccagcaca tgttccgcct gtgctaccgt gtgttgcggt attcccagga ggactaccgc    1740
aagaaccagg agcacattgc caagcagttt gggatgatgc agtcccagat ggctacgac     1800 atcctggccg aggacaccat cactgccctg ctgcacaaca accgcaagct cctggaaaag    1860
cacatcacca gaccgaggt ggagaccttc gtcagccttg tgcgcaagaa ccgggagccc    1920
aggttcctgg actacctctc tgacctgtgt gtgtccaacc acatcgccat ccccgtcacc    1980
caagagctca tctgcaagtg tgtgctggac cccaagaaca gtgacattct catccggacc    2040
gagcttcggc ccgtgaagga gatggcccaa tcccacgagt acctgagcat cgagtactca    2100
gaagaggaag tgtggctcac gtggactgac aagaataacg agcatcatga aagagtgtg     2160 aggcagctgg cccaggaggc gcgggccggc aacgcccacg acgagaatgt gctcagctac    2220
tacaggtacc agctgaagct ctttgcccgc atgtgcttgg accgccagta cttggccatc    2280
gacgagatct cccagcagct gggcgtggac ctgatttttcc tgtgcatggc agacgagatg    2340
ctgccctttg acctgcgcgc ctccttctgc cacctgatgc tgcacgtgca cgtggaccgt    2400
gacccccagg agctggtcac gccggtcaag tttgcccgtc tctggactga gatccccaca    2460
gccatcacca tcaaggacta tgattccaac ctcaacgcgt cccgagatga caagaagaac    2520
aagtttgcca acaccatgga gttcgtggag gactacctca caatgtagt cagcgaggcc    2580
```

-continued

```
gtgcccttt g ccaacgagga gaagaacaag ctcactttt g aggtggtcag cctggcgcac   2640
aatctcatct acttcggctt ctacagcttc agcgagctgc tgcggctcac tcgcacactg    2700
ctgggcatca tcgactgtgt gcaggggccc ccggccatgc tgcaggccta tgaggacccc    2760
ggtggcaaga atgtgcggcg gtccatccag ggcgtgggc acatgatgtc caccatggtg     2820
ctgagccgca agcagtccgt cttcagtgcc ccagcctgt ctgctggggc cagtgctgct     2880
gagccgctgg acagaagcaa gttt gaggag aatgaggaca ttgtggtgat ggagaccaag   2940
ctgaagatcc tggaaatcct tcagttcatc ctcaacgtcc gcctggatta ccgcatatcc   3000
tacctgctgt ctgtcttcaa gaaggagttt gtggaggtgt ttcccatgca ggacagtggg   3060
gctgatggca cagcccctgc cttcgactct accactgcca acatgaacct ggatcgcatc   3120
ggggagcagg cggaggccat gtttggagtg gggaagacaa gcagcatgct ggaggtggat   3180
gacgagggcg gccgcatgtt cctgcgcgtg ctcatccacc tcaccatgca cgactatgcg   3240
ccactggtct cgggtgccct gcagctgctc ttcaagcact cagccagcg ccaggaggcc    3300
atgcacacct tcaagcaggt tcagctgctg atctcagcgc aggacgtgga gaactacaag   3360
gtgatcaagt cggagctgga ccggctgcgg accatggtgg agaagtcaga gctgtgggtg   3420
gacaagaagg gcagtggcaa gggtgaggag gtggaggcag gcaccgccaa ggacaagaaa   3480
gagcgtccca cggacgagga gggctttctg cacccaccag gggagaaaag cagtgagaac   3540
taccagatcg tcaagggcat cctggaaagg ctgaacaaga tgtgcggggt tggggagcaa   3600
atgaggaaga agcagcaacg gctgctgaag aacatggatg cccacaaggt catgctggac   3660
ctgctgcaga tccctatga caagggtgat gccaagatga tggagatcct gcgctacacg    3720
caccagttcc tgcagaagtt ctgtgcaggg aaccccggca accaggccct gctgcacaaa   3780
cacctgcacc tcttcctcac gccagggctc ctggaggcag agaccatgca gcacatcttc   3840
ctgaacaact atcagctctg ctccgagatc agcgagcctg tgttgcagca cttcgtgcac   3900
ctgctggcca cgcacgggcg ccatgtgcag tacctggact tcctgcacac cgtcattaag   3960
gccgagggca agtacgtcaa gaagtgccag gacatgatca tgactgagct gaccaatgca   4020
ggtgacgatg tggtcgtgtt ctacaatgat aaggcatcgc tggcccacct gctggacatg   4080
atgaaggccg cccgcgacgg cgtggaggac cacagccccc tcatgtacca catttccctg   4140
gtggacctgc tggccgcctg tgccgagggc aaaaacgtct acactgagat caagtgcacc   4200
tccctcgtgc cgctggagga cgtggtgtct gtggtgacgc atgaggactg catcactgag   4260
gtgaaaatgg cctatgtgaa cttcgtgaac cactgctacg tggacacgga ggtggagatg   4320
aaggagatct acaccagcaa ccacatctgg acgctctttg agaacttcac cctggacatg   4380
gctcgggtct gcagcaagcg tgagaagcgc gtggctgacc ccaccttgga gaagtacgtg   4440
ctgagcgttg tgctggacac catcaacgcc ttcttcagct ccccattctc tgagaacagc   4500
acttccctgc agacacacca gccggttgtg gtgcagctgc tgcagtctac cacacgcctc   4560
ctcgagtgtc cgtggctaca gcagcagcac aagggctccg tggaggcctg catccggacc   4620
ctcgccatgt ggccaagggc ccgggccatc ttgctgccca tggacctgga tgcccacatc   4680
agctcgatgc tcagcagtgg agccagctgt gcagctgccg cccagcggaa cgcctccagc   4740
tacaaggcaa cccgcgggc cttccccgc gtcacccca ccgccaacca gtgggactac     4800
aagaacatca ttgagaagct gcaggacatc atcacagccc tggaggagcg gctgaagccc   4860
ctggtacagg ctgagctgtc cgtgctggtg gatgtcctgc actggcctga gctgctcttc   4920
ctggagggca gtgaggccta ccagcgctgc gagagtgggg gcttcctgtc caagctgatc   4980
```

```
cagcacacca aggacctcat ggagtcggag gagaagctgt gcatcaaggt gctgcggacc    5040
ctgcagcaga tgctcgtcaa gaagaccaag tacggggacc ggggcaacca gctgcgcaag    5100
atgctgctgc aaaactacct ccagaaccgg aagtccacct cgcgggggga ccttcccgac    5160
cccataggca ctggcctgga cccagactgg tcggcaatcg cagccaccca gtgccggctg    5220
gacaaggagg gggccaccaa gttggtatgc gacctcatca ccagcaccaa gaacgagaag    5280
atcttccagg agagcatcgg cctggccatc cacctgctgg atggtggcaa cacagagatc    5340
cagaaatcct tccacaacct gatgatgagt gacaagaagt cagagcgctt cttcaaggtg    5400
ctgcacgacc gcatgaagcg ggcccagcag gagaccaagt ccacggtggc agtcaacatg    5460
aatgacctgg gcagccagcc acatgaggac cgcgagccag tcgaccccac caccaaaggc    5520
cgcgtggcct ccttctcgat acctggctcc tcatcccgct actcgctggg ccccagcctg    5580
cgccgggggc acgaggtgag cgaacgtgtg cagagcagtg agatgggcac atccgtgctc    5640
atcatgcagc ccatcctgcg ctttctgcag ctgctgtgtg agaaccacaa ccgggacctg    5700
cagaacttcc tgcgctgtca gaacaacaaa accaactaca acttggtatg cgagacgctg    5760
cagttcctgg acatcatgtg cggcagcacc acgggcggcc tggggctgct ggggctctac    5820
atcaatgagg acaacgtggg cctcgtcatc cagaccttgg agaccctcac tgagtactgc    5880
cagggcccct gccatgagaa ccagacttgc attgtgactc acgagtccaa tggcatagac    5940
atcatcaccg cactgatcct caatgacatc agccccctgt gcaagtaccg catggatctg    6000
gtgctgcagc tcaaggacaa tgcctccaag ctgctcctgg ctctgatgga gagccggcat    6060
gacagtgaaa atgctgagcg aatcctcatc agcctgcggc cccaggagct ggtggacgtc    6120
atcaagaagg cctacctgca ggaggaagag cgtgagaact cggaggtgag cccacgtgaa    6180
gtgggccata acatctatat cctggcgctg cagctctcca ggcacaataa acagctgcag    6240
cacctgctga gccggtgaa gcgcattcaa gaggaggagg ccgagggtat ctcttccatg    6300
ctcagcctca acaacaagca gctgtcacag atgctcaagt cctcagcgcc agcacaggag    6360
gaggaggaag accccctggc ctactatgag aaccacacgt cccagatcga gattgtgcgg    6420
caggaccgca gcatggagca gatcgtgttc ccagtgcccg gcatctgcca gttcctgacg    6480
gaggaaacca gcaccggct cttcaccact actgagcagg acgagcaggg cagcaaagtg    6540
agcgacttct tcgaccagtc ctccttcctg cacaacgaga tggagtggca gcgcaacgtc    6600
cgcagcatgc gctgatcta ctggttctcc cgccgcatga ccctgtgggg cagcatctcc    6660
ttcaacctgg ccgtgtttat caacatcatc attgccttct tctacccctta catggagggc    6720 gcgtccacag gcgtgctgga ctcccctctc atctcattgc tcttctggat cctcatctgc    6780
ttctccatcg cggccctgtt caccaagcgc tacagcatcc gcccctcat cgtgcgctc    6840 atcctgcgct ccatctacta tctgggcatc gggcccacac tcaacatcct gggtgccctc    6900
aatctgacca caagatcgt gtttgtggtg agcttcgtgg gcaaccgtgg caccttcatc    6960
cggggctata aggccatggt catggacatg gaattcctct accacgtggg ctacatcctg    7020
accagtgtcc tggcctcttt tgctcatgag ctgttctaca gcatcctgct ctttgacctc    7080
atctaccgcg aggagacgct gttcaacgtc atcaagagtg tgacccgcaa tggccgctcc    7140
atcctgctga cagccctgct ggccctcatc ctggtctacc tcttctccat cgtcggcttc    7200
ctcttcctca aggatgactt cattctcgag gtcgaccggc tgcccaacaa ccactccaca    7260 gccagcccc tggggatgcc acatggagct gctgcatttg tggacacctg cagtggggac    7320
aagatggact gtgtctcagg gctctcggtg cctgaggtcc tggaagagga cagggagctg    7380
```

```
gacagcacag agcgggcctg tgacactctg ttgatgtgca tcgtcactgt catgaaccat    7440
gggctacgca acgtggtgg cgtgggcgac attctccgca agccctccaa agatgagtct    7500
ctcttcccag cccgagtggt ctatgacctc ctgttcttct tcatcgtcat catcattgtg    7560
ctgaacctca tctttggggt aatcatcgac accttcgctg acctgcgtag tgagaagcag    7620
aagaaggagg agattcttaa gacgacatgc ttcatctgtg gtctggagag ggacaagttt    7680
gataacaaga cagtgtcatt tgaggaacac atcaagctgg agcacaacat gtggaactac    7740
ttgtacttca ttgtgctggt ccgcgtgaag aacaagaccg actacacggg ccctgagagc    7800
tacgtggccc agatgatcaa gaacaagaac ctggactggt tccccccggat gcgggccatg    7860 tcccttgtca gcaatgaggg cgagggggag cagaatgaga ttcggattct ccaggacaag    7920
ctcaactcca ccatgaagct ggtgtcccac ctcactgccc agctcaacga gctcaaggag    7980
cagatgacgg agcagcggaa acgcaggcaa cgcctaggct ttgtggatgt ccagaactgc    8040
attagccgct gaggagagcc accgaaggcc ccaacagggg atgctcatca ctggagactg    8100
cgactgggaa gaacactgcc ccctccctcg ggttgggtgg cccagccagc tggccagcct    8160
ccactcccac tctgccagac accctgacac ccacccaggc tttgaagagc atggaggggg    8220
agcctcagag ctgacagtcc tgcttagagc ccttaaaaag acttgaaagt tcactgggac    8280
tcagtttacc ttaatgcctt agcagaagat aaatcctacc tagagacctt tgttccttaa    8340
agcaataact gacaactctt tgtagtcctc cttgtgggta gttaagagtg gggtcacccc    8400
tttaactcca agcactacat tttggcggct gcggcctctg ggggaggtgg cagttatgct    8460
gttactagtg attttagggc tttgttattt aacttatttc aagggtgctg tgctcagccc    8520
tgcccatggc tgtgcagctc cctccgtgcc tcagatctgc tgtagccagt gcagacctca    8580
ctgtcgtgtc catgccaccc ccggcatggc tccaggtggc ctggtgactc catgatggac    8640
gatcttgctc ccaggacctg cctcttccca ggcttcctgg ggaagagttg tacgcccagg    8700
caacaagggc tgagctgcgc ttgcgtggct gtttcatgac cgcttgtttt tctccttttg    8760
gtgtaatgtt ttacaaatcc tttggcctga gaactaatat gttaattgcc ttaaataaat    8820
taatagaaat cta                                                      8833
```

<210> SEQ ID NO 6
<211> LENGTH: 2671
<212> TYPE: PRT
<213> ORGANISM: Homo sapiens

<400> SEQUENCE: 6

```
Met Ser Glu Met Ser Ser Phe Leu His Ile Gly Asp Ile Val Ser Leu
 1               5                  10                  15

Tyr Ala Glu Gly Ser Val Asn Gly Phe Ile Ser Thr Leu Gly Leu Val
             20                  25                  30

Asp Asp Arg Cys Val Val Glu Pro Ala Gly Asp Leu Asp Asn Pro
         35                  40                  45

Pro Lys Lys Phe Arg Asp Cys Leu Phe Lys Val Cys Pro Met Asn Arg
     50                  55                  60

Tyr Ser Ala Gln Lys Gln Tyr Trp Lys Ala Lys Gln Thr Lys Gln Asp
 65                  70                  75                  80

Lys Glu Lys Ile Ala Asp Val Val Leu Leu Lys Leu Gln His Ala
                 85                  90                  95

Ala Gln Met Glu Gln Lys Gln Asn Asp Thr Glu Asn Lys Lys Val His
            100                 105                 110

Gly Asp Val Val Lys Tyr Gly Ser Val Ile Gln Leu Leu His Met Lys
```

```
                    115                 120                 125
Ser Asn Lys Tyr Leu Thr Val Asn Lys Arg Leu Pro Ala Leu Leu Glu
130                 135                 140

Lys Asn Ala Met Arg Val Thr Leu Asp Ala Thr Gly Asn Glu Gly Ser
145                 150                 155                 160

Trp Leu Phe Ile Gln Pro Phe Trp Lys Leu Arg Ser Asn Gly Asp Asn
                165                 170                 175

Val Val Val Gly Asp Lys Val Ile Leu Asn Pro Val Asn Ala Gly Gln
            180                 185                 190

Pro Leu His Ala Ser Asn Tyr Glu Leu Ser Asp Asn Ala Gly Cys Lys
        195                 200                 205

Glu Val Asn Ser Val Asn Cys Asn Thr Ser Trp Lys Ile Asn Leu Phe
210                 215                 220

Met Gln Phe Arg Asp His Leu Glu Glu Val Leu Lys Gly Gly Asp Val
225                 230                 235                 240

Val Arg Leu Phe His Ala Glu Gln Glu Lys Phe Leu Thr Cys Asp Glu
                245                 250                 255

Tyr Lys Gly Lys Leu Gln Val Phe Leu Arg Thr Thr Leu Arg Gln Ser
            260                 265                 270

Ala Thr Ser Ala Thr Ser Ser Asn Ala Leu Trp Glu Val Glu Val Val
        275                 280                 285

His His Asp Pro Cys Arg Gly Gly Ala Gly His Trp Asn Gly Leu Tyr
290                 295                 300

Arg Phe Lys His Leu Ala Thr Gly Asn Tyr Leu Ala Ala Glu Glu Asn
305                 310                 315                 320

Pro Ser Tyr Lys Gly Asp Ala Ser Asp Pro Lys Ala Ala Gly Met Gly
                325                 330                 335

Ala Gln Gly Arg Thr Gly Arg Asn Ala Gly Glu Lys Ile Lys Tyr
            340                 345                 350

Cys Leu Val Ala Val Pro His Gly Asn Asp Ile Ala Ser Leu Phe Glu
        355                 360                 365

Leu Asp Pro Thr Thr Leu Gln Lys Thr Asp Ser Phe Val Pro Arg Asn
370                 375                 380

Ser Tyr Val Arg Leu Arg His Leu Cys Thr Asn Thr Trp Ile Gln Ser
385                 390                 395                 400

Thr Asn Val Pro Ile Asp Ile Glu Glu Arg Pro Ile Arg Leu Met
                405                 410                 415

Leu Gly Thr Cys Pro Thr Lys Glu Asp Lys Glu Ala Phe Ala Ile Val
            420                 425                 430

Ser Val Pro Val Ser Glu Ile Arg Asp Leu Asp Phe Ala Asn Asp Ala
        435                 440                 445

Ser Ser Met Leu Ala Ser Ala Val Glu Lys Leu Asn Glu Gly Phe Ile
450                 455                 460

Ser Gln Asn Asp Arg Arg Phe Val Ile Gln Leu Glu Asp Leu Val
465                 470                 475                 480

Phe Phe Val Ser Asp Val Pro Asn Asn Gly Gln Asn Val Leu Asp Ile
                485                 490                 495

Met Val Thr Lys Pro Asn Arg Glu Arg Gln Lys Leu Met Arg Glu Gln
            500                 505                 510

Asn Ile Leu Lys Gln Val Phe Gly Ile Leu Lys Val Pro Phe Arg Glu
        515                 520                 525

Lys Gly Gly Glu Gly Pro Leu Val Arg Leu Glu Glu Leu Ser Asp Gln
530                 535                 540
```

-continued

```
Lys Asn Ala Pro Tyr Gln His Met Phe Arg Leu Cys Tyr Arg Val Leu
545                 550                 555                 560

Arg Tyr Ser Gln Glu Asp Tyr Arg Lys Asn Gln Glu His Ile Ala Lys
            565                 570                 575

Gln Phe Gly Met Met Gln Ser Gln Ile Gly Tyr Asp Ile Leu Ala Glu
            580                 585                 590

Asp Thr Ile Thr Ala Leu Leu His Asn Asn Arg Lys Leu Leu Glu Lys
            595                 600                 605

His Ile Thr Lys Thr Glu Val Glu Thr Phe Val Ser Leu Val Arg Lys
610                 615                 620

Asn Arg Glu Pro Arg Phe Leu Asp Tyr Leu Ser Asp Leu Cys Val Ser
625                 630                 635                 640

Asn His Ile Ala Ile Pro Val Thr Gln Glu Leu Ile Cys Lys Cys Val
            645                 650                 655

Leu Asp Pro Lys Asn Ser Asp Ile Leu Ile Arg Thr Glu Leu Arg Pro
            660                 665                 670

Val Lys Glu Met Ala Gln Ser His Glu Tyr Leu Ser Ile Glu Tyr Ser
            675                 680                 685

Glu Glu Glu Val Trp Leu Thr Trp Thr Asp Lys Asn Asn Glu His His
690                 695                 700

Glu Lys Ser Val Arg Gln Leu Ala Gln Glu Ala Arg Ala Gly Asn Ala
705                 710                 715                 720

His Asp Glu Asn Val Leu Ser Tyr Tyr Arg Tyr Gln Leu Lys Leu Phe
            725                 730                 735

Ala Arg Met Cys Leu Asp Arg Gln Tyr Leu Ala Ile Asp Glu Ile Ser
            740                 745                 750

Gln Gln Leu Gly Val Asp Leu Ile Phe Leu Cys Met Ala Asp Glu Met
            755                 760                 765

Leu Pro Phe Asp Leu Arg Ala Ser Phe Cys His Leu Met Leu His Val
            770                 775                 780

His Val Asp Arg Asp Pro Gln Glu Leu Val Thr Pro Val Lys Phe Ala
785                 790                 795                 800

Arg Leu Trp Thr Glu Ile Pro Thr Ala Ile Thr Ile Lys Asp Tyr Asp
            805                 810                 815

Ser Asn Leu Asn Ala Ser Arg Asp Asp Lys Lys Asn Lys Phe Ala Asn
            820                 825                 830

Thr Met Glu Phe Val Glu Asp Tyr Leu Asn Asn Val Val Ser Glu Ala
            835                 840                 845

Val Pro Phe Ala Asn Glu Glu Lys Asn Lys Leu Thr Phe Glu Val Val
850                 855                 860

Ser Leu Ala His Asn Leu Ile Tyr Phe Gly Phe Tyr Ser Phe Ser Glu
865                 870                 875                 880

Leu Leu Arg Leu Thr Arg Thr Leu Leu Gly Ile Ile Asp Cys Val Gln
            885                 890                 895

Gly Pro Pro Ala Met Leu Gln Ala Tyr Glu Asp Pro Gly Gly Lys Asn
            900                 905                 910

Val Arg Arg Ser Ile Gln Gly Val Gly His Met Met Ser Thr Met Val
            915                 920                 925

Leu Ser Arg Lys Gln Ser Val Phe Ser Ala Pro Ser Leu Ser Ala Gly
            930                 935                 940

Ala Ser Ala Ala Glu Pro Leu Asp Arg Ser Lys Phe Glu Glu Asn Glu
945                 950                 955                 960

Asp Ile Val Val Met Glu Thr Lys Leu Lys Ile Leu Glu Ile Leu Gln
            965                 970                 975
```

```
Phe Ile Leu Asn Val Arg Leu Asp Tyr Arg Ile Ser Tyr Leu Leu Ser
            980                 985                 990

Val Phe Lys Lys Glu Phe Val Glu Val Phe Pro Met Gln Asp Ser Gly
            995                 1000                1005

Ala Asp Gly Thr Ala Pro Ala Phe Asp Ser Thr Thr Ala Asn Met Asn
            1010                1015                1020

Leu Asp Arg Ile Gly Glu Gln Ala Glu Ala Met Phe Gly Val Gly Lys
1025                1030                1035                1040

Thr Ser Ser Met Leu Glu Val Asp Asp Glu Gly Gly Arg Met Phe Leu
                1045                1050                1055

Arg Val Leu Ile His Leu Thr Met His Asp Tyr Ala Pro Leu Val Ser
                1060                1065                1070

Gly Ala Leu Gln Leu Leu Phe Lys His Phe Ser Gln Arg Gln Glu Ala
            1075                1080                1085

Met His Thr Phe Lys Gln Val Gln Leu Leu Ile Ser Ala Gln Asp Val
            1090                1095                1100

Glu Asn Tyr Lys Val Ile Lys Ser Glu Leu Asp Arg Leu Arg Thr Met
1105                1110                1115                1120

Val Glu Lys Ser Glu Leu Trp Val Asp Lys Gly Ser Gly Lys Gly
                1125                1130                1135

Glu Glu Val Glu Ala Gly Thr Ala Lys Asp Lys Lys Glu Arg Pro Thr
            1140                1145                1150

Asp Glu Glu Gly Phe Leu His Pro Pro Gly Glu Lys Ser Ser Glu Asn
            1155                1160                1165

Tyr Gln Ile Val Lys Gly Ile Leu Glu Arg Leu Asn Lys Met Cys Gly
            1170                1175                1180

Val Gly Glu Gln Met Arg Lys Lys Gln Gln Arg Leu Leu Lys Asn Met
1185                1190                1195                1200

Asp Ala His Lys Val Met Leu Asp Leu Leu Gln Ile Pro Tyr Asp Lys
            1205                1210                1215

Gly Asp Ala Lys Met Met Glu Ile Leu Arg Tyr Thr His Gln Phe Leu
            1220                1225                1230

Gln Lys Phe Cys Ala Gly Asn Pro Gly Asn Gln Ala Leu Leu His Lys
            1235                1240                1245

His Leu His Leu Phe Leu Thr Pro Gly Leu Leu Glu Ala Glu Thr Met
            1250                1255                1260

Gln His Ile Phe Leu Asn Asn Tyr Gln Leu Cys Ser Glu Ile Ser Glu
1265                1270                1275                1280

Pro Val Leu Gln His Phe Val His Leu Leu Ala Thr His Gly Arg His
                1285                1290                1295

Val Gln Tyr Leu Asp Phe Leu His Thr Val Ile Lys Ala Glu Gly Lys
            1300                1305                1310

Tyr Val Lys Lys Cys Gln Asp Met Ile Met Thr Glu Leu Thr Asn Ala
            1315                1320                1325

Gly Asp Asp Val Val Val Phe Tyr Asn Asp Lys Ala Ser Leu Ala His
            1330                1335                1340

Leu Leu Asp Met Met Lys Ala Ala Arg Asp Gly Val Glu Asp His Ser
1345                1350                1355                1360

Pro Leu Met Tyr His Ile Ser Leu Val Asp Leu Leu Ala Ala Cys Ala
                1365                1370                1375

Glu Gly Lys Asn Val Tyr Thr Glu Ile Lys Cys Thr Ser Leu Val Pro
            1380                1385                1390

Leu Glu Asp Val Val Ser Val Val Thr His Glu Asp Cys Ile Thr Glu
```

```
                1395                1400                1405
Val Lys Met Ala Tyr Val Asn Phe Val Asn His Cys Tyr Val Asp Thr
    1410                1415                1420
Glu Val Glu Met Lys Glu Ile Tyr Thr Ser Asn His Ile Trp Thr Leu
1425                1430                1435                1440
Phe Glu Asn Phe Thr Leu Asp Met Ala Arg Val Cys Ser Lys Arg Glu
                1445                1450                1455
Lys Arg Val Ala Asp Pro Thr Leu Glu Lys Tyr Val Leu Ser Val Val
    1460                1465                1470
Leu Asp Thr Ile Asn Ala Phe Phe Ser Ser Pro Phe Ser Glu Asn Ser
            1475                1480                1485
Thr Ser Leu Gln Thr His Gln Pro Val Val Gln Leu Leu Gln Ser
    1490                1495                1500
Thr Thr Arg Leu Leu Glu Cys Pro Trp Leu Gln Gln Gln His Lys Gly
1505                1510                1515                1520
Ser Val Glu Ala Cys Ile Arg Thr Leu Ala Met Val Ala Lys Gly Arg
                1525                1530                1535
Ala Ile Leu Leu Pro Met Asp Leu Asp Ala His Ile Ser Ser Met Leu
            1540                1545                1550
Ser Ser Gly Ala Ser Cys Ala Ala Ala Ala Gln Arg Asn Ala Ser Ser
        1555                1560                1565
Tyr Lys Ala Thr Thr Arg Ala Phe Pro Arg Val Thr Pro Thr Ala Asn
    1570                1575                1580
Gln Trp Asp Tyr Lys Asn Ile Ile Glu Lys Leu Gln Asp Ile Ile Thr
1585                1590                1595                1600
Ala Leu Glu Glu Arg Leu Lys Pro Leu Val Gln Ala Glu Leu Ser Val
                1605                1610                1615
Leu Val Asp Val Leu His Trp Pro Glu Leu Leu Phe Leu Glu Gly Ser
            1620                1625                1630
Glu Ala Tyr Gln Arg Cys Glu Ser Gly Gly Phe Leu Ser Lys Leu Ile
        1635                1640                1645
Gln His Thr Lys Asp Leu Met Glu Ser Glu Glu Lys Leu Cys Ile Lys
    1650                1655                1660
Val Leu Arg Thr Leu Gln Gln Met Leu Val Lys Lys Thr Lys Tyr Gly
1665                1670                1675                1680
Asp Arg Gly Asn Gln Leu Arg Lys Met Leu Leu Gln Asn Tyr Leu Gln
                1685                1690                1695
Asn Arg Lys Ser Thr Ser Arg Gly Asp Leu Pro Asp Pro Ile Gly Thr
            1700                1705                1710
Gly Leu Asp Pro Asp Trp Ser Ala Ile Ala Ala Thr Gln Cys Arg Leu
        1715                1720                1725
Asp Lys Glu Gly Ala Thr Lys Leu Val Cys Asp Leu Ile Thr Ser Thr
    1730                1735                1740
Lys Asn Glu Lys Ile Phe Gln Glu Ser Ile Gly Leu Ala Ile His Leu
1745                1750                1755                1760
Leu Asp Gly Gly Asn Thr Glu Ile Gln Lys Ser Phe His Asn Leu Met
                1765                1770                1775
Met Ser Asp Lys Lys Ser Glu Arg Phe Phe Lys Val Leu His Asp Arg
            1780                1785                1790
Met Lys Arg Ala Gln Gln Glu Thr Lys Ser Thr Val Ala Val Asn Met
        1795                1800                1805
Asn Asp Leu Gly Ser Gln Pro His Glu Asp Arg Glu Pro Val Asp Pro
    1810                1815                1820
```

-continued

Thr Thr Lys Gly Arg Val Ala Ser Phe Ser Ile Pro Gly Ser Ser Ser
1825                1830                1835                1840

Arg Tyr Ser Leu Gly Pro Ser Leu Arg Arg Gly His Glu Val Ser Glu
        1845                1850                1855

Arg Val Gln Ser Ser Glu Met Gly Thr Ser Val Leu Ile Met Gln Pro
        1860                1865                1870

Ile Leu Arg Phe Leu Gln Leu Leu Cys Glu Asn His Asn Arg Asp Leu
        1875                1880                1885

Gln Asn Phe Leu Arg Cys Gln Asn Asn Lys Thr Asn Tyr Asn Leu Val
        1890                1895                1900

Cys Glu Thr Leu Gln Phe Leu Asp Ile Met Cys Gly Ser Thr Thr Gly
1905                1910                1915                1920

Gly Leu Gly Leu Leu Gly Leu Tyr Ile Asn Glu Asp Asn Val Gly Leu
        1925                1930                1935

Val Ile Gln Thr Leu Glu Thr Leu Thr Glu Tyr Cys Gln Gly Pro Cys
        1940                1945                1950

His Glu Asn Gln Thr Cys Ile Val Thr His Glu Ser Asn Gly Ile Asp
        1955                1960                1965

Ile Ile Thr Ala Leu Ile Leu Asn Asp Ile Ser Pro Leu Cys Lys Tyr
        1970                1975                1980

Arg Met Asp Leu Val Leu Gln Leu Lys Asp Asn Ala Ser Lys Leu Leu
1985                1990                1995                2000

Leu Ala Leu Met Glu Ser Arg His Asp Ser Glu Asn Ala Glu Arg Ile
        2005                2010                2015

Leu Ile Ser Leu Arg Pro Gln Glu Leu Val Asp Val Ile Lys Lys Ala
        2020                2025                2030

Tyr Leu Gln Glu Glu Arg Glu Asn Ser Glu Val Ser Pro Arg Glu
        2035                2040                2045

Val Gly His Asn Ile Tyr Ile Leu Ala Leu Gln Leu Ser Arg His Asn
        2050                2055                2060

Lys Gln Leu Gln His Leu Leu Lys Pro Val Lys Arg Ile Gln Glu Glu
2065                2070                2075                2080

Glu Ala Glu Gly Ile Ser Ser Met Leu Ser Leu Asn Asn Lys Gln Leu
        2085                2090                2095

Ser Gln Met Leu Lys Ser Ser Ala Pro Ala Gln Glu Glu Glu Glu Asp
        2100                2105                2110

Pro Leu Ala Tyr Tyr Glu Asn His Thr Ser Gln Ile Glu Ile Val Arg
        2115                2120                2125

Gln Asp Arg Ser Met Glu Gln Ile Val Phe Pro Val Pro Gly Ile Cys
        2130                2135                2140

Gln Phe Leu Thr Glu Glu Thr Lys His Arg Leu Phe Thr Thr Thr Glu
2145                2150                2155                2160

Gln Asp Glu Gln Gly Ser Lys Val Ser Asp Phe Phe Asp Gln Ser Ser
        2165                2170                2175

Phe Leu His Asn Glu Met Glu Trp Gln Arg Asn Val Arg Ser Met Pro
        2180                2185                2190

Leu Ile Tyr Trp Phe Ser Arg Arg Met Thr Leu Trp Gly Ser Ile Ser
        2195                2200                2205

Phe Asn Leu Ala Val Phe Ile Asn Ile Ile Ala Phe Phe Tyr Pro
        2210                2215                2220

Tyr Met Glu Gly Ala Ser Thr Gly Val Leu Asp Ser Pro Leu Ile Ser
2225                2230                2235                2240

Leu Leu Phe Trp Ile Leu Ile Cys Phe Ser Ile Ala Ala Leu Phe Thr
        2245                2250                2255

```
Lys Arg Tyr Ser Ile Arg Pro Leu Ile Val Ala Leu Ile Leu Arg Ser
            2260                2265                2270

Ile Tyr Tyr Leu Gly Ile Gly Pro Thr Leu Asn Ile Leu Gly Ala Leu
        2275                2280                2285

Asn Leu Thr Asn Lys Ile Val Phe Val Val Ser Phe Val Gly Asn Arg
    2290                2295                2300

Gly Thr Phe Ile Arg Gly Tyr Lys Ala Met Val Met Asp Met Glu Phe
2305                2310                2315                2320

Leu Tyr His Val Gly Tyr Ile Leu Thr Ser Val Leu Gly Leu Phe Ala
            2325                2330                2335

His Glu Leu Phe Tyr Ser Ile Leu Leu Phe Asp Leu Ile Tyr Arg Glu
        2340                2345                2350

Glu Thr Leu Phe Asn Val Ile Lys Ser Val Thr Arg Asn Gly Arg Ser
    2355                2360                2365

Ile Leu Leu Thr Ala Leu Leu Ala Leu Ile Leu Val Tyr Leu Phe Ser
        2370                2375                2380

Ile Val Gly Phe Leu Phe Leu Lys Asp Asp Phe Ile Leu Glu Val Asp
2385                2390                2395                2400

Arg Leu Pro Asn Asn His Ser Thr Ala Ser Pro Leu Gly Met Pro His
            2405                2410                2415

Gly Ala Ala Phe Val Asp Thr Cys Ser Gly Asp Lys Met Asp Cys
        2420                2425                2430

Val Ser Gly Leu Ser Val Pro Glu Val Leu Glu Glu Asp Arg Glu Leu
            2435                2440                2445

Asp Ser Thr Glu Arg Ala Cys Asp Thr Leu Leu Met Cys Ile Val Thr
2450                2455                2460

Val Met Asn His Gly Leu Arg Asn Gly Gly Gly Val Gly Asp Ile Leu
2465                2470                2475                2480

Arg Lys Pro Ser Lys Asp Glu Ser Leu Phe Pro Ala Arg Val Val Tyr
            2485                2490                2495

Asp Leu Leu Phe Phe Phe Ile Val Ile Ile Ile Val Leu Asn Leu Ile
        2500                2505                2510

Phe Gly Val Ile Ile Asp Thr Phe Ala Asp Leu Arg Ser Glu Lys Gln
        2515                2520                2525

Lys Lys Glu Glu Ile Leu Lys Thr Thr Cys Phe Ile Cys Gly Leu Glu
    2530                2535                2540

Arg Asp Lys Phe Asp Asn Lys Thr Val Ser Phe Glu Glu His Ile Lys
2545                2550                2555                2560

Leu Glu His Asn Met Trp Asn Tyr Leu Tyr Phe Ile Val Leu Val Arg
            2565                2570                2575

Val Lys Asn Lys Thr Asp Tyr Thr Gly Pro Glu Ser Tyr Val Ala Gln
        2580                2585                2590

Met Ile Lys Asn Lys Asn Leu Asp Trp Phe Pro Arg Met Arg Ala Met
        2595                2600                2605

Ser Leu Val Ser Asn Glu Gly Glu Gly Glu Gln Asn Glu Ile Arg Ile
    2610                2615                2620

Leu Gln Asp Lys Leu Asn Ser Thr Met Lys Leu Val Ser His Leu Thr
2625                2630                2635                2640

Ala Gln Leu Asn Glu Leu Lys Glu Gln Met Thr Glu Gln Arg Lys Arg
            2645                2650                2655

Arg Gln Arg Leu Gly Phe Val Asp Val Gln Asn Cys Ile Ser Arg
        2660                2665                2670
```